US012589007B2

(12) United States Patent
Sullivan et al.

(10) Patent No.: US 12,589,007 B2
(45) Date of Patent: Mar. 31, 2026

(54) INTRADISCAL FIXATION SYSTEMS

(71) Applicant: GLOBUS MEDICAL, INC., Audubon, PA (US)

(72) Inventors: Myles Sullivan, Philadelphia, PA (US); Carly Taubenkraut, Perkasie, PA (US); Mark Weiman, Downingtown, PA (US)

(73) Assignee: Globus Medical, Inc., Audubon, PA (US)

( * ) Notice: Subject to any disclaimer, the term of this patent is extended or adjusted under 35 U.S.C. 154(b) by 1133 days.

(21) Appl. No.: 17/560,483

(22) Filed: Dec. 23, 2021

(65) Prior Publication Data

US 2022/0117749 A1     Apr. 21, 2022

Related U.S. Application Data

(63) Continuation-in-part of application No. 16/924,423, filed on Jul. 9, 2020, now Pat. No. 11,491,020.

(51) Int. Cl.
| | |
|---|---|
| *A61F 2/44* | (2006.01) |
| *A61B 17/70* | (2006.01) |
| *A61F 2/30* | (2006.01) |
| *A61F 2/46* | (2006.01) |

(52) U.S. Cl.
CPC .......... *A61F 2/447* (2013.01); *A61B 17/7059* (2013.01); *A61F 2/30749* (2013.01); *A61F 2/30771* (2013.01); *A61F 2/4455* (2013.01); *A61F 2/4611* (2013.01); *A61F 2002/30092* (2013.01); *A61F 2002/30131* (2013.01); *A61F 2002/30405* (2013.01); *A61F 2002/30471*
(2013.01); *A61F 2002/30537* (2013.01); *A61F 2002/3054* (2013.01); *A61F 2002/30579* (2013.01); *A61F 2002/30624* (2013.01); *A61F 2002/30841* (2013.01); *A61F 2002/3085* (2013.01); *A61F 2002/4633* (2013.01)

(58) Field of Classification Search
CPC ........ A61F 2/44; A61F 2/4425; A61F 2/4455; A61F 2002/443; A61F 2002/448; A61F 2002/4485; A61F 2002/4415
See application file for complete search history.

(56) References Cited

U.S. PATENT DOCUMENTS

| | | | |
|---|---|---|---|
| 4,349,921 | A | 9/1982 | Kuntz |
| 4,599,086 | A | 7/1986 | Doty |
| 4,863,476 | A | 9/1989 | Shepperd |
| 4,863,477 | A | 9/1989 | Monson |
| 5,123,926 | A | 6/1992 | Pisharodi |
| 5,290,312 | A | 3/1994 | Kojimoto et al. |

(Continued)

FOREIGN PATENT DOCUMENTS

| | | |
|---|---|---|
| CA | 2088066 A1 | 1/1992 |
| DE | 1012622 C1 | 7/1991 |

(Continued)

*Primary Examiner* — Anu Ramana

(57) ABSTRACT

Intradiscal implants, systems, and methods thereof. The intradiscal system may include an expandable implant and one or more intradiscal implants. The intradiscal implants may be supplemental to or integrated with the expandable implant. The intradiscal implant may include one or more flexible anchors with a straight configuration and a curved configuration. The anchor may be bendable, for example, using a shape-memory material.

9 Claims, 77 Drawing Sheets

(56) References Cited

U.S. PATENT DOCUMENTS

| | | | |
|---|---|---|---|
| 5,306,310 A | 4/1994 | Siebels | |
| 5,375,823 A | 12/1994 | Navas | |
| 5,390,683 A | 2/1995 | Pisharodi | |
| 5,522,899 A | 6/1996 | Michelson | |
| 5,534,030 A | 7/1996 | Navarro et al. | |
| 5,554,191 A | 9/1996 | Lahille et al. | |
| 5,571,192 A | 11/1996 | Schonhoffer | |
| 5,645,596 A | 7/1997 | Kim | |
| 5,653,763 A | 8/1997 | Errico et al. | |
| 5,665,122 A | 9/1997 | Kambin | |
| 5,676,701 A | 10/1997 | Yuan et al. | |
| 6,039,761 A | 3/2000 | Li et al. | |
| 6,045,579 A | 4/2000 | Hochschuler et al. | |
| 6,080,193 A | 6/2000 | Hochshuler | |
| 6,099,531 A | 8/2000 | Bonutti | |
| 6,126,689 A | 10/2000 | Brett | |
| 6,176,882 B1 | 1/2001 | Biedermann | |
| 6,258,125 B1 | 7/2001 | Paul et al. | |
| 6,554,863 B2 | 4/2003 | Paul et al. | |
| 6,558,423 B1 | 5/2003 | Michelson | |
| 6,562,074 B2 | 5/2003 | Gerbec et al. | |
| 6,576,016 B1 | 6/2003 | Hochschuler et al. | |
| 6,641,614 B1 | 11/2003 | Wagner et al. | |
| 6,648,917 B2 | 11/2003 | Gerbec et al. | |
| 6,666,891 B2 | 12/2003 | Boehm, Jr. et al. | |
| 6,692,495 B1 | 2/2004 | Zacouto | |
| 6,706,070 B1 | 3/2004 | Wagner et al. | |
| 6,752,832 B2 | 6/2004 | Ulrich | |
| 6,814,756 B1 | 11/2004 | Michelson | |
| 6,830,589 B2 | 12/2004 | Erickson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,881,228 B2 | 4/2005 | Zdeblick et al. | |
| 7,018,415 B1 | 3/2006 | McKay | |
| 7,070,598 B2 | 7/2006 | Lim et al. | |
| 7,204,853 B2 | 4/2007 | Gordon | |
| 7,217,291 B2 | 5/2007 | Zucherman et al. | |
| 7,282,063 B2 | 10/2007 | Cohen et al. | |
| 7,316,714 B2 | 1/2008 | Gordon | |
| 7,473,276 B2 | 1/2009 | Aebi et al. | |
| 7,547,325 B2 | 6/2009 | Biedermann et al. | |
| 7,621,953 B2 | 11/2009 | Braddock, Jr. et al. | |
| 7,641,693 B2 | 1/2010 | Gutlin et al. | |
| 7,682,396 B2 | 3/2010 | Beaurain et al. | |
| 7,749,270 B2 | 7/2010 | Peterman | |
| 7,753,958 B2 | 7/2010 | Gordon | |
| 7,771,473 B2 | 8/2010 | Thramann | |
| 7,780,732 B2 | 8/2010 | Abernathie | |
| 7,799,081 B2 | 9/2010 | McKinley | |
| 7,815,683 B2 | 10/2010 | Melkent et al. | |
| 7,837,734 B2 | 11/2010 | Zucherman et al. | |
| 7,875,078 B2 | 1/2011 | Wysocki et al. | |
| 7,901,409 B2 | 3/2011 | Canaveral et al. | |
| 7,909,869 B2 | 3/2011 | Gordon | |
| 7,918,879 B2 * | 4/2011 | Yeung | A61B 17/0642 |
| | | | 606/139 |
| 7,951,199 B2 | 5/2011 | Miller | |
| 7,985,256 B2 | 7/2011 | Grotz et al. | |
| 8,062,375 B2 | 11/2011 | Glerum | |
| 8,070,813 B2 | 12/2011 | Grotz et al. | |
| 8,123,810 B2 | 2/2012 | Gordon | |
| 8,137,405 B2 | 3/2012 | Kostuik | |
| 8,192,495 B2 | 6/2012 | Simpson et al. | |
| 8,303,663 B2 | 11/2012 | Jimenez et al. | |
| 8,323,341 B2 * | 12/2012 | Lambrecht | A61B 17/0642 |
| | | | 623/17.11 |
| 8,377,140 B2 | 2/2013 | DeFalco et al. | |
| 8,394,129 B2 * | 3/2013 | Morgenstern Lopez | |
| | | | A61B 17/8858 |
| | | | 606/279 |
| 8,394,143 B2 | 3/2013 | Grotz et al. | |
| 8,435,296 B2 | 5/2013 | Kadaba et al. | |
| 8,454,695 B2 | 6/2013 | Grotz et al. | |
| 8,647,386 B2 | 2/2014 | Gordon | |
| 8,696,751 B2 | 4/2014 | Ashley et al. | |
| 8,771,360 B2 | 7/2014 | Jimenez et al. | |
| 8,894,710 B2 | 11/2014 | Simpson et al. | |
| 8,932,355 B2 | 1/2015 | Grotz et al. | |
| 8,940,049 B1 | 1/2015 | Jimenez et al. | |
| 8,956,413 B2 | 2/2015 | Ashley et al. | |
| 8,992,620 B2 | 3/2015 | Ashley et al. | |
| 9,028,550 B2 | 5/2015 | Shulock et al. | |
| 9,179,952 B2 * | 11/2015 | Biedermann | A61B 17/8047 |
| 9,314,284 B2 * | 4/2016 | Chan | A61B 17/1782 |
| 9,358,125 B2 | 6/2016 | Jimenez et al. | |
| 9,532,883 B2 | 1/2017 | McLuen et al. | |
| 9,622,878 B2 | 4/2017 | Grotz | |
| 10,687,957 B2 * | 6/2020 | Pimenta | A61F 2/447 |
| 10,856,997 B2 * | 12/2020 | Cowan | A61F 2/447 |
| 11,357,640 B2 * | 6/2022 | Weiman | A61F 2/4425 |
| 11,534,309 B1 * | 12/2022 | Weiman | A61B 34/30 |
| 12,178,713 B2 * | 12/2024 | Weiman | A61F 2/4425 |
| 12,239,544 B2 * | 3/2025 | Dewey | A61F 2/4455 |
| 2002/0045945 A1 | 4/2002 | Liu | |
| 2002/0068976 A1 | 6/2002 | Jackson | |
| 2002/0068977 A1 | 6/2002 | Jackson | |
| 2003/0176926 A1 | 9/2003 | Boehm et al. | |
| 2004/0030387 A1 | 2/2004 | Landry | |
| 2004/0049271 A1 | 3/2004 | Biedermann | |
| 2004/0054412 A1 | 3/2004 | Gerbec et al. | |
| 2004/0087947 A1 | 5/2004 | Lim et al. | |
| 2004/0153065 A1 | 8/2004 | Lim | |
| 2005/0021041 A1 | 1/2005 | Michelson | |
| 2005/0021145 A1 | 1/2005 | de Villiers | |
| 2005/0033432 A1 | 2/2005 | Gordon | |
| 2005/0080422 A1 | 4/2005 | Otte | |
| 2005/0113916 A1 | 5/2005 | Branch, Jr. | |
| 2005/0149188 A1 | 7/2005 | Cook | |
| 2005/0171541 A1 | 8/2005 | Boehm | |
| 2005/0251258 A1 | 11/2005 | Jackson | |
| 2005/0273171 A1 | 12/2005 | Gordon | |
| 2005/0273174 A1 | 12/2005 | Gordon | |
| 2005/0278026 A1 | 12/2005 | Gordon | |
| 2005/0283244 A1 | 12/2005 | Gordon | |
| 2005/0283245 A1 | 12/2005 | Gordon | |
| 2006/0004453 A1 | 1/2006 | Bartish, Jr. et al. | |
| 2006/0015184 A1 | 1/2006 | Winterbottom | |
| 2006/0058878 A1 | 3/2006 | Michelson | |
| 2006/0084986 A1 | 4/2006 | Grinberg | |
| 2006/0122701 A1 | 6/2006 | Kister | |
| 2006/0129244 A1 | 6/2006 | Ensign | |
| 2006/0142859 A1 | 6/2006 | McLuen | |
| 2006/0149385 A1 | 7/2006 | McKay | |
| 2006/0195192 A1 | 8/2006 | Gordon et al. | |
| 2006/0229729 A1 | 10/2006 | Gordon | |
| 2006/0241770 A1 | 10/2006 | Rhoda | |
| 2006/0253201 A1 | 11/2006 | Mcluen | |
| 2007/0043442 A1 | 2/2007 | Abernathie | |
| 2007/0050030 A1 | 3/2007 | Kim | |
| 2007/0050032 A1 | 3/2007 | Gittings et al. | |
| 2007/0055377 A1 | 3/2007 | Hanson et al. | |
| 2007/0191951 A1 | 8/2007 | Branch | |
| 2007/0255415 A1 | 11/2007 | Edie et al. | |
| 2007/0270963 A1 | 11/2007 | Melkent et al. | |
| 2007/0270968 A1 | 11/2007 | Baynham | |
| 2008/0021559 A1 | 1/2008 | Thramann | |
| 2008/0065222 A1 | 3/2008 | Hamada | |
| 2008/0114467 A1 | 5/2008 | Capote | |
| 2008/0140207 A1 | 6/2008 | Olmos | |
| 2008/0147194 A1 | 6/2008 | Grotz | |
| 2008/0161933 A1 | 7/2008 | Grotz et al. | |
| 2008/0167657 A1 | 7/2008 | Greenhalgh | |
| 2008/0183204 A1 | 7/2008 | Greenhalgh et al. | |
| 2008/0221694 A1 | 9/2008 | Warnick | |
| 2008/0275455 A1 | 11/2008 | Berry et al. | |
| 2008/0281346 A1 | 11/2008 | Greenhalgh et al. | |
| 2008/0288073 A1 | 11/2008 | Renganath et al. | |
| 2008/0300598 A1 | 12/2008 | Barreiro et al. | |
| 2008/0306488 A1 | 12/2008 | Altarac et al. | |
| 2008/0319487 A1 | 12/2008 | Fielding et al. | |
| 2008/0319549 A1 | 12/2008 | Greenhalgh et al. | |
| 2009/0024217 A1 | 1/2009 | Levy | |
| 2009/0062833 A1 | 3/2009 | Song | |

(56) References Cited

U.S. PATENT DOCUMENTS

| | | |
|---|---|---|
| 2009/0076616 A1 | 3/2009 | Duggal |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger |
| 2010/0286783 A1 | 11/2010 | Lechmann |
| 2011/0035011 A1 | 2/2011 | Cain |
| 2011/0093074 A1 | 4/2011 | Glerum |
| 2011/0160861 A1 | 6/2011 | Jimenez |
| 2011/0172774 A1 | 7/2011 | Varela |
| 2011/0276142 A1 | 11/2011 | Niemiec |
| 2011/0301713 A1 | 12/2011 | Theofilos |
| 2011/0319997 A1 | 12/2011 | Glerum |
| 2012/0035729 A1 | 2/2012 | Glerum |
| 2012/0059470 A1 | 3/2012 | Weiman |
| 2012/0059472 A1 | 3/2012 | Weiman |
| 2012/0109308 A1 | 5/2012 | Lechmann |
| 2012/0130496 A1 | 5/2012 | Duffield |
| 2012/0165945 A1 | 6/2012 | Hansell |
| 2012/0185049 A1 | 7/2012 | Varela |
| 2012/0209386 A1 | 8/2012 | Triplett |
| 2012/0215313 A1 | 8/2012 | Saidha |
| 2012/0226357 A1 | 9/2012 | Varela |
| 2012/0265309 A1 | 10/2012 | Glerum |
| 2012/0277861 A1 | 11/2012 | Steele et al. |
| 2012/0277870 A1 | 11/2012 | Wolters |
| 2012/0323329 A1 | 12/2012 | Jimenez |
| 2012/0330426 A1 | 12/2012 | McLaughlin |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4012622 C1 | 7/1991 |
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 | 12/2000 |
| FR | 2794968 A1 | 12/2000 |
| JP | 2000-513263 | 10/2000 |
| JP | 2000-513263 A | 10/2000 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 199942062 A1 | 8/1999 |
| WO | 1999042062 A1 | 8/1999 |
| WO | 199966867 A1 | 12/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |

* cited by examiner

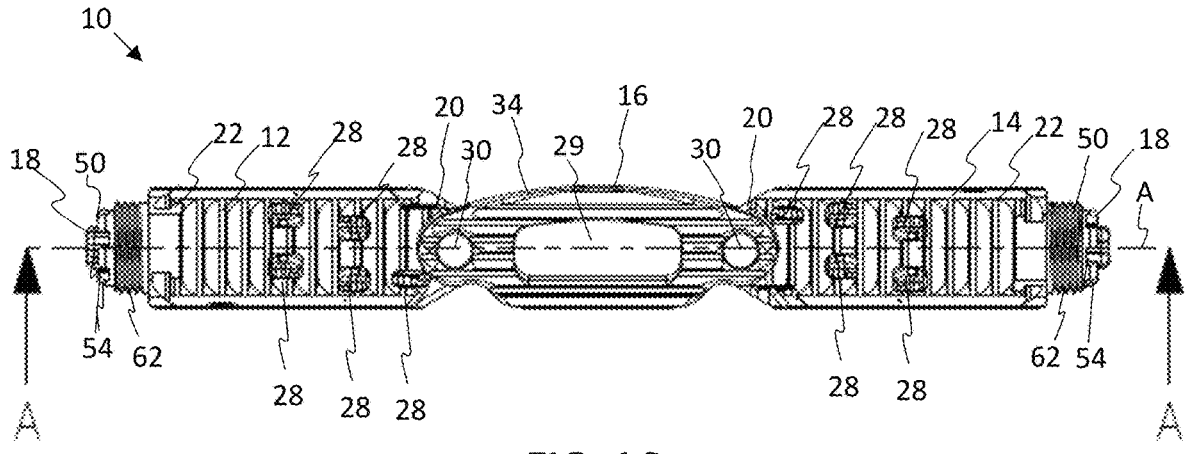
FIG. 1C
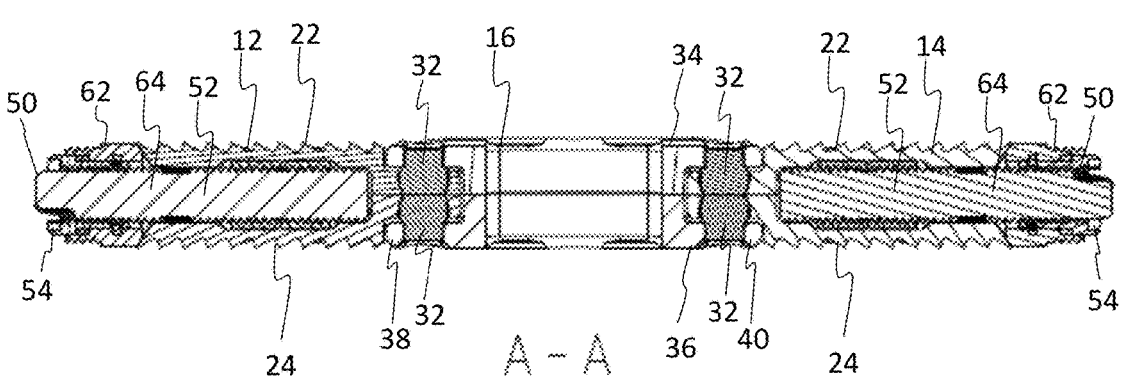
A - A
FIG. 1D
FIG. 1E

A – A

C – C

A - A

C - C

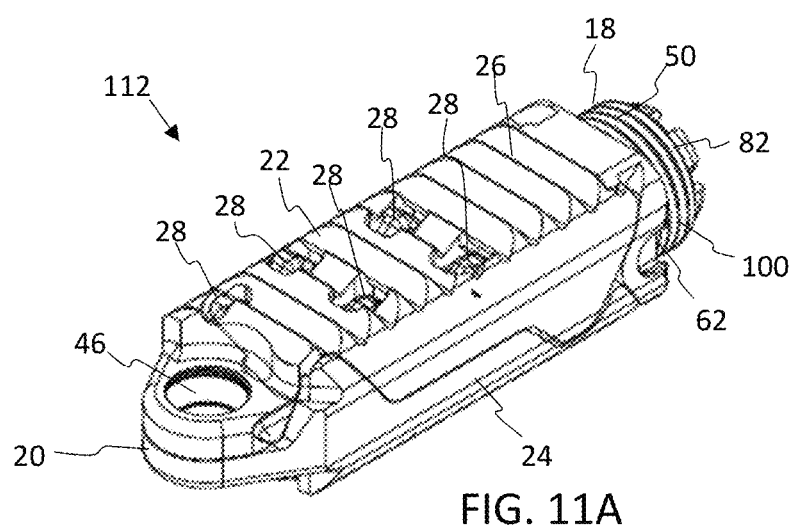
FIG. 11A
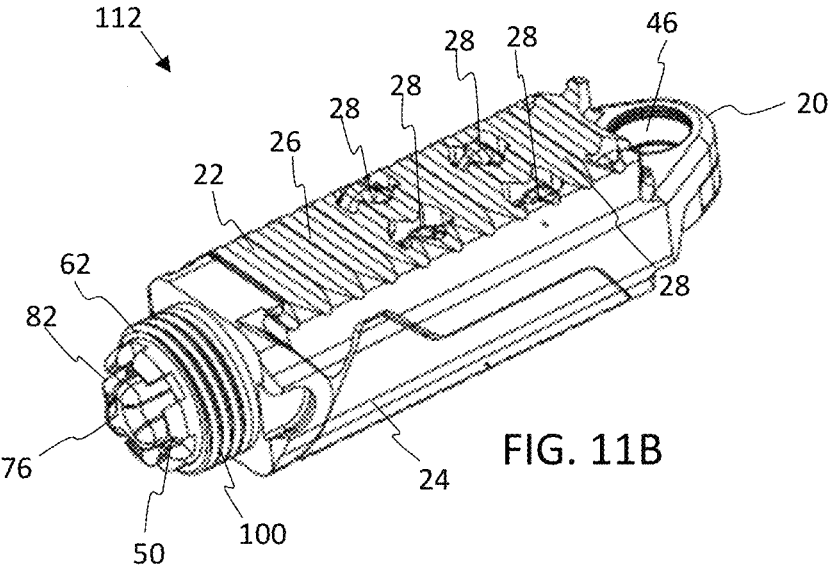
FIG. 11B
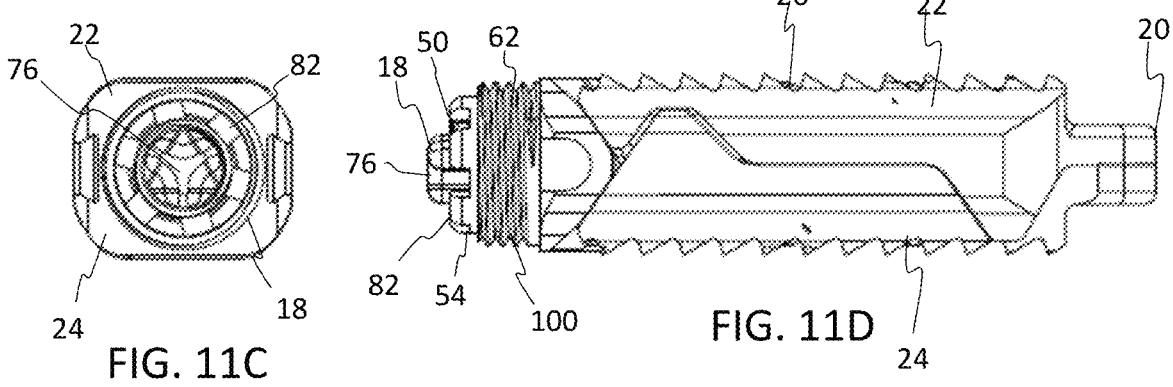
FIG. 11C
FIG. 11D

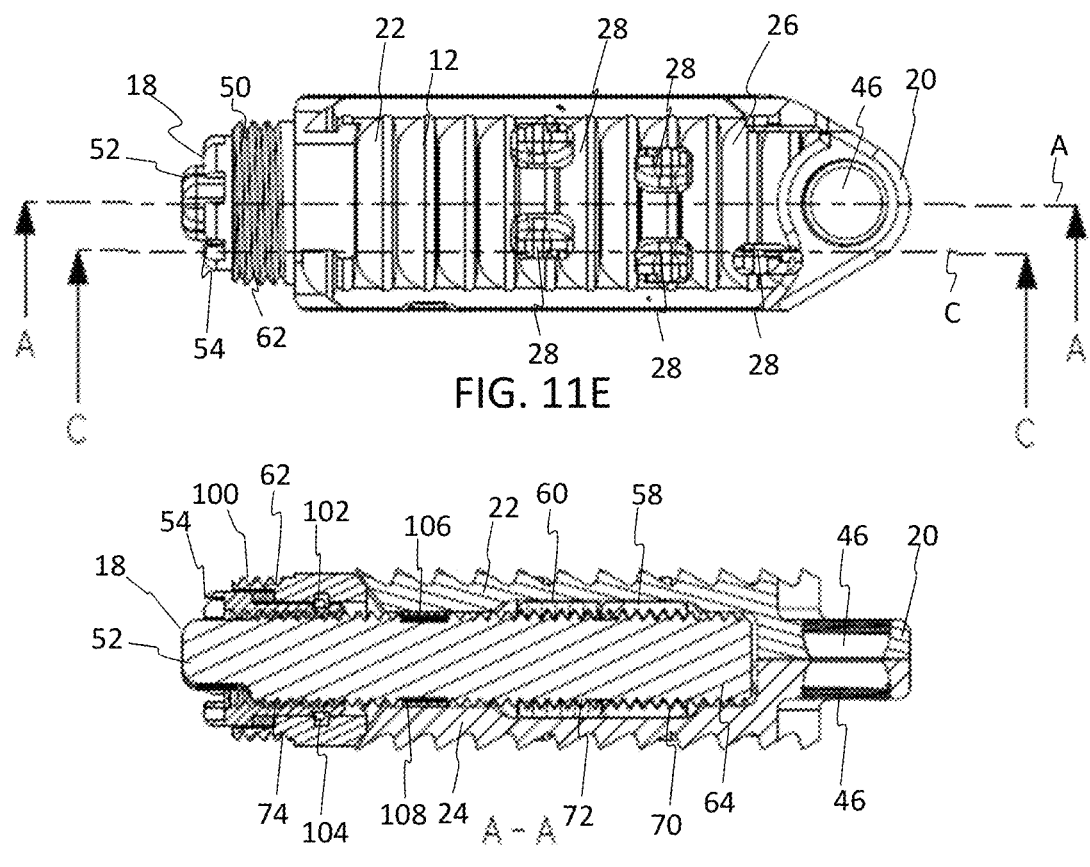
FIG. 11E
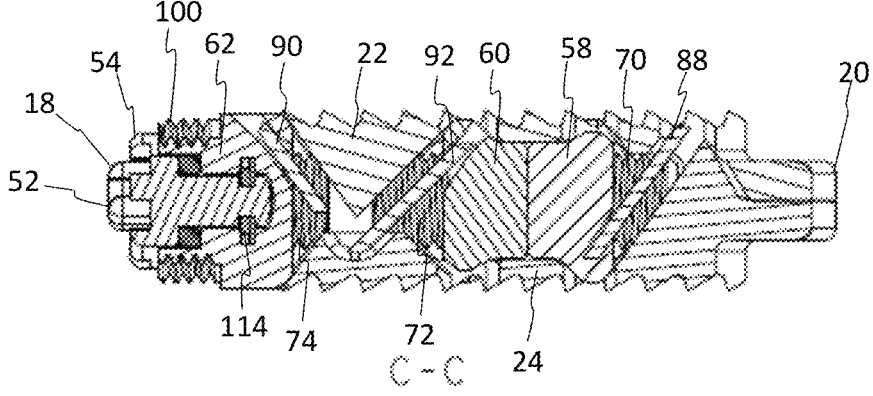
FIG. 11F
FIG. 11G

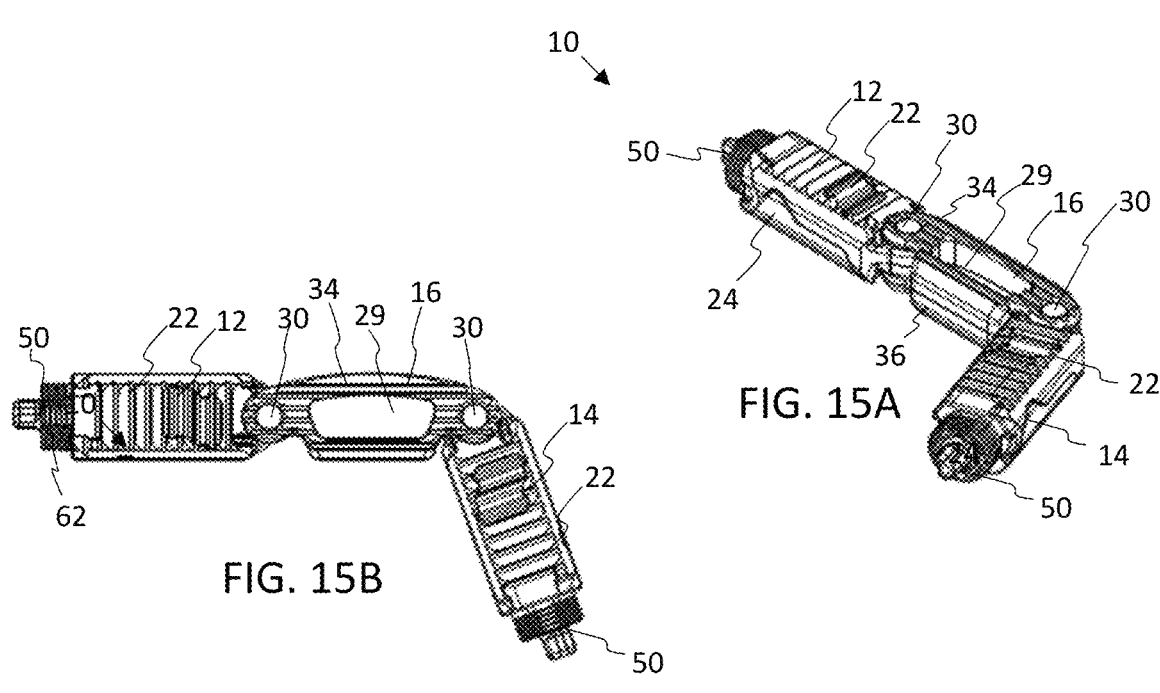
FIG. 15A
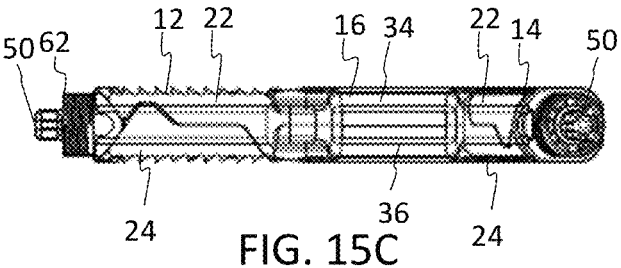
FIG. 15B
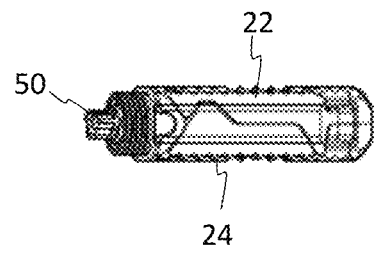
FIG. 15C
FIG. 15D
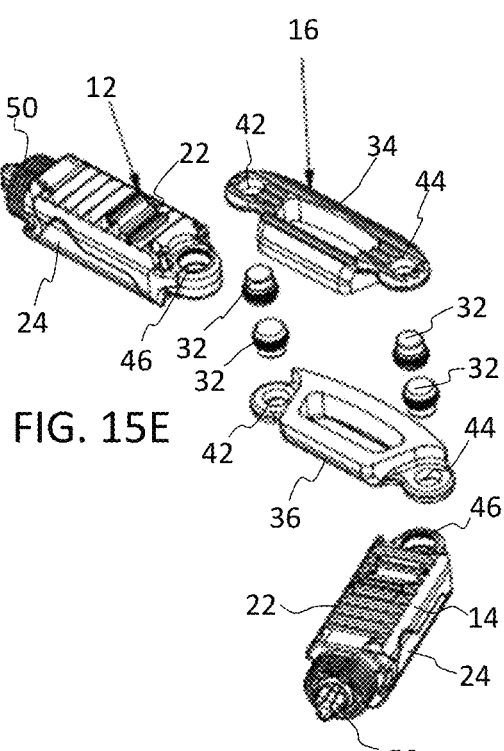
FIG. 15E

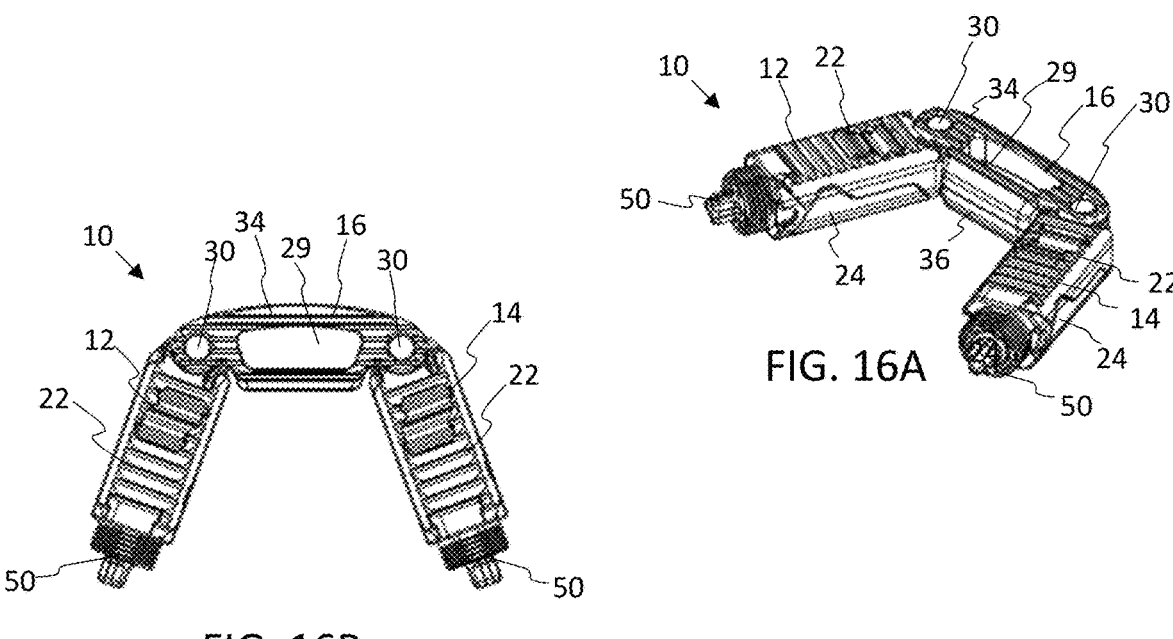
FIG. 16A
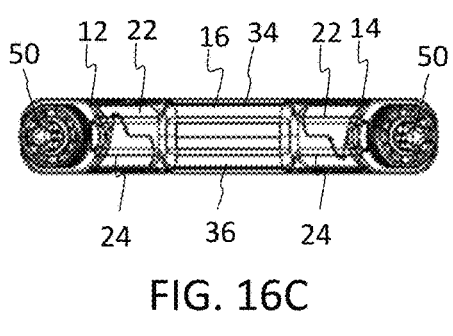
FIG. 16B
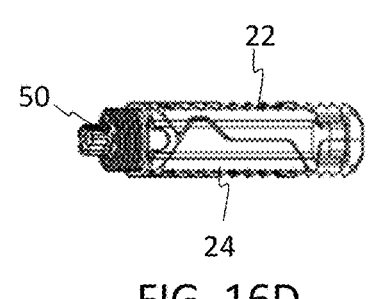
FIG. 16C
FIG. 16D
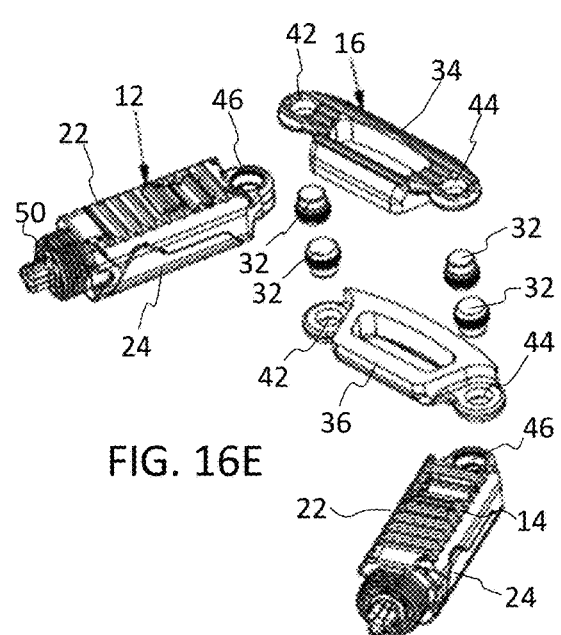
FIG. 16E

A-A

C-C

A-A

C-C

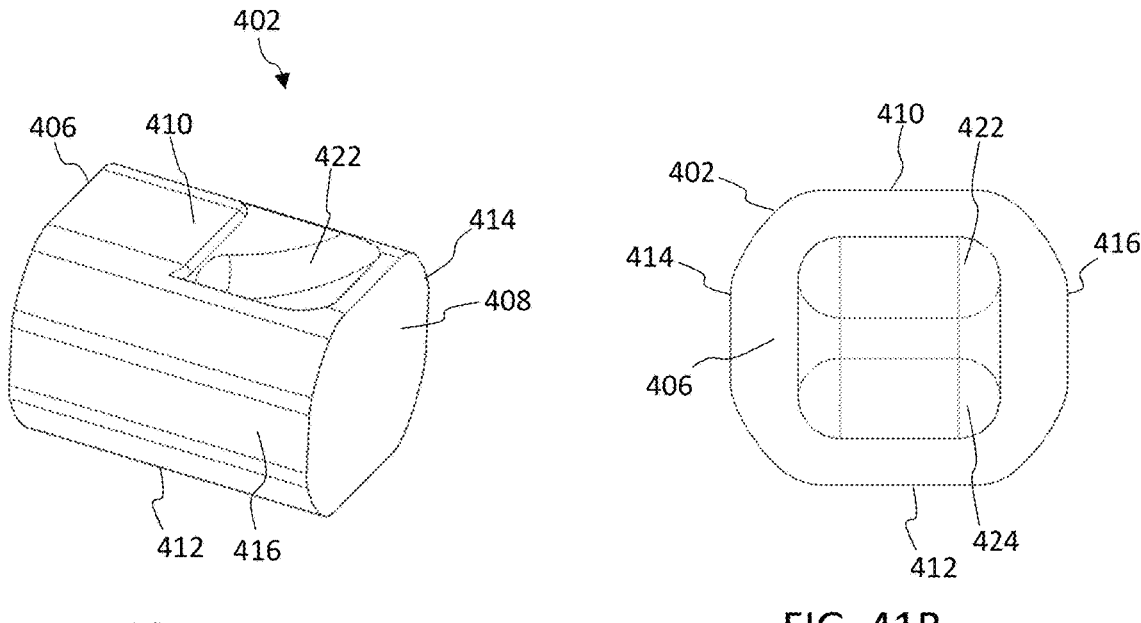
FIG. 41A
FIG. 41B
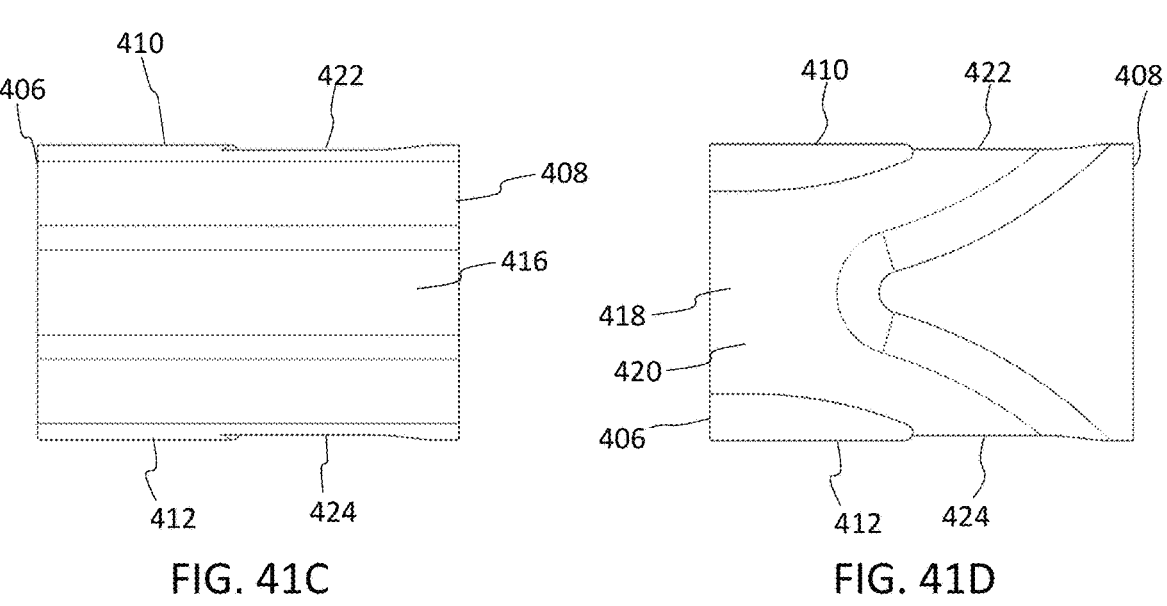
FIG. 41C
FIG. 41D

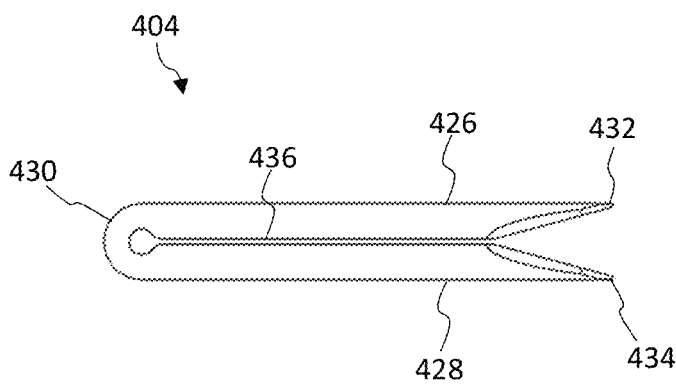
FIG. 42A
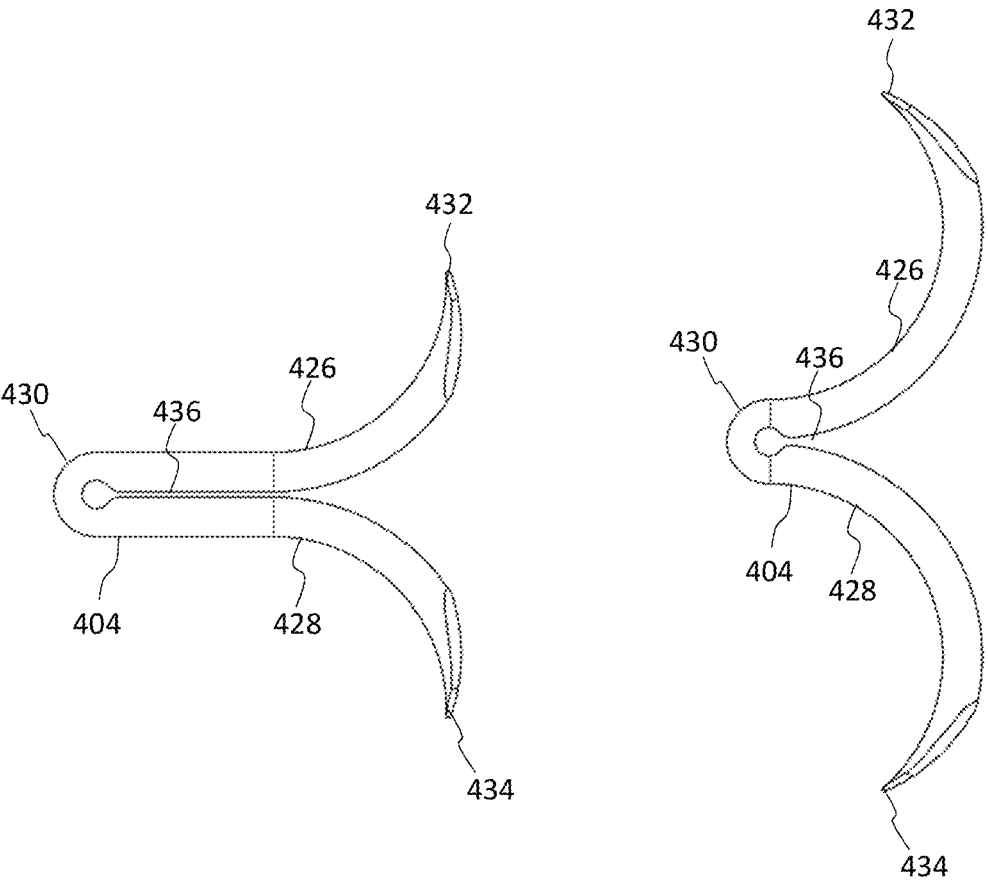
FIG. 42B                                    FIG. 42C

INTRADISCAL FIXATION SYSTEMS

CROSS REFERENCE TO RELATED APPLICATIONS

This application is a continuation-in-part of U.S. patent application Ser. No. 16/924,423, filed on Jul. 9, 2020, which is incorporated by reference herein in its entirety for all purposes.

FIELD OF THE INVENTION

The present disclosure relates to surgical devices, and more particularly, to intradiscal fixation systems including expandable fusion devices with integrated or supplemental fixation for restoring spinal stability and/or promoting spinal fusion.

BACKGROUND OF THE INVENTION

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

Bilateral pedicle screw (BPS) fixation may be used to treat degenerative disc disease and a multitude of other spine pathologies to stabilize two or more adjacent vertebras to promote spinal fusion. A number of iatrogenic pathologies are associated with pedicle screw fixation, including but not limited to misplacement of screws, muscle/ligamentous disruption during insertion, adjacent segment disease resulting from superior adjacent facet violation by pedicle screw insertion, increased procedural time, and instrumentation failure.

There remains a clinical need for a minimally invasive spine (MIS) fixation system that removes the risks associated with the insertion and placement of pedicle-based screw constructs. As such, there exists a need for an intradiscal fixation system that reduces the iatrogenic effects caused by surgery while achieving the stability needed to promote spinal fusion.

SUMMARY OF THE INVENTION

To meet this and other needs, orthopedic implants, systems, instruments, and methods are provided. The implant system may include an expandable fusion device used alone or in combination with one or more intradiscal fixation implants. In particular, the expandable fusion device may include a three-legged expandable interbody, which has first and second lateral legs and one or more link plates pivotably coupled between the first and second lateral legs. The lateral legs and link plates may be aligned to form a linear orientation, and the lateral legs may be pivotable relative to the link plates to form a widened U-shaped orientation for the implant. The lateral legs and attached link plates may be expanded to adjust lordosis and/or coronal balance. The device may be installed in an open, semi-open, or minimally invasive surgical procedure. The expandable fusion device may be capable of being placed into the disc space, for example, down a guide tube or cannula and then expanded in height into an expanded configuration. The intradiscal fixation implant may include a supplemental fixation system or an integrated standalone fixation system. The supplemental fixation system may include an intradiscal plating system with one or more flexible screws or a splayed anchor, for example.

According to one embodiment, an expandable implant includes first and second lateral legs and a link plate joined to each of the first and second lateral legs by a hinge. The first and second lateral legs each include upper and lower endplates configured to engage adjacent vertebrae, an actuator assembly including a rotatable actuator having a shaft and a rotatable nut, and a plurality of driving ramps including a front ramp, a mid-ramp, and a rear ramp positioned along the shaft of the actuator. The upper and lower endplates may be engaged with the plurality of driving ramps. Rotation of the actuator and/or the nut may cause movement of one or more of the driving ramps, thereby causing an expansion in height of the upper and lower endplates. The first and second lateral legs and link plate may be positionable along a central longitudinal axis of the implant, thereby forming a linear orientation configured to be inserted through a cannula. The first and second lateral legs may be pivotable about the respective hinges, thereby allowing for a widened U-shaped configuration of the implant.

The implant may include a first or upper link plate and a second or lower link plate. The first link plate may be hingedly connected to the upper endplates of the first and second lateral legs, and the second link plate may be hingedly connected to the lower endplates of the first and second lateral legs. The first and second link plates may be passively expanded when either or both of the first and second lateral legs are actively expanded.

The rotatable nut may be configured to move the rear ramp independent of the mid-ramp and the front ramp. In one embodiment, the shaft of the actuator may include a first threaded portion, a second threaded portion, and a third threaded portion. The front ramp may be positioned on and moveable along the first threaded portion of the actuator. The mid-ramp may be positioned on and moveable along the second threaded portion of the actuator. The rear ramp may be positioned on and moveable along the third threaded portion of the actuator. In another embodiment, the shaft of the actuator includes a first threaded portion, a second threaded portion, and a non-threaded portion. The front ramp may be positioned on the non-threaded portion of the actuator. The mid-ramp may be positioned on and moveable along the first threaded portion of the actuator. The rear ramp may be positioned on and moveable along the second threaded portion of the actuator. The threaded portions may have the same or different attributes including outer diameters, handedness, thread form, thread angle, lead, pitch, etc. In one embodiment, the first threaded portion may have a smaller outer diameter and different handedness than the second threaded portion of the actuator.

According to another embodiment, an expandable implant includes upper and lower link plates each extending from a first end to a second end and first and second lateral legs. The first and second lateral legs may each include upper and lower endplates configured to engage adjacent vertebrae, an actuator assembly including a rotatable actuator having a shaft and a rotatable nut, and a plurality of driving ramps including a front ramp, a mid-ramp, and a rear ramp positioned along the shaft of the actuator. The upper and lower endplates may be engaged with the plurality of driving ramps. Rotation of the actuator and/or the nut may cause movement of one or more of the driving ramps, thereby causing an expansion in height of the upper and lower endplates. The upper link plate may be pivotably coupled to the first lateral leg at the first end of the upper link plate and may be pivotably coupled to the second lateral leg at the second end of the upper link plate. The lower link plate may be pivotably coupled to the first lateral leg at the first end of the lower link plate and may be pivotably coupled to the second lateral leg at the second end of the lower link plate. The upper and lower link plates may be passively expanded when either or both of the first and second lateral legs are expanded.

The first and second lateral legs and upper and lower link plates may be positionable along a central longitudinal axis of the implant, thereby forming a linear orientation configured to be inserted through a cannula. The first and second lateral legs may be pivotable relative to the link plates, thereby allowing for a widened U-shaped configuration of the implant.

According to another embodiment, an expandable implant includes a strain gauge embedded in at least one of the first lateral leg, the second lateral leg, and the link plate. The strain gauge may include a plurality of sensors and a circuitry connecting the plurality of sensors. The strain gauge may measure the force, pressure, tension, and/or weight distribution across the surface area of the implant. A first strain gauge may be embedded in the upper endplate of the first lateral leg. A second strain gauge may be embedded in the upper endplate of the second lateral leg. A third strain gauge may be embedded in the upper link plate. At least one of the strain gauges may have a different circuitry that the other strain gauges. A fourth strain gauge may be embedded in the lower endplate of the first lateral leg. A fifth strain gauge may be embedded in the lower endplate of the second lateral leg. A sixth strain gauge may be embedded in the lower link plate. The first and second lateral legs and the link plates may be 3D printed. The strain gauges may be embedded in each of the first and second lateral legs and the link plates during the 3D printing process to provide a complete integration between the 3D printed material and the strain gauges.

According to yet another embodiment, methods of installing the expandable implants are provided. A disc space of a patient may be accessed and prepared from a posterior approach. A collapsed implant having a linear orientation may be positioned within the disc space via a cannula. The collapsed implant may be articulated into a widened U-shaped configuration. One or both of the lateral legs of the implant may be expanded in height, thereby passively expanding the attached link plates, to provide an expanded configuration for the implant. The cannula may be withdrawn from the patient's body, thereby leaving the implant in the expanded position.

According to another embodiment, a supplemental intradiscal implant includes a plate and an anchor. The plate has a body with a front face and opposite rear face, upper face and opposite lower face, and opposing sides. The plate has an opening extending through the plate. The anchor is receivable through the opening in the plate. The anchor has a head and a shaft extending from the head to a distal end. The shaft includes one or more threads. The anchor is flexible such that the anchor has a straight configuration and is bendable into a curved configuration.

The intradiscal implant may include one or more of the following features. When the shaft of the anchor is inserted through the opening in the plate, the shaft of the anchor may bend, and after the head of the anchor is seated in the opening, the shaft may straighten to the straight configuration. The anchor may be formed of a shape-memory material, such as nitinol. The anchor may be curved up to 45° (e.g., about 30°-45° relative to the cephalad-caudal plane) when in the curved profile. The opening may define one or more threads configured to mate with the corresponding threads on the anchor, thereby guiding insertion of the anchor. The plate may have first and second openings extending through the plate between the front and rear faces, and the first and second openings may be configured to receive first and second anchors. The first opening may be angled such that the first opening is oriented downwardly and the second opening is angled such that the second opening is oriented upwardly, thereby allowing for the first and second anchors to engage the adjacent vertebral bodies.

According to another embodiment, an intradiscal implant includes a plate and an anchor. The plate has a body with a front face and opposite rear face, upper face and opposite lower face, and opposing sides. The plate has an opening extending through the plate. The anchor is receivable through the opening in the plate. The anchor has an upper prong and a lower prong with free ends. The anchor is flexible such that the anchor has a straight configuration and the prongs are bendable into a curved configuration.

The intradiscal implant may include one or more of the following features. The anchor may be formed of a shape-memory material, such as nitinol. The upper and lower prongs may meet at a proximal end to form a U-shaped loop. In the straight configuration, the upper and lower prongs may be aligned in parallel. In the curved configuration, the free ends may bend outward and away from one another.

According to another embodiment, an intradiscal fixation system includes an expandable implant and a supplemental intradiscal implant. The expandable implant is configured to be positioned in a disc space and engage adjacent vertebrae. The supplemental intradiscal implant is configured to be positioned in the disc space adjacent to the expandable implant. The supplemental intradiscal implant includes a plate and an anchor. The anchor is flexible such that the anchor has a straight configuration and is bendable into a curved configuration.

The intradiscal fixation system may include one or more of the following features. The anchor may be formed of a shape-memory material, such as nitinol. The plate may define one or more openings configured to guide deployment of the anchor. The anchor may have a head and a shaft extending from the head to a distal end, and the shaft may include one or more threads. The anchor may have an upper prong and a lower prong coupled at a proximal end and having free ends at a distal end. The free ends of the prongs may be configured to splay apart.

According to another embodiment, an intradiscal fixation system includes an expandable implant and a pair of intradiscal implant. The expandable implant may include first and second lateral legs and at least one link plate joined to each of the first and second lateral legs by a hinge. Each of the first and second lateral legs may include upper and lower endplates configured to engage adjacent vertebrae. The pair of intradiscal implants are configured to be aligned with the first and second lateral legs of the expandable implant. Each intradiscal implant includes a flexible anchor, and the flexible anchor is moveable between a straight configuration and curved configuration.

The intradiscal fixation system may include one or more of the following features. The anchor may be formed of a shape-memory material, such as nitinol. The plate may define first and second openings having one or more threads. The system may include first and second anchors each having a head and a shaft extending from the head to a distal end. The shaft may include one or more threads configured to mate with the corresponding threads in the openings, thereby guiding insertion of the anchors. The plate may define a central channel that bifurcates into upper and lower branches, and the anchor may be a split anchor with an upper prong and a lower prong. When the split anchor is inserted through the central channel, the prongs may splay apart and are guided by the upper and lower branches to deploy the anchor. The first and second lateral legs of the expandable implant may each include an actuator assembly including a rotatable actuator having a shaft and a rotatable nut, and a plurality of driving ramps including a front ramp, a mid-ramp, and a rear ramp positioned along the shaft of the actuator. The upper and lower endplates may be engaged with the plurality of driving ramps. Rotation of the actuator and/or the nut may cause movement of one or more of the driving ramps, thereby causing an expansion in height of the upper and lower endplates.

According to another embodiment, a standalone integrated system includes an expandable implant with one or more flexible anchors. The expandable implant may include an integrated plate, extensions to the upper and lower endplates, or openings through the upper and lower endplates of the lateral legs of the expandable implant. In one embodiment, the flexible anchors include threaded screws with flexible shafts, which are configured to bend when positioned through the device. In another embodiment, the flexible anchors include a split anchor with a pair of prongs having free ends configured to splay outwardly when positioned through the device.

According to another embodiment, a method of stabilizing adjacent vertebrae includes one or more of the following steps in any suitable order: (1) inserting an expandable interbody implant in a disc space between the adjacent vertebrae; (2) expanding the expandable interbody implant to engage the adjacent vertebrae; (3) inserting a plate on a posterior edge of the disc space, the plate having an opening extending therethrough; and (4) positioning an anchor through the opening in the plate, wherein the anchor is flexible such that the anchor has a straight configuration and is bendable into a curved configuration. The method may also include, before inserting the expandable implant, (a) accessing the disc space from a transforaminal approach through Kambin's Triangle; (b) docking one or more cannulas on the posterior edge of the disc space; and (c) performing a discectomy with instrumentation to clear the disc space for the expandable interbody implant to be placed. The method may include inserting the plate and anchor in the disc space on the same trajectory and orientation as the expandable interbody implant. It will be appreciated that the method may be performed with or without navigation and/or robotic assistance.

According to another embodiment, a method of stabilizing adjacent vertebrae includes one or more of the following steps in any suitable order: (1) inserting an expandable implant in a disc space between the adjacent vertebrae, the expandable implant comprising first and second lateral legs and at least one link plate joined to each of the first and second lateral legs by a hinge, each of the first and second lateral legs including upper and lower endplates; (2) expanding the expandable implant to engage the adjacent vertebrae; (3) inserting a pair of plates bilaterally on a posterior edge of the disc space, the plates being aligned with the first and second lateral legs of the expandable implant, each plate having an opening extending therethrough; and (4) positioning flexible anchors through the openings in the plates, wherein the flexible anchors are moveable between straight and curved configurations. Each anchor may be inserted through a low straight configuration, bent, and then driven at an angle into the vertebrae. It will be appreciated that the method may be performed with or without navigation and/or robotic assistance.

According to another embodiment, a robotically-enabled method of stabilizing adjacent vertebrae includes one or more of the following steps in any suitable order: (1) providing a robotic system having a moveable end-effector with a guide tube and a cannula configured to guide an instrument along a desired access trajectory; (2) accessing a surgical site through the cannula; (3) deploying an expandable interbody implant through the cannula into a disc space between the adjacent vertebrae; (4) installing first and second intradiscal implants through the cannula, the intradiscal implants each including a plate and flexible anchors for engaging vertebral bodies of the adjacent vertebrae; and (5) verifying final positioning of the interbody and intradiscal implants. The first and second intradiscal implants may be inserted bilaterally on a posterior edge of the disc space. The first and second intradiscal implants may be inserted in the disc space on the same trajectory and orientation as the interbody implant. The first and second intradiscal implants may be introduced secondarily to the expandable interbody implant to improve stability of the intervertebral level.

The method may also include loading one of the anchors in a deployment instrument, attaching the deployment instrument to the plate, navigating the plate to an appropriate depth, and deploying the flexible anchor into the vertebral body. The method may further include attaching a locking cap to the flexible anchor to prevent back out. The method may include performing pre-operative planning with the robotic system by taking pre-operative images and planning positioning of one or more implants. The expandable interbody implant may include a first expandable lateral leg, a second expandable lateral leg, and a third central leg pivotably connected between the first and second lateral legs, wherein the first and second lateral legs are independently expandable in height to provide lordotic and/or coronal adjustments. The intradiscal implants may include a plate with flexible anchors. The flexible anchors may include screws with flexible shafts or splayed anchors, for example. It will be appreciated that the method may be performed with or without navigation and/or robotic assistance.

Also provided are kits including expandable fusion devices and intradiscal implants of varying types and sizes, rods, fasteners or anchors, k-wires, insertion tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIGS. 1A-1E are perspective, exploded, top, cross-sectional, and side views, respectively, of an expandable fusion device according to one embodiment, in a fully collapsed and linear orientation configured to be inserted into the body;

FIGS. 11A-11G show perspective, rear, side, top and cross-sectional views, respectively, of the lateral leg shown in FIG. 10 in a fully collapsed configuration;

FIGS. 15A-15E show perspective, top, rear, side, and exploded views of the expandable fusion device in FIGS. 14A-14E with a first lateral leg hinged at an angle with respect to link plates joining the two lateral legs;

FIGS. 16A-16E show perspective, top, rear, side, and exploded views of the expandable fusion device in FIGS. 15A-15E with both of the lateral legs hinged relative to the link plates to form a widened U-shaped configuration, and the implant is in the fully collapsed position;

FIGS. 41A-41D show perspective, front, side, and cross-sectional views, respectively, of the plate for the splayed anchor according to one embodiment;

FIGS. 42A-42C show straight and curved splayed anchors according to one embodiment;

DETAILED DESCRIPTION OF THE INVENTION

Figure 1A:
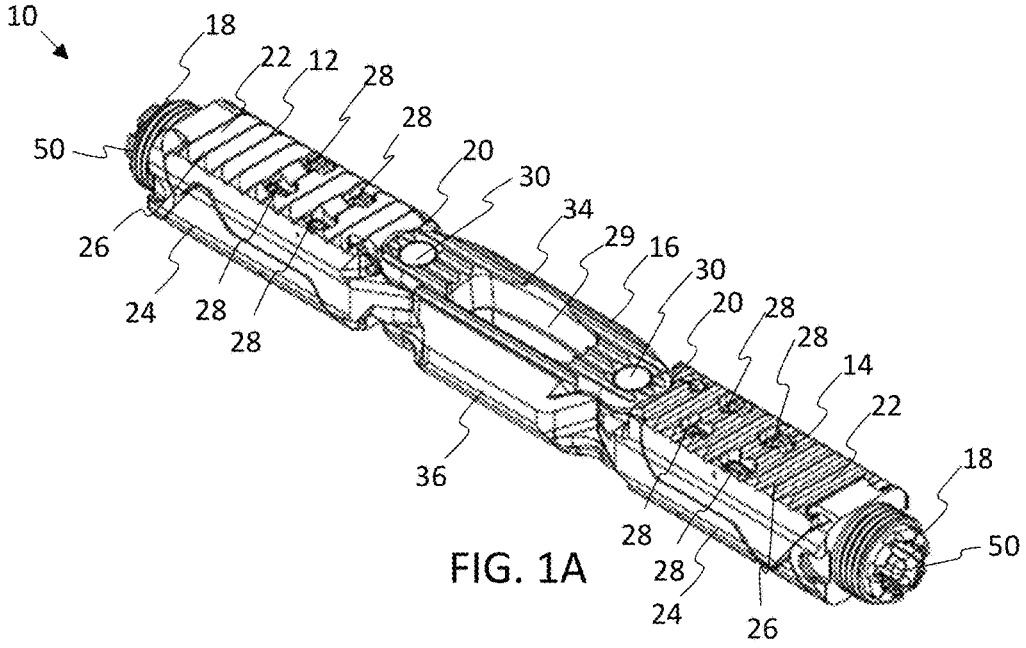
Figure 1B:
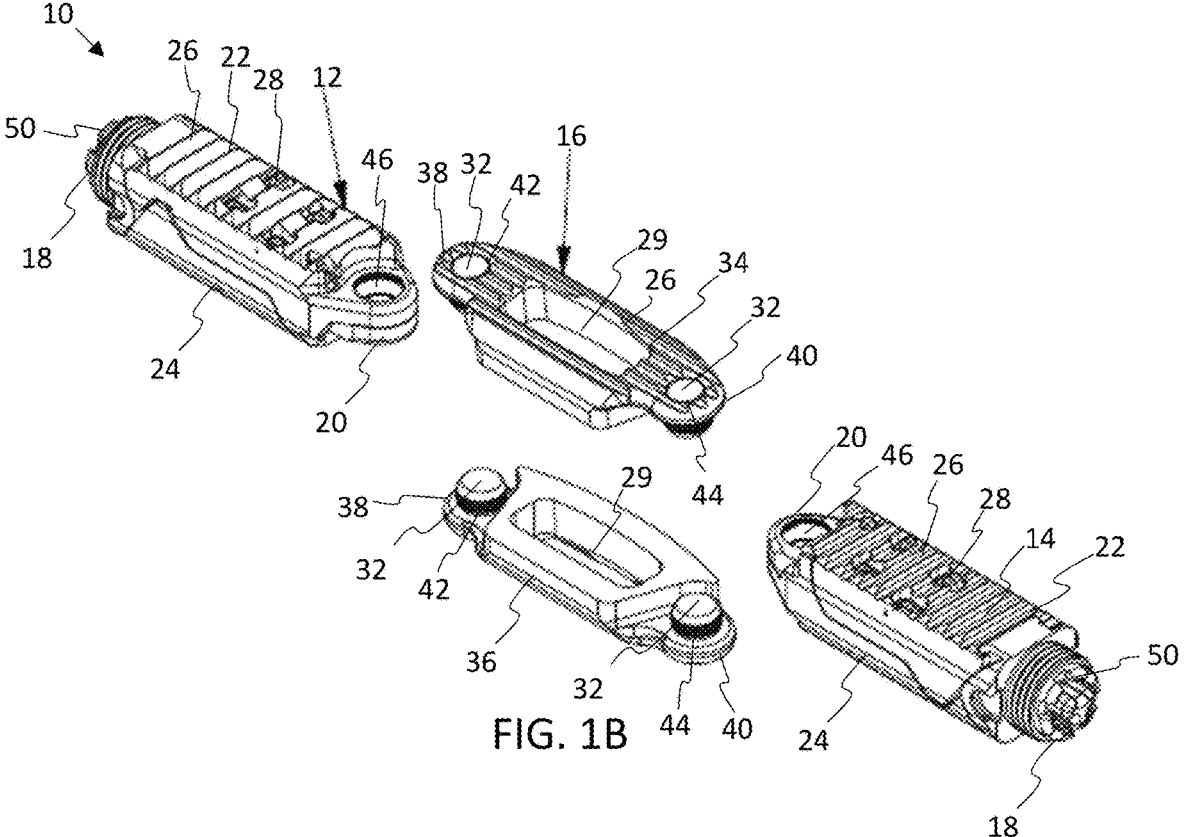
Figures 2A, 2B:
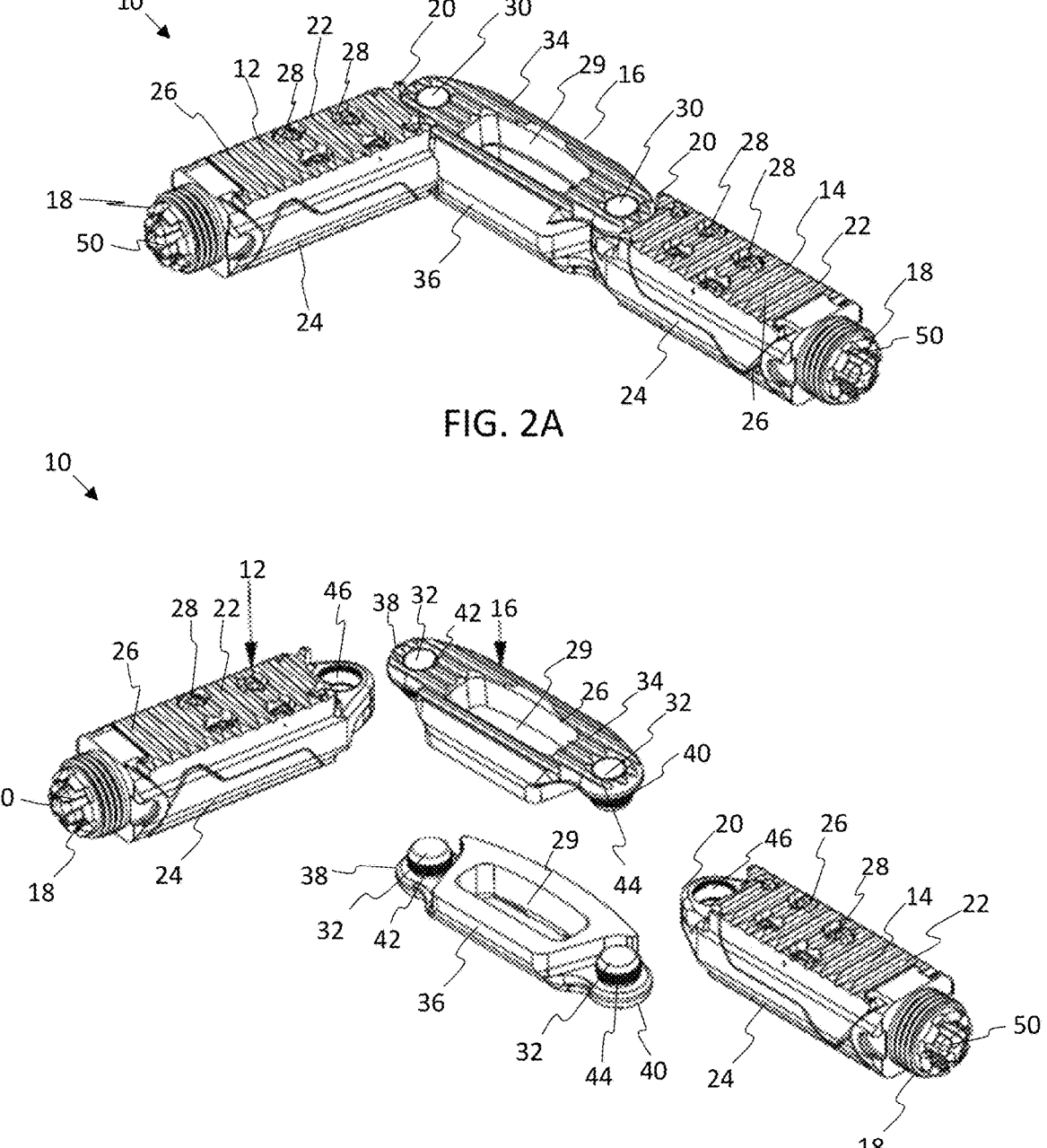
FIGS. 2A-2E show perspective, exploded, top, cross-sectional, and side views, respectively, of the expandable fusion device of FIGS. 1A-1E with a first lateral leg hinged at an angle with respect to link plates joining the two lateral legs.
Figure 2C:
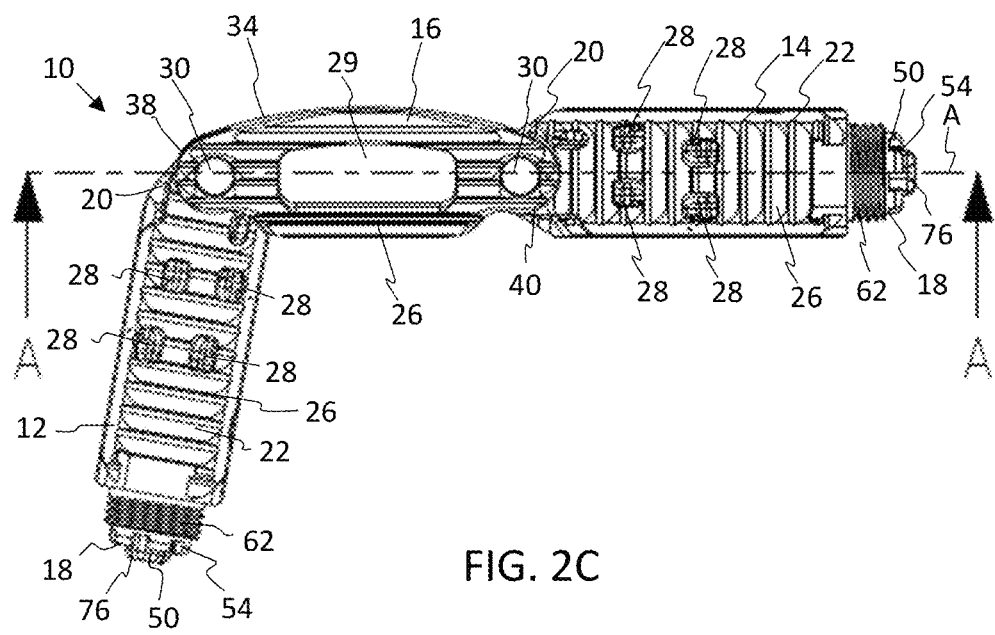
Figure 2D:
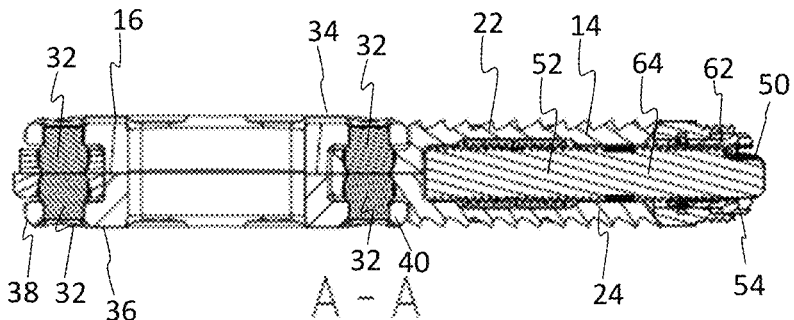
Figure 2E:
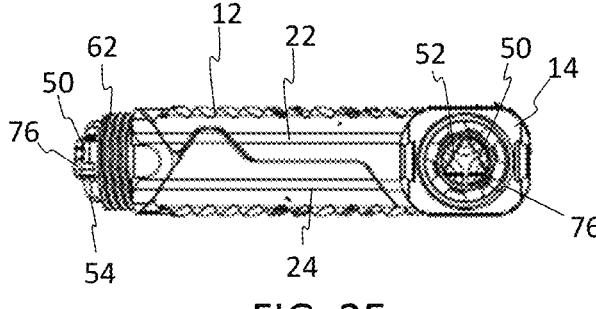
Figure 3A:
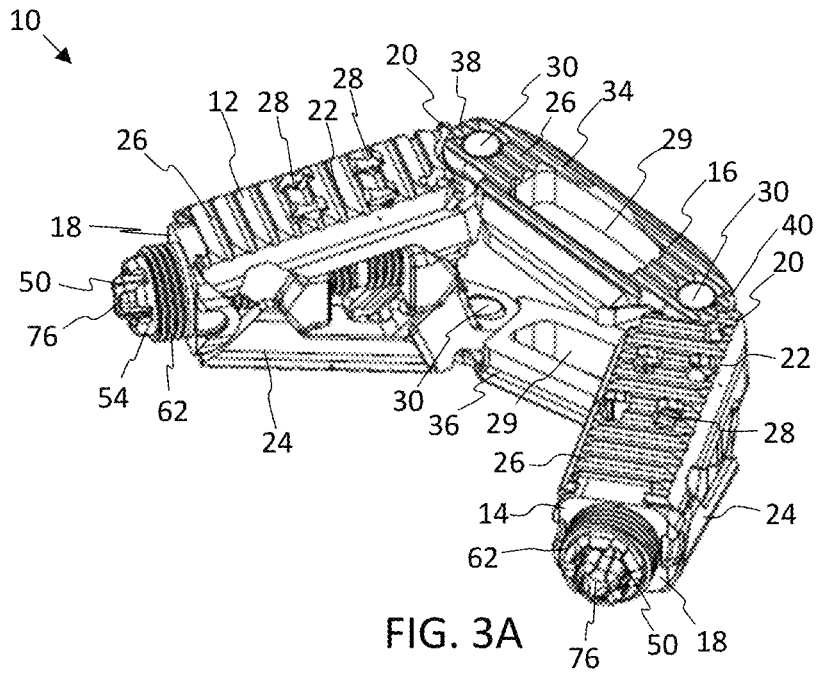
FIGS. 3A-3G show perspective, exploded, top, front, rear, and side views, respectively, of the expandable fusion device of FIGS. 2A-2E with both lateral legs hinged with respect to the link plates and the lateral legs are non-uniformly expanded in height.
Figure 3B:
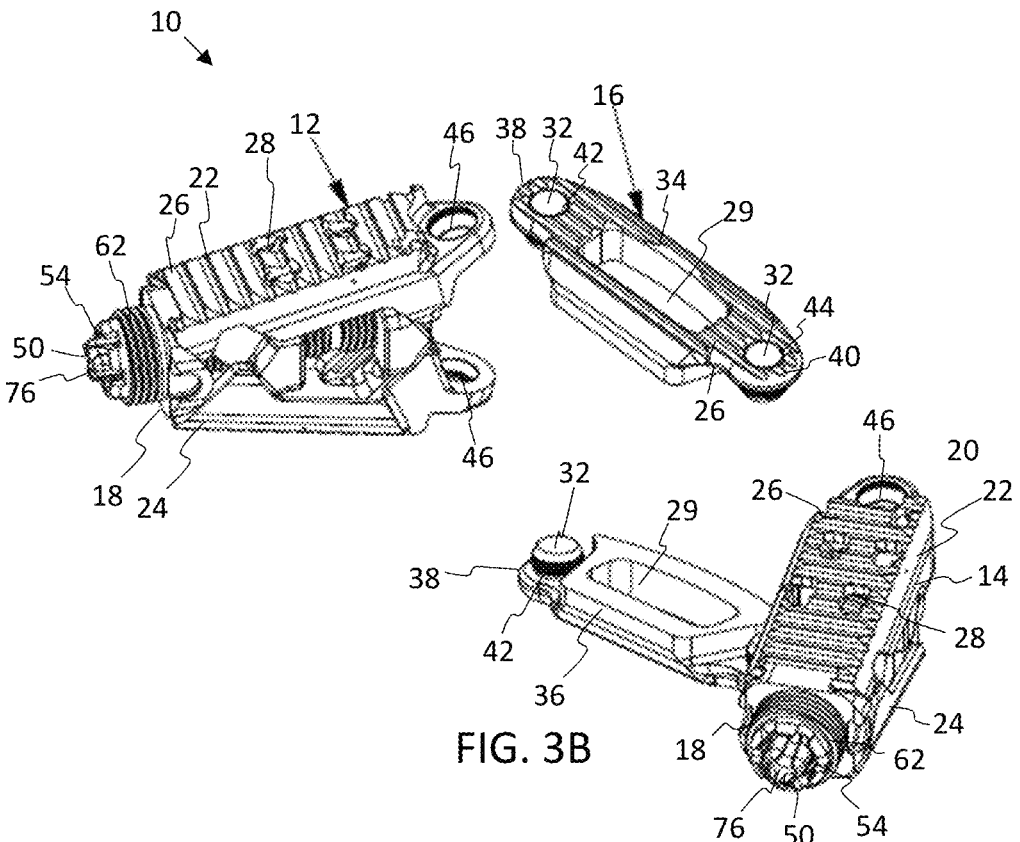
Figure 3C:
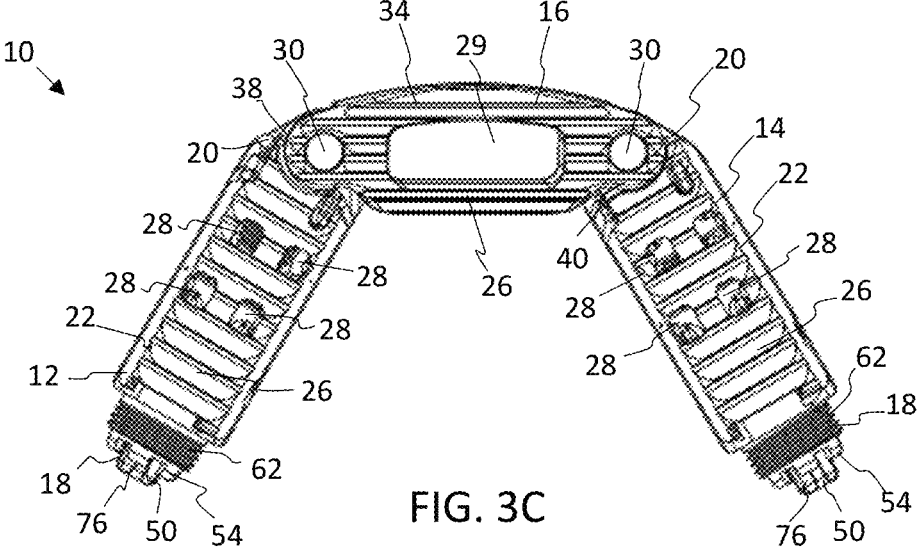
Figure 3D:
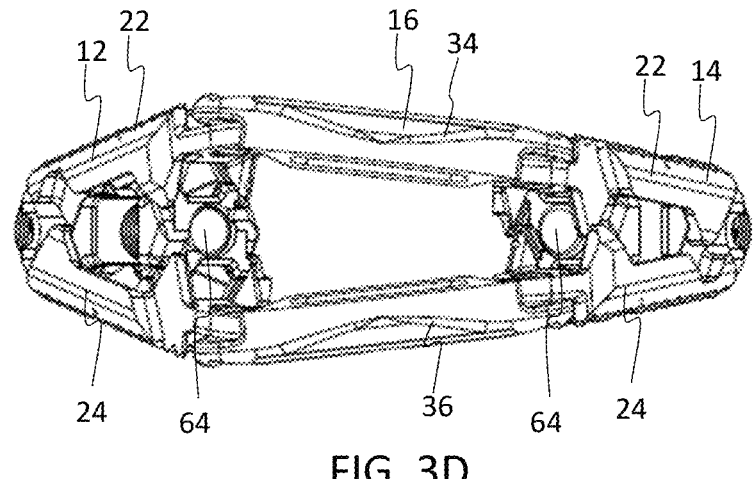
Figure 3E:
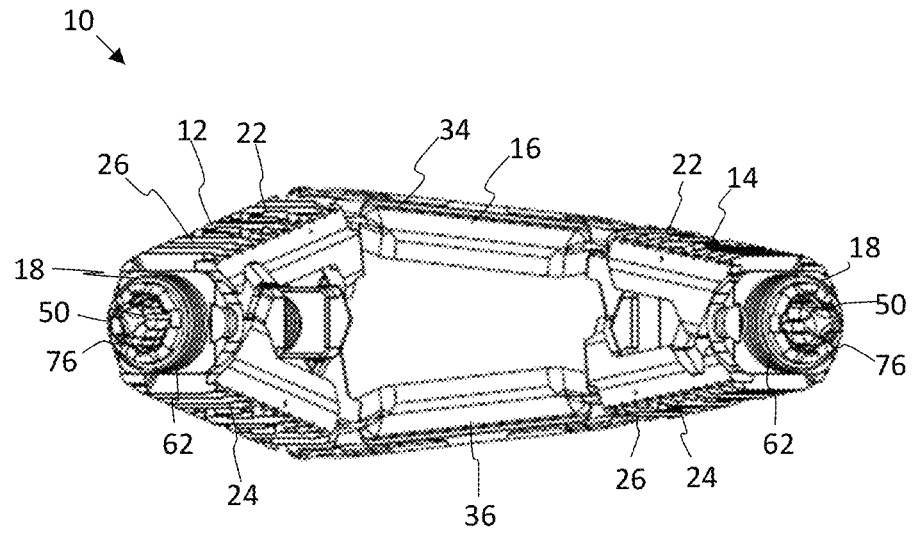
Figures 3F, 3G:
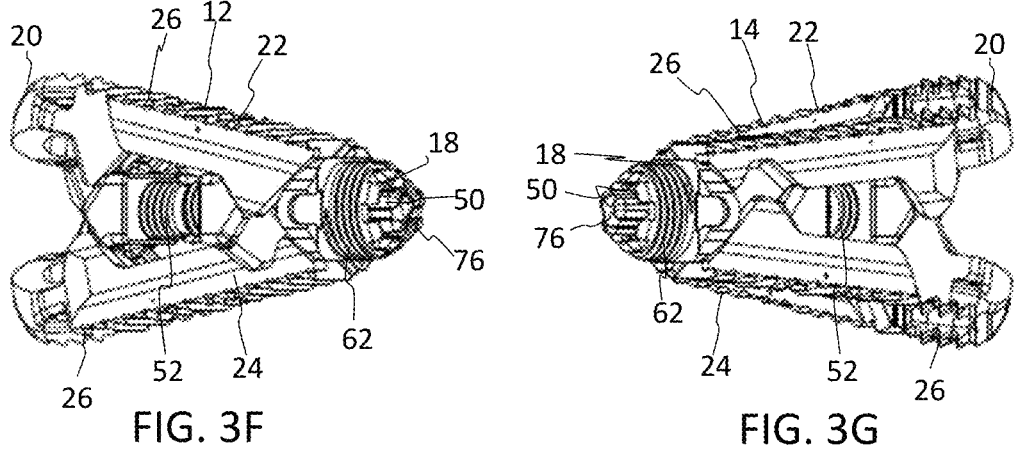
Figures 4A, 4B:
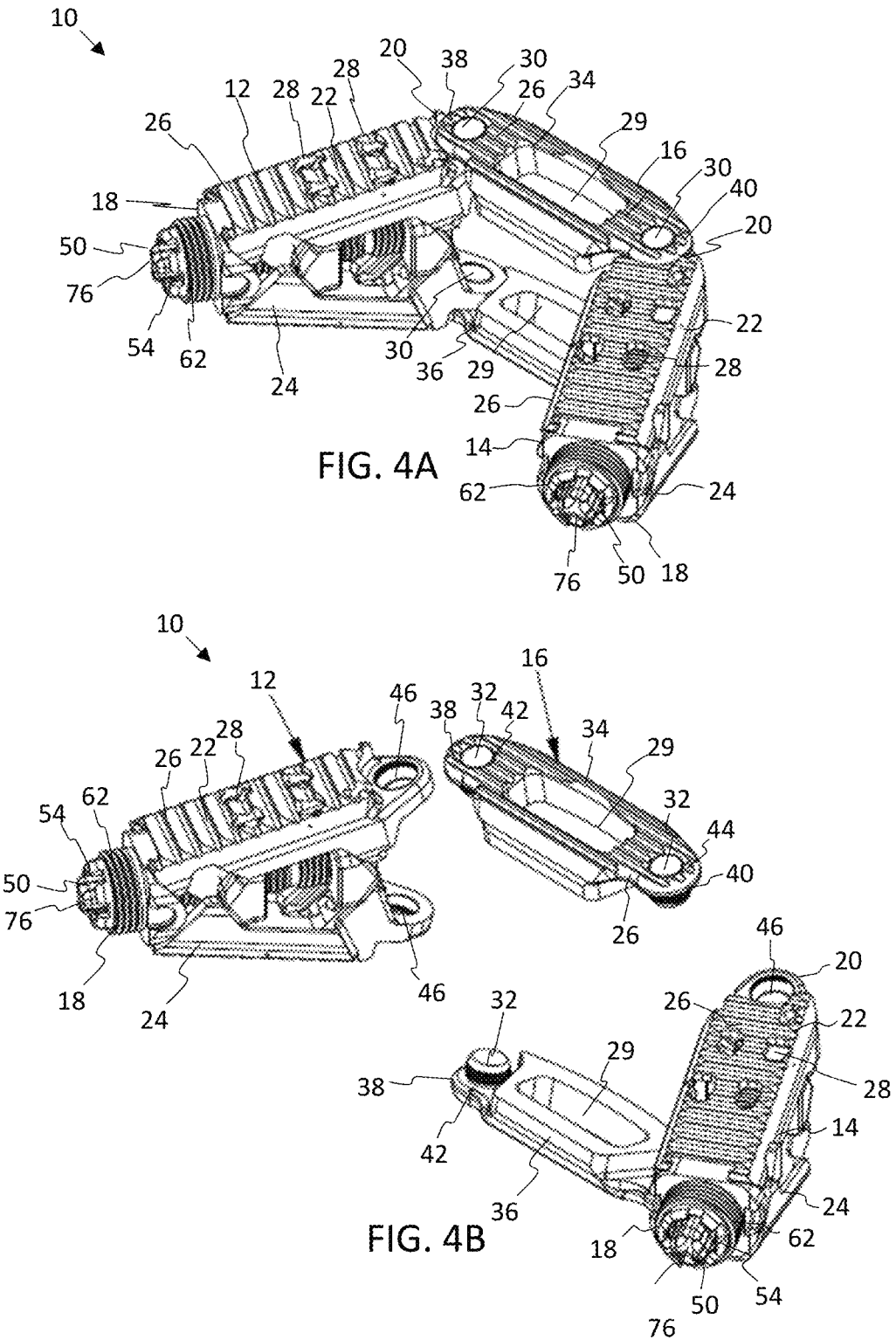
FIGS. 4A-4F show perspective, exploded, top, front, rear, and side views, respectively, of the expandable fusion device of FIGS. 3A-3G uniformly expanded in height.
Figure 4C:
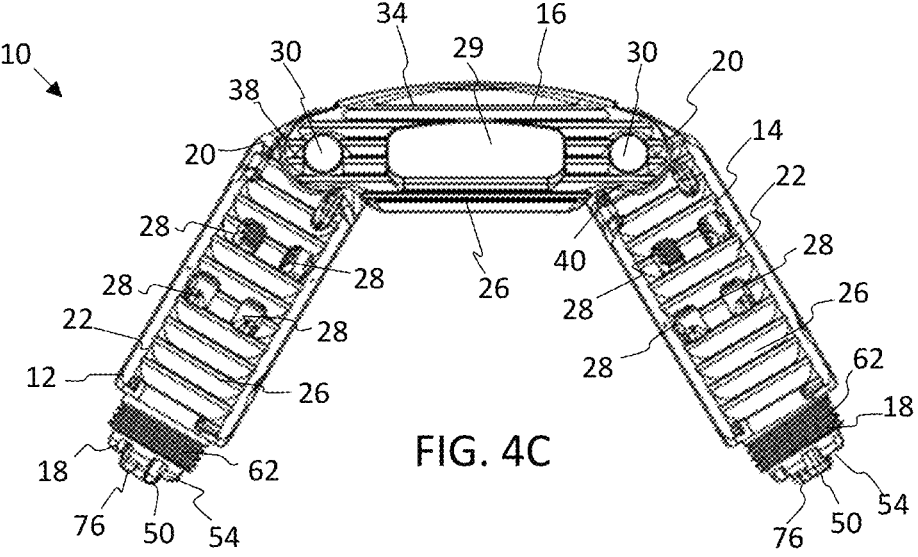
Figure 4D:
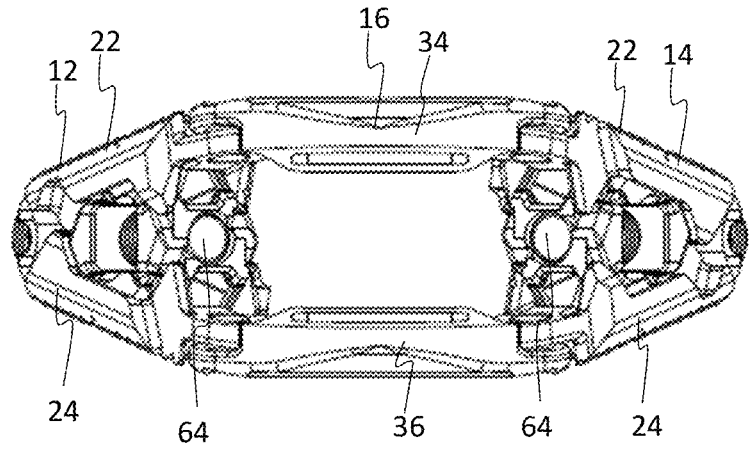
Figure 4E:
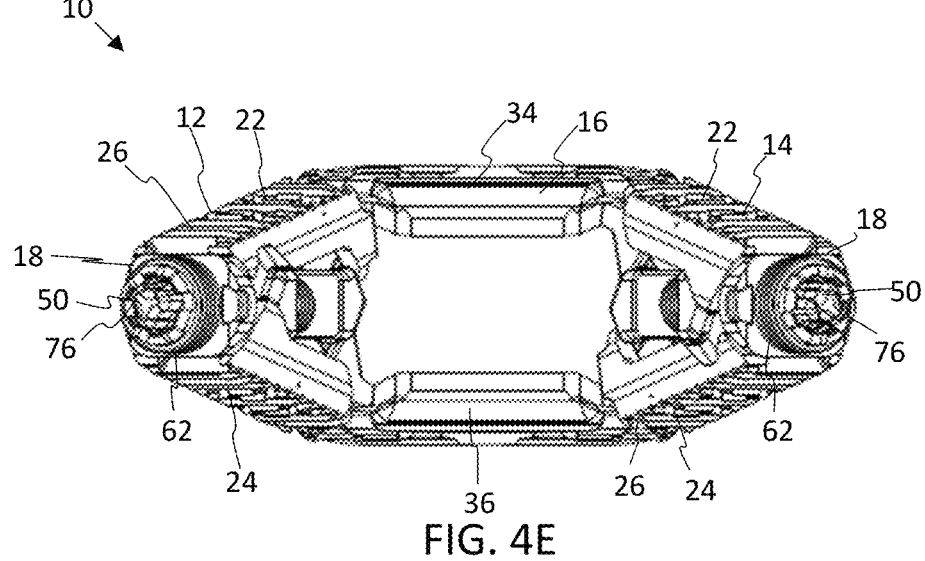
Figure 4F:
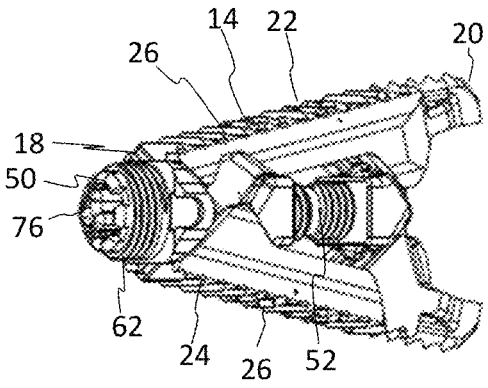
Figures 5A, 5B:
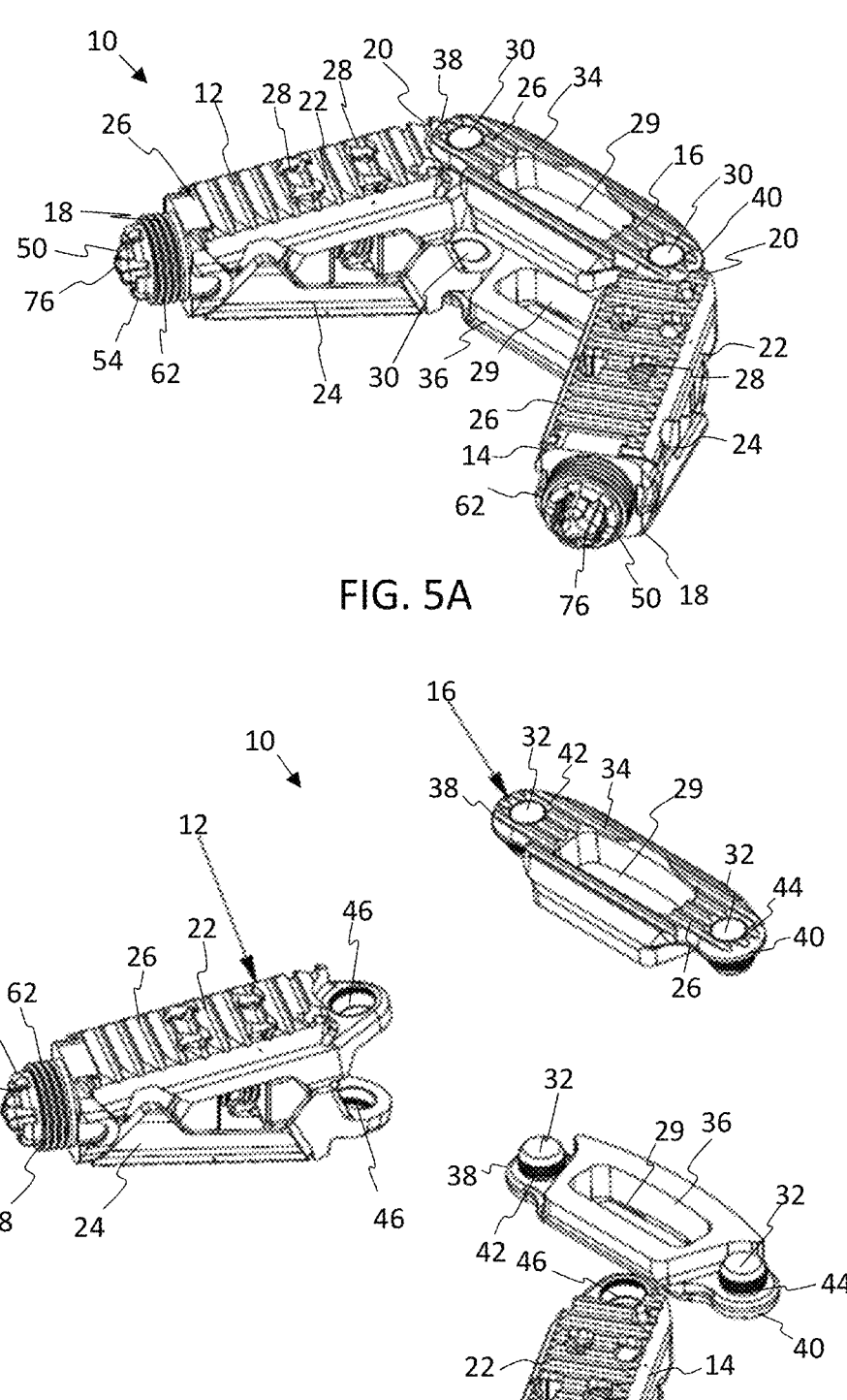
FIGS. 5A-5E show perspective, exploded, top, rear, and side views, respectively, of the expandable fusion device of FIGS. 4A-4F uniformly expanded in height.
Figure 5C:
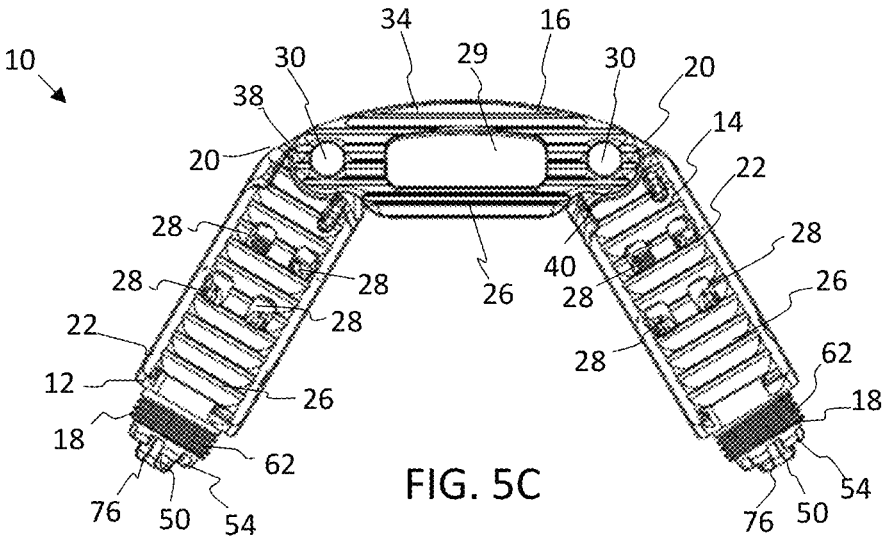
Figure 5D:
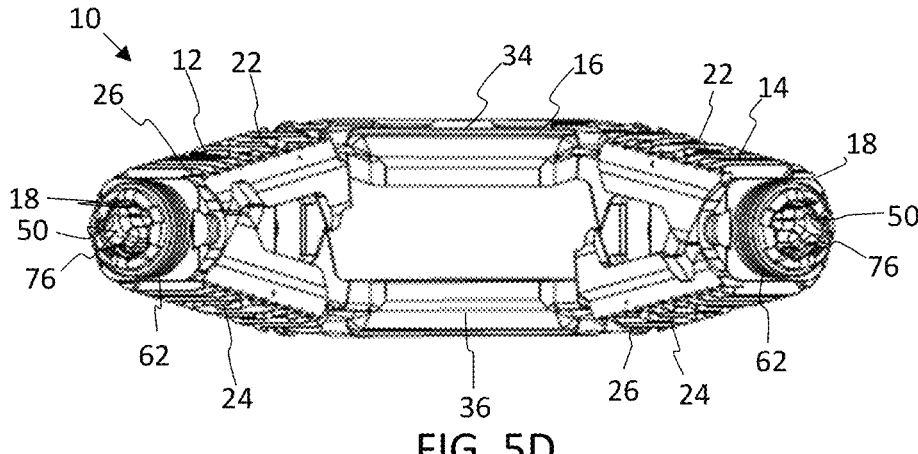
Figure 5E:
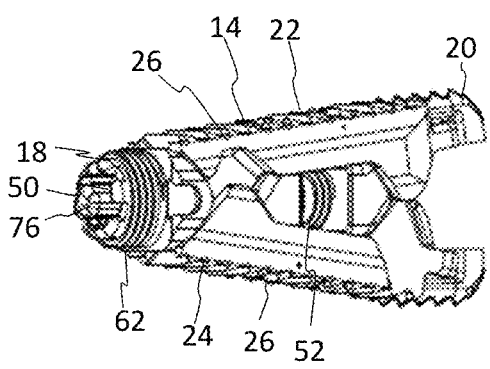

In order to improve the access profile of the interbody while maximizing cortical bone contact surface area, the interbody implant may be positioned within the disc space in a linear configuration, articulated into a widened configuration to increase surface area contact, and expanded in height to restore anatomical spinal alignment. While expanding in height, the respective heights of the lateral legs may be individually adjusted. The anterior side of the implant may be adjusted in height relative to the posterior side, thereby changing the lordotic angle. Expanding one side of the implant differently than the other will also allow for coronal adjustments. Accordingly, embodiments of the present application are generally directed to devices, systems, and methods for installing, articulating, and expanding the interbody implant. The terms implant, interbody, interbody implant, fusion device, spacer, cage, and expandable device may be used interchangeably herein.

Referring now to FIGS. 1A-1E, an articulating expandable fusion device or implant 10 is shown. The implant 10 may include three or more sections or legs, which are configured to articulate or pivot relative to one another to increase the overall width or footprint of the implant 10. The implant 10 may include a first expandable lateral leg 12, a second expandable lateral leg 14, and a third central leg with one or more link plates 16, which connect the first and second lateral legs 12, 14. When the first and/or second lateral legs 12, 14 are independently expanded in the height, the attached link plate or plates 16 are configured to passively increased in height, thereby providing lordotic and/or coronal adjustments.

The expandable lateral legs 12, 14 will be described with reference to the first lateral leg 12. It will be appreciated that the second lateral leg 14 is identical, or a mirror image, of the first lateral leg 12. The lateral leg 12 may extend from a rear end or proximal end 18 to a front end or distal end 20. It will be appreciated that when the legs 12, 14 and link plates 16 are aligned as shown in FIGS. 1A-1E, the front ends 20 of the lateral legs 12, 14 may face toward one another, but when the lateral legs 12, 14 are articulated relative to the link plates 16 as shown in FIGS. 3A-3E, the front ends 20 may face toward the anterior of the spine and the rear ends 18 may face toward the posterior of the spine.

The lateral leg 12, 14 includes a first or upper endplate 22 and a second or lower endplate 24 configured to engage adjacent vertebrae. The lateral leg 12, 14 is connected to one or more link plates 16, and the lateral leg 12, 14 is configured to articulate relative to the link plate 16 about one or more pivot or spherical joints 30. The spherical joint 30 may allow for free rotation in two planes at the same time while preventing translation. The spherical joint 30 may be a revolute joint such as a ball joint, pin joint, or hinge joint.

The lateral legs 12, 14 and link plates 16 may be able to rotate freely about each respective pin 32. The pin 32 may include a cylinder portion, spheroidal portion, oval portion, and/or other curved shape portion. A portion of the pin 32 may be positioned within a portion of endplate 22, 24 and an opposite portion of the pin 32 may be positioned within the link plate 34, 36. A portion of the pin 32 may be affixed to one of the endplate 22, 24 and/or the link plate 34, 36, for example by a press fit, interference fit, adhesive, or other fastening method, and the opposite portion may remain movable with respect to the socket of the other endplate 22, 24 and/or link plate 34, 36. This may enable the endplate 22, 24 to hingedly connect to the link plate 34, 36 and for these hinged elements to be movable with respect to each other along more than one axis. Other hinge types may also be used, such as a living hinge or piano hinge, as nonlimiting examples.

Although spherical joints 30 are exemplified herein, it will be appreciated that other joint geometries may be used. The spherical joints 30 may allow for differential adjustment of the expandable legs 12, 14 during expansion or in the final construct as the surgeon intends. The spherical joints 30 may account for different insertion angles of the legs 12, 14 relative to each other, without locking the implant 10 into a forced shape and/or allowing for anatomical variations.

The one or more link plates 16 may include a first or upper link plate 34 and a second or lower link plate 36 configured to engage adjacent vertebrae. It will be appreciated that the lower link plate 36 is identical, or a mirror image, of the upper link plate 34. The link plate 34 extends from a first end 38 to a second end 40. The first end 38 of the link plate 34 includes a first opening 42 configured to receive a first portion of a first pin 32 and the second end 40 of the link plate 34 includes a second opening 44 configured to receive a first portion of a second pin 32. Similarly, the distal ends 20 of the upper endplates 22 of the respective first and second legs 12, 14 each include an opening 46 configured to receive second portions of the first and second pins 32, respectively. In this manner, the upper endplate 22 of the first leg 12 is pivotally connected to the first end 38 of the upper link plate 34 and the upper endplate 22 of the second leg 14 is pivotally connected to the second end 40 of the upper link plate 34.

Similarly, the first end 38 of the lower link plate 36 includes a first opening 42 configured to receive a first portion of a third pin 32 and the second end 40 of the lower link plate 36 includes a second opening 44 configured to receive a first portion of a fourth pin 32. Likewise, the distal ends 20 of the lower endplates 24 of the respective first and second legs 12, 14 each include an opening 46 configured to receive second portions of the third and fourth pins 32, respectively. In this manner, the lower endplate 24 of the first leg 12 is pivotally connected to the first end 38 of the lower link plate 36 and the lower endplate 24 of the second leg 14 is pivotally connected to the second end 40 of the lower link plate 36.

One or more of the endplates 22, 24 and/or link plates 34, 36 may include a plurality of teeth 26, protrusions, or other friction enhancing surfaces configured to engage bone. The endplates 22, 24 may include one or more graft openings or windows 28 and the link plates 34, 36 may include a large central graft retaining opening or window 29 configured to receive bone graft or other suitable bone growth enhancing material.

In the linear configuration shown in FIGS. 1A-1E, the implant 10 is configured to be deployed through a guide tube or cannula in a fully collapsed orientation into a disc space between adjacent vertebral bodies. The cannula may be suitable for use during a minimally invasive surgical (MIS) procedure, for example. The disc space may be accessed through a posterior approach. The cannula may be docked on the disc space through Kambin's triangle, or the anatomical area that is bordered by the disc space, exiting nerve root, and traversing nerve root. The lateral legs 12, 14 and link plates 16 may be aligned along a central longitudinal axis A such that the implant 10 may be deployed through the cannula. In FIGS. 2A-2E, while still in the collapsed position, the first lateral leg 12 is articulated relative to the links plates 16 and second lateral leg 14.

In FIGS. 3A-3G, the second lateral leg 14 is articulated relative to the link plates 16 such that the two lateral legs 12, 14 are bent or angled relative to the central link plates 16 to form a widened U-shape configuration. The lateral legs 12, 14 are also non-uniformly expanded in height, thereby passively expanding the first end 38 of the link plates 34, 36 to a greater height than the second end 40 of the link plates 34, 36. In FIGS. 4A-4F, the first and second lateral legs 12, 14 are uniformly expanded in height such that the height of the upper and lower link plates 34, 36 are substantially parallel. In FIGS. 5A-5E, a smaller degree of expansion is shown for the first and second lateral legs 12, 14, with generally parallel upper and lower link plates 34, 36. Adjusting the heights of the anterior ends (e.g., front end 20) relative to the posterior ends (e.g., rear end 18) of the lateral legs 12, 14 may adjust the lordotic angle. Expanding the lateral legs 12, 14 differently than one another may allow for coronal adjustment. The surgeon may select the amount and degree of adjustment based on the patient's anatomy and the desired surgical outcome.

Figure 6:
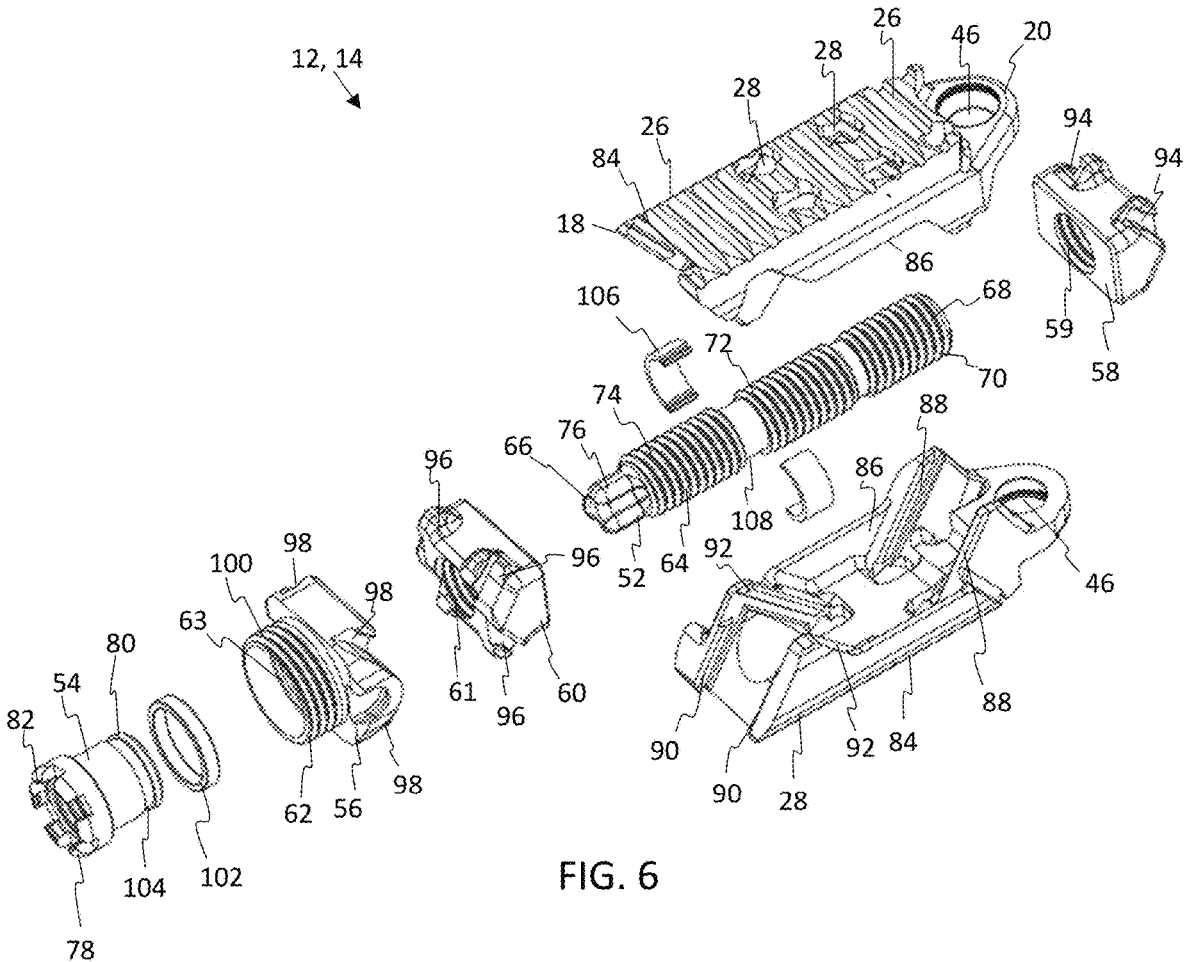
FIG. 6 is an exploded view of one of the expandable lateral legs according to one embodiment.

Turning now to FIG. 6, an exploded view of one of the lateral legs 12, 14 is shown. Each lateral leg 12, 14 includes an actuation assembly 50 including a drive screw or actuator 52 and a nut 54 configured to move a plurality of driving ramps 56, which expand the endplates 26, 28 in height. The plurality of driving ramps 56 may include a front ramp 58, a mid-ramp 60, and a rear ramp 62. The front ramp 58 may include a central longitudinal bore 59, the mid-ramp 60 may include a central longitudinal bore 61, and the rear ramp 62 may include a central longitudinal bore 63. The plurality of driving ramps 58, 60, 62 may be positioned along the length of the actuator 52 and are configured to engage and drive the upper and lower endplates 26, 28, respectively. When one or more of the driving ramps 58, 60, 62 are moved, they slide against the upper and lower endplates 26, 28, thereby providing for expansion of the leg 12, 14 in height. The expansion may include the ability to individually adjust the anterior and/or posterior heights of the lateral legs 12, 14.

Each of the lateral legs 12, 14 may include an actuation assembly 50 configured to independently expand the respective heights of the lateral legs 12, 14. The actuation assembly 50 includes a rotatable actuator 52 and rotatable nut 54 configured to move a plurality of internal ramps 56. Each lateral leg 12, 14 includes at least three driving ramps: front ramp 58, mid-ramp 60, and rear ramp 62, which interface with the actuator 52. The actuator 52 may include a shaft 64 extending from a proximal end 66 to a distal end 68. The shaft 64 may include a first threaded portion 70, a second threaded portion 72, and a third threaded portion 74. The second threaded portion 72 may be positioned between the first and third threaded portions 74. The threaded portions 70, 72, 74 may have the same or different attributes including outer diameters, handedness, thread form, thread angle, lead, pitch, etc.

Figures 7A, 7B, 7C, 7D:
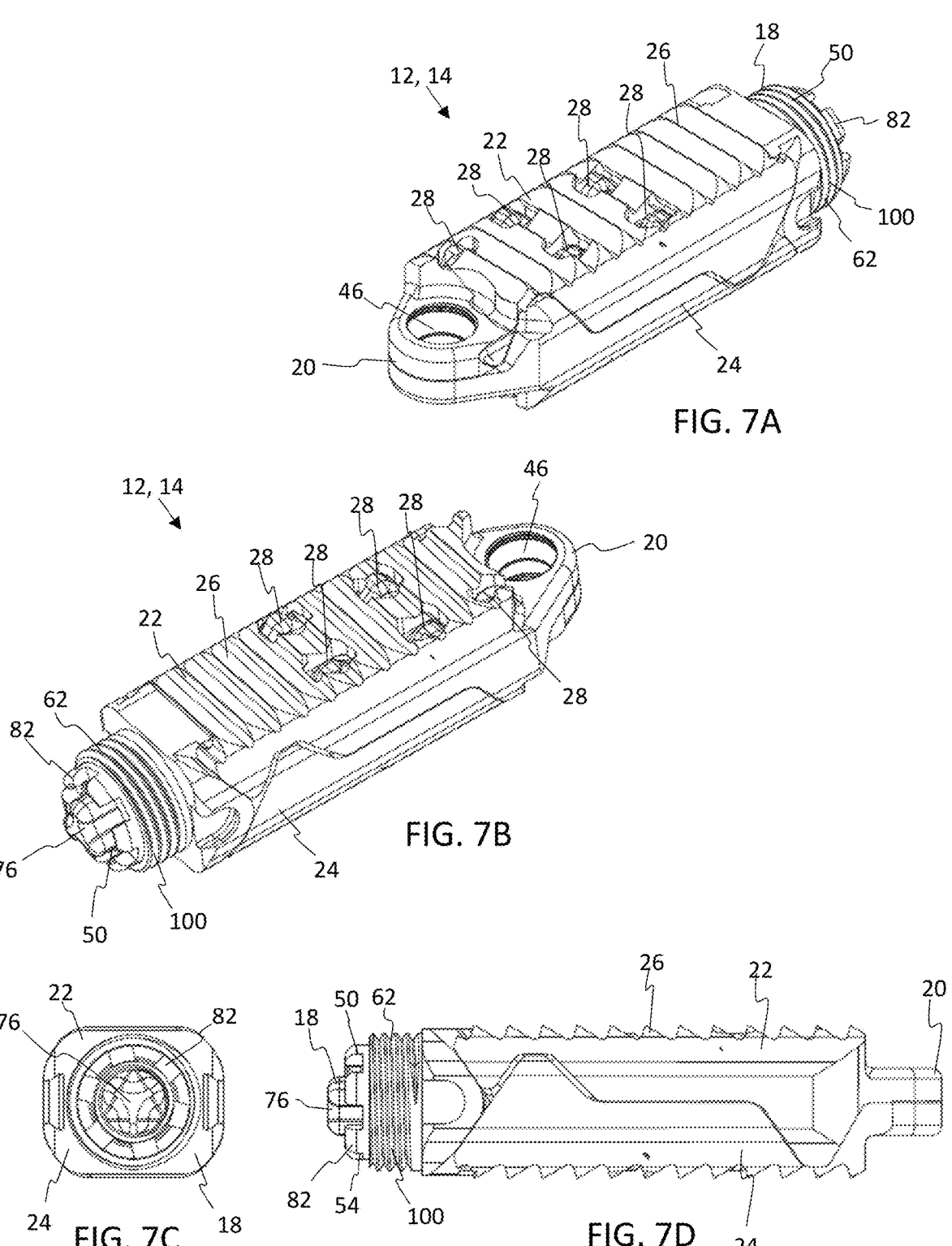
FIGS. 7A-7G show perspective, rear, side, top and cross-sectional views, respectively, of the lateral leg shown in FIG. 6 in a fully collapsed configuration.
Figure 7E:
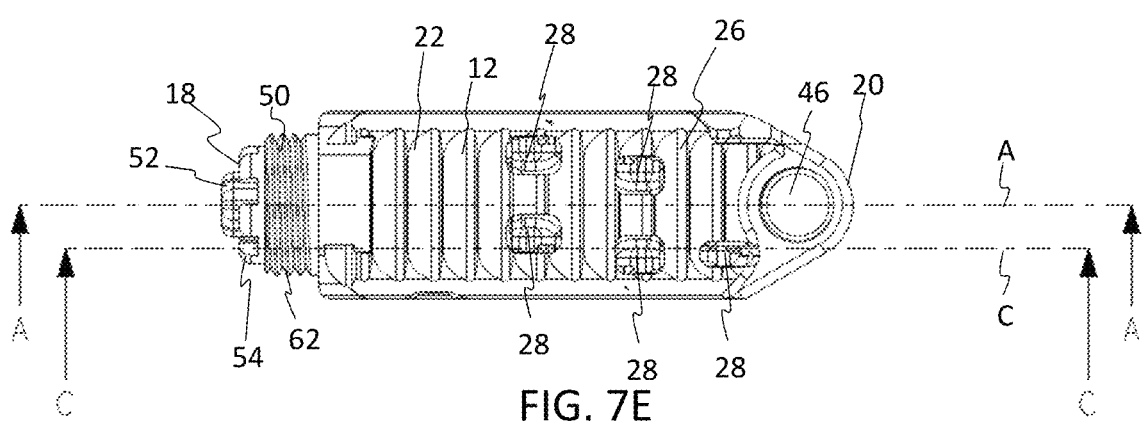
Figure 7F:
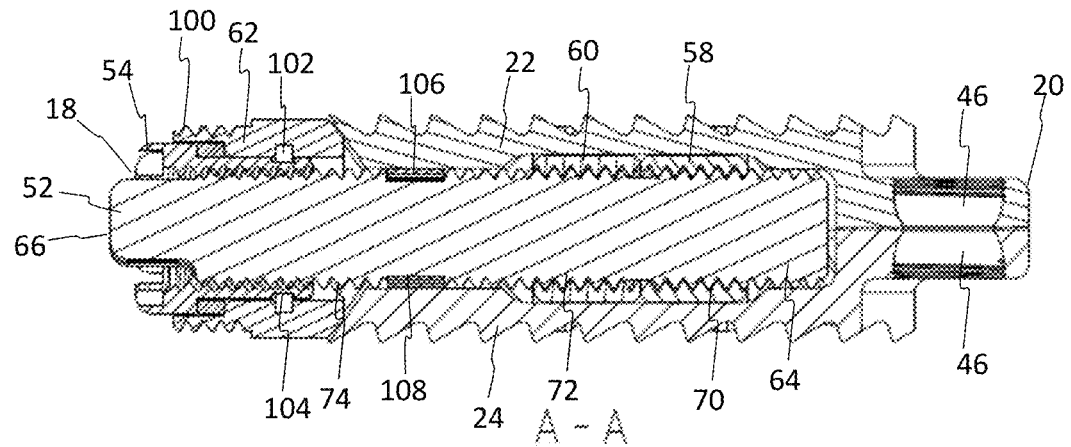
Figure 7G:
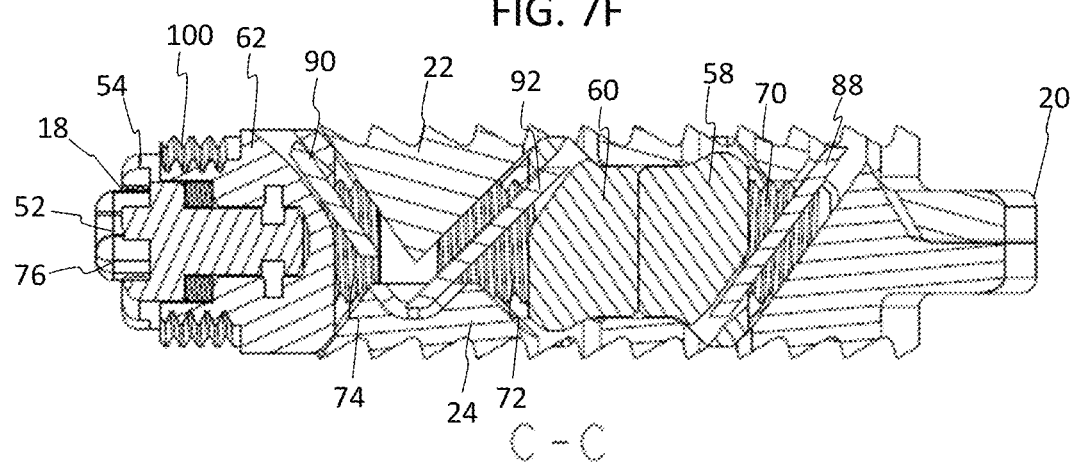
Figures 8A, 8B, 8C, 8D:
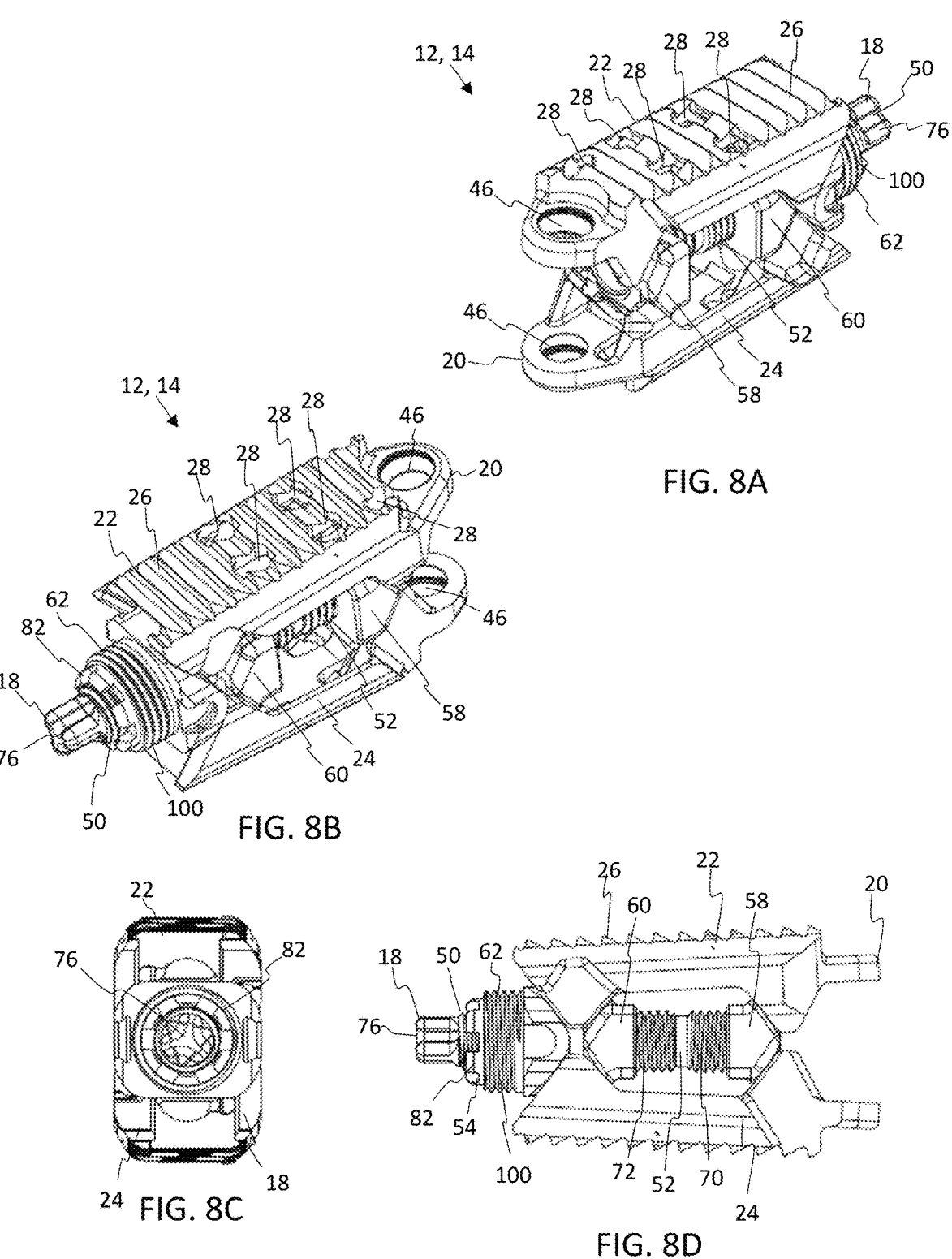
FIGS. 8A-8G show perspective, rear, side, top, and cross-sectional views, respectively, of the lateral leg shown in FIG. 6 in an expanded configuration.
Figures 8E, 8F, 8G:
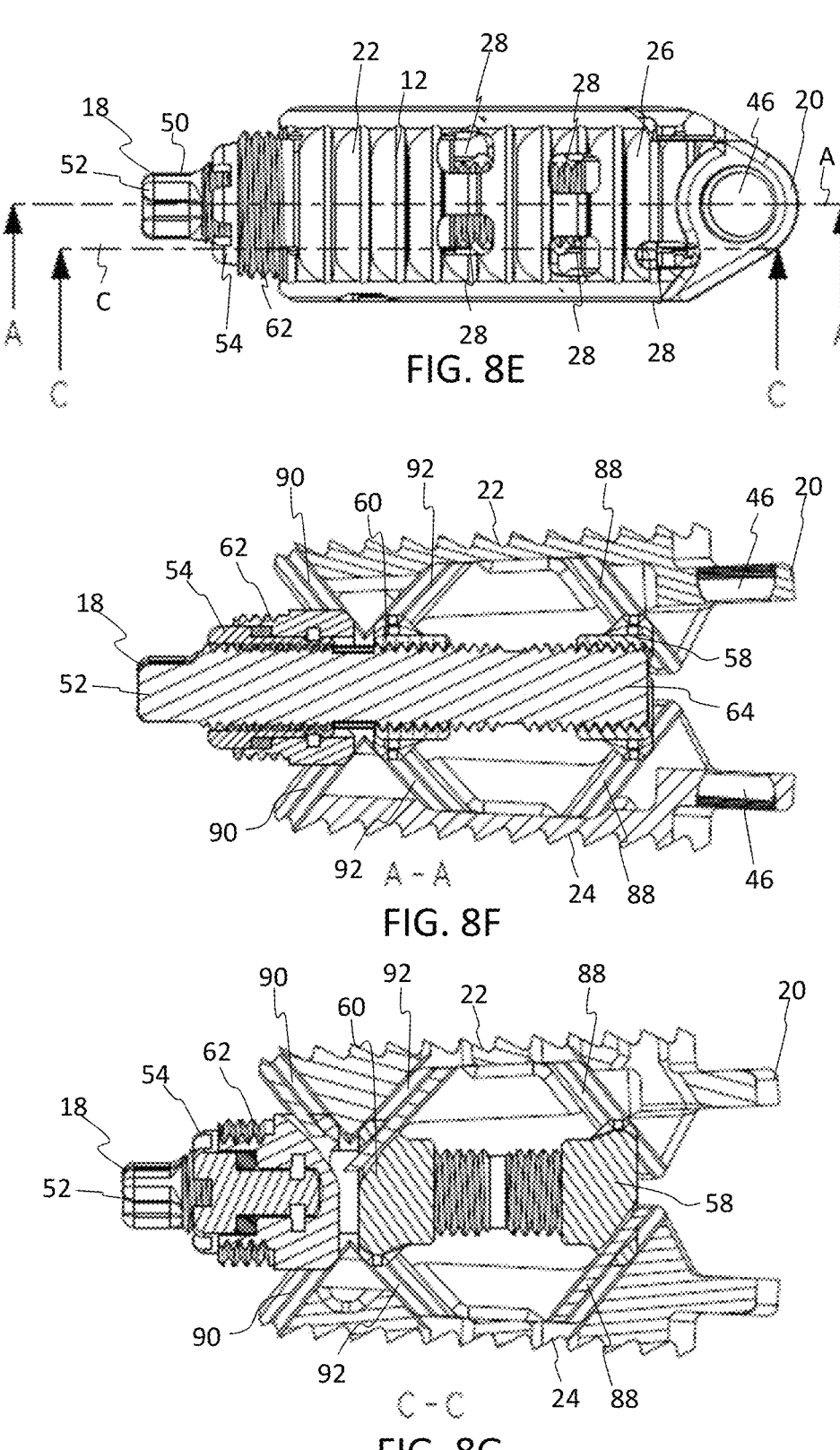
Figures 9A, 9B, 9C, 9D:
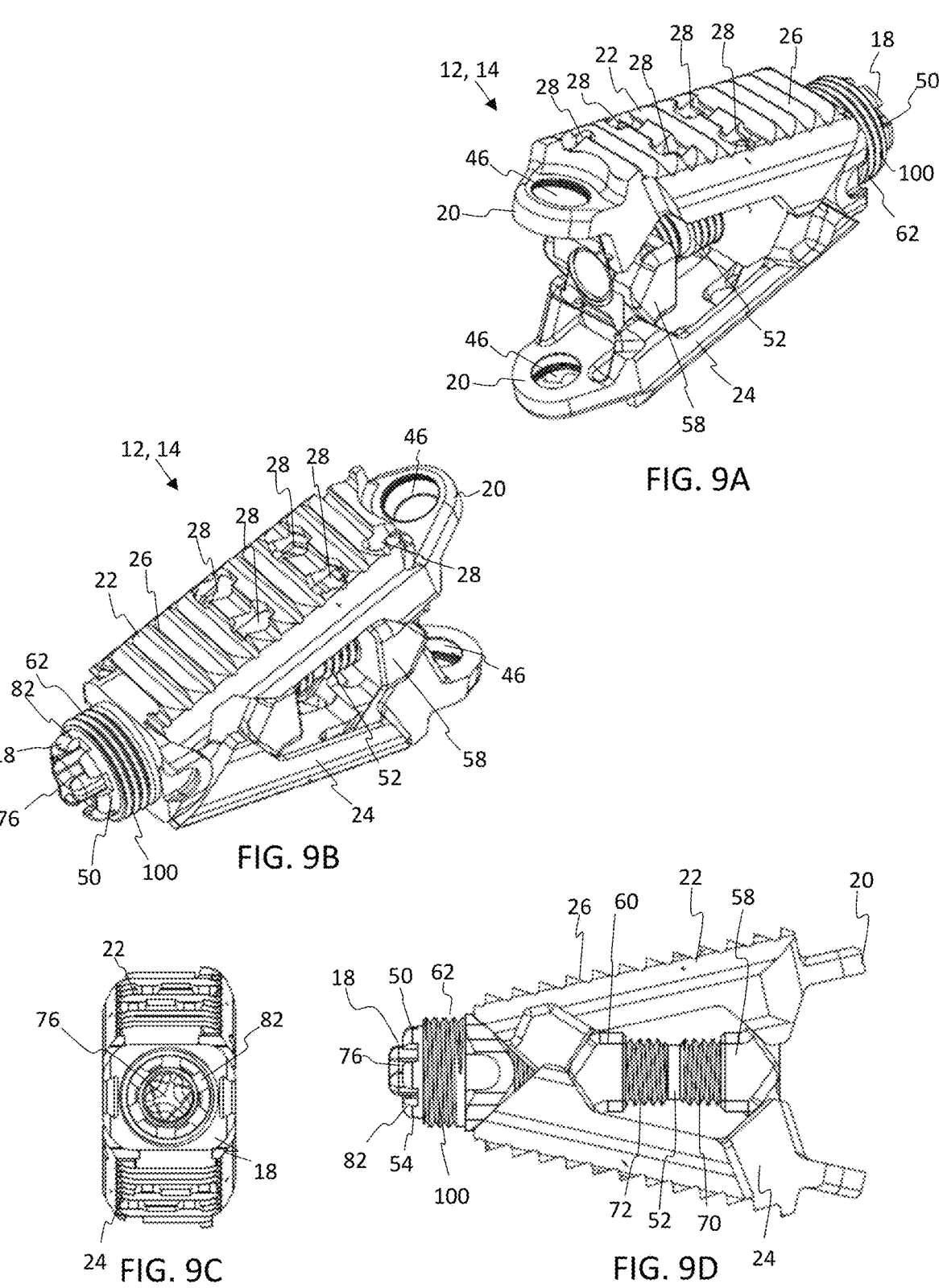
FIGS. 9A-9G show perspective, rear, side, top, and cross-sectional views, respectively, of the lateral leg shown in FIG. 6 in an expanded configuration with a greater anterior height.
Figures 9E, 9F, 9G:
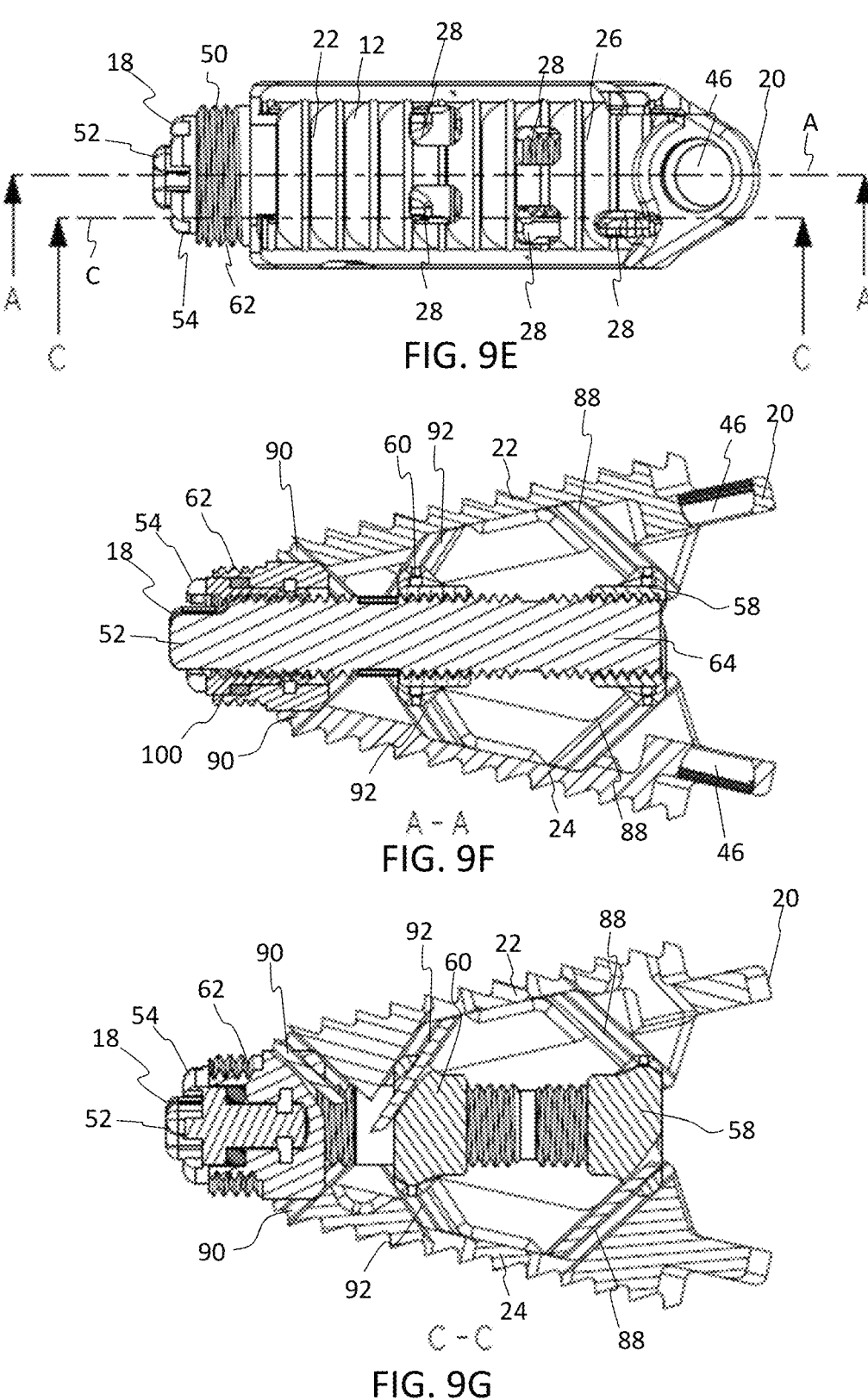
Figure 10:
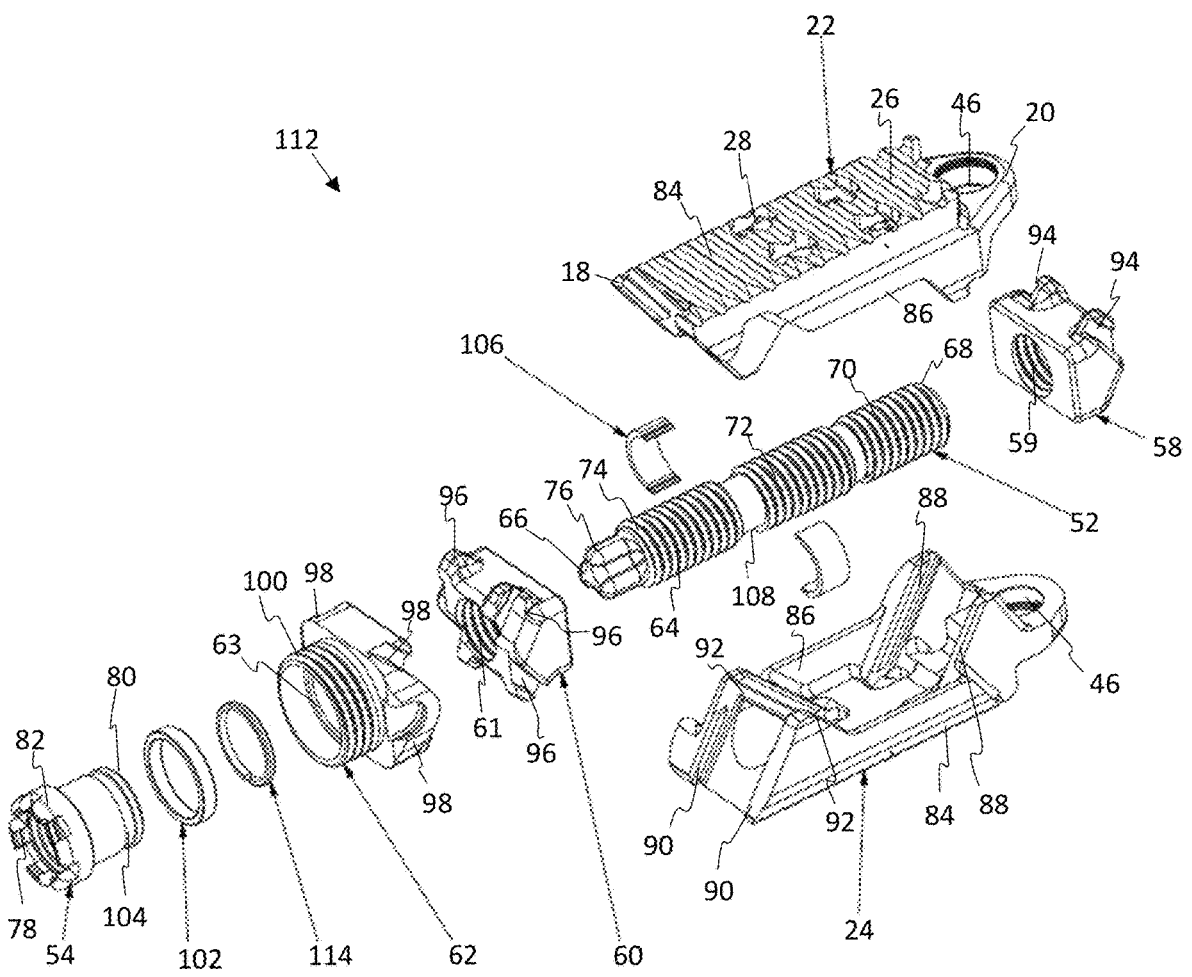
FIG. 10 is an exploded view of one of the expandable lateral legs according to another embodiment.
Figures 12A, 12B, 12C, 12D:
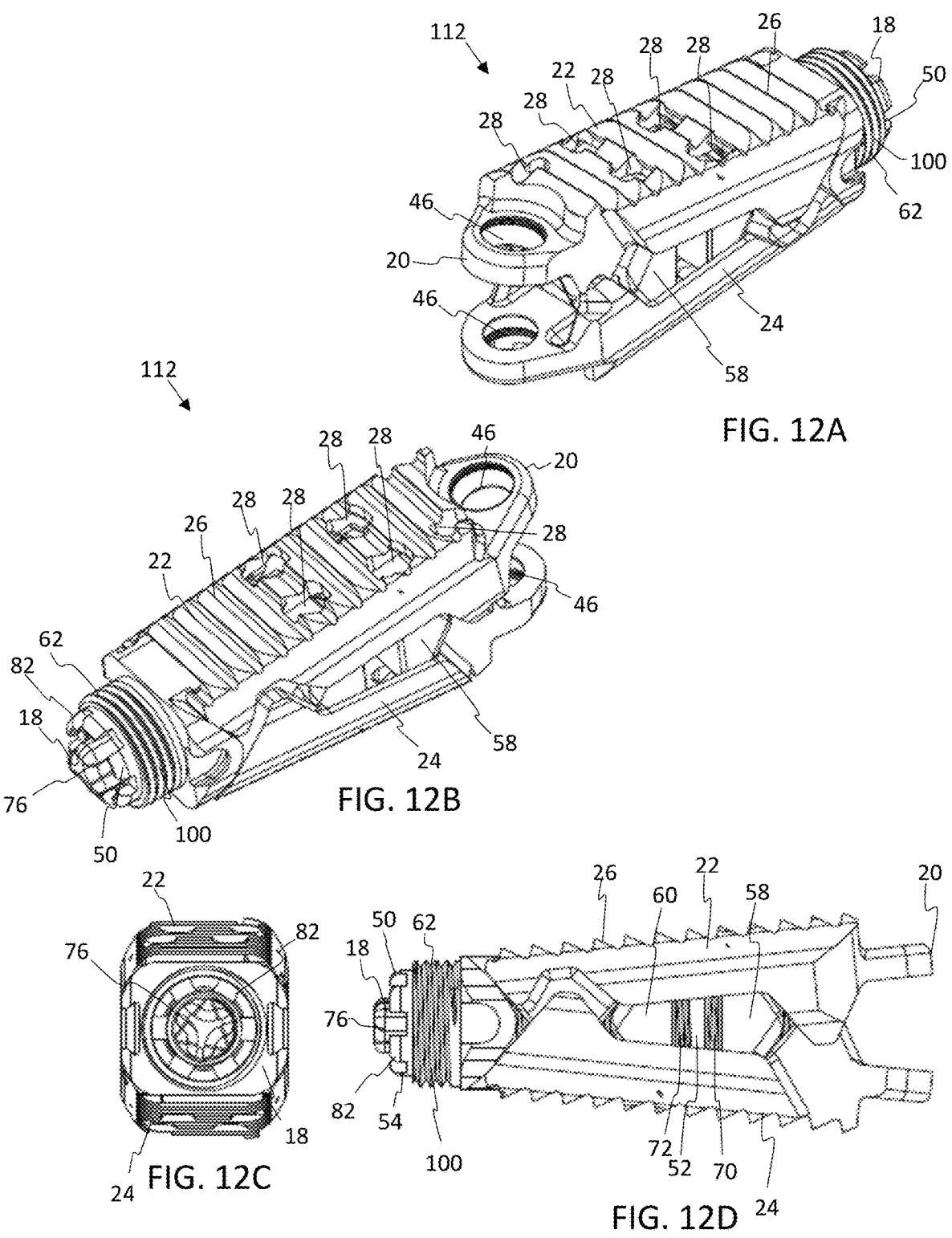
FIGS. 12A-12G show perspective, rear, side, top, and cross-sectional views, respectively, of the lateral leg shown in FIG. 10 in an expanded configuration.
Figure 12E:
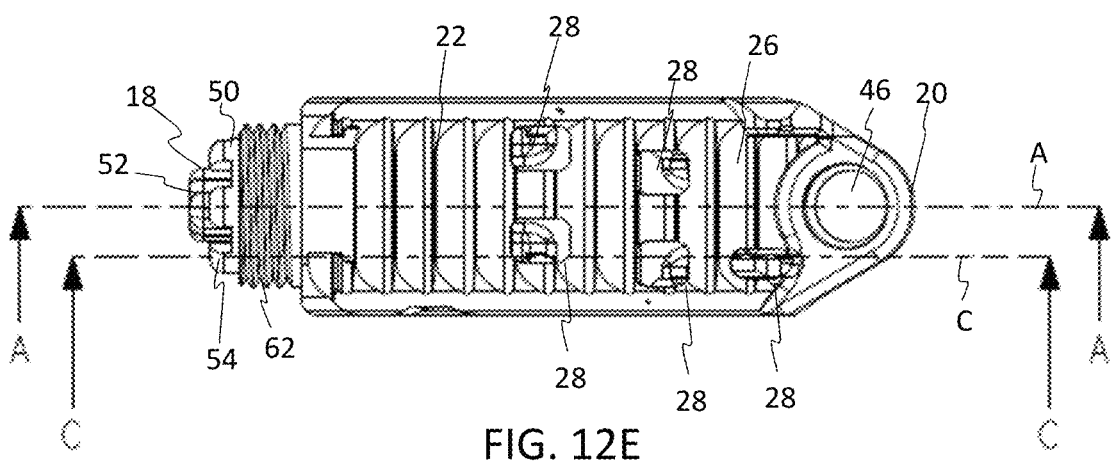
Figure 12F:
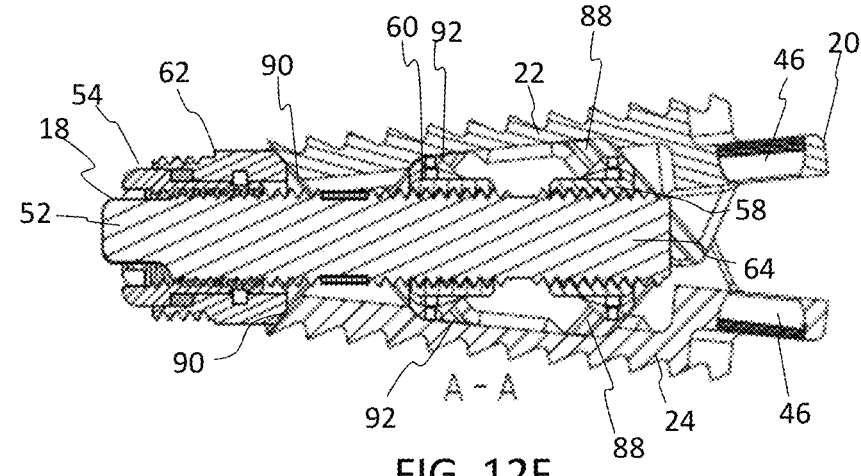
Figure 12G:
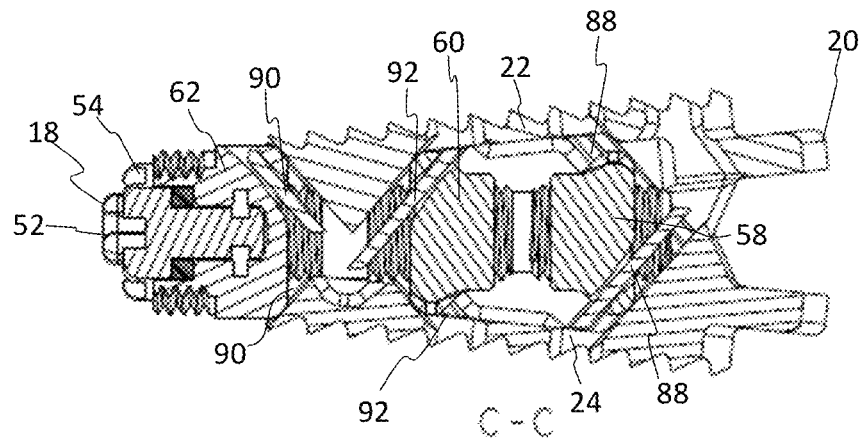
Figures 13A, 13B, 13C, 13D:
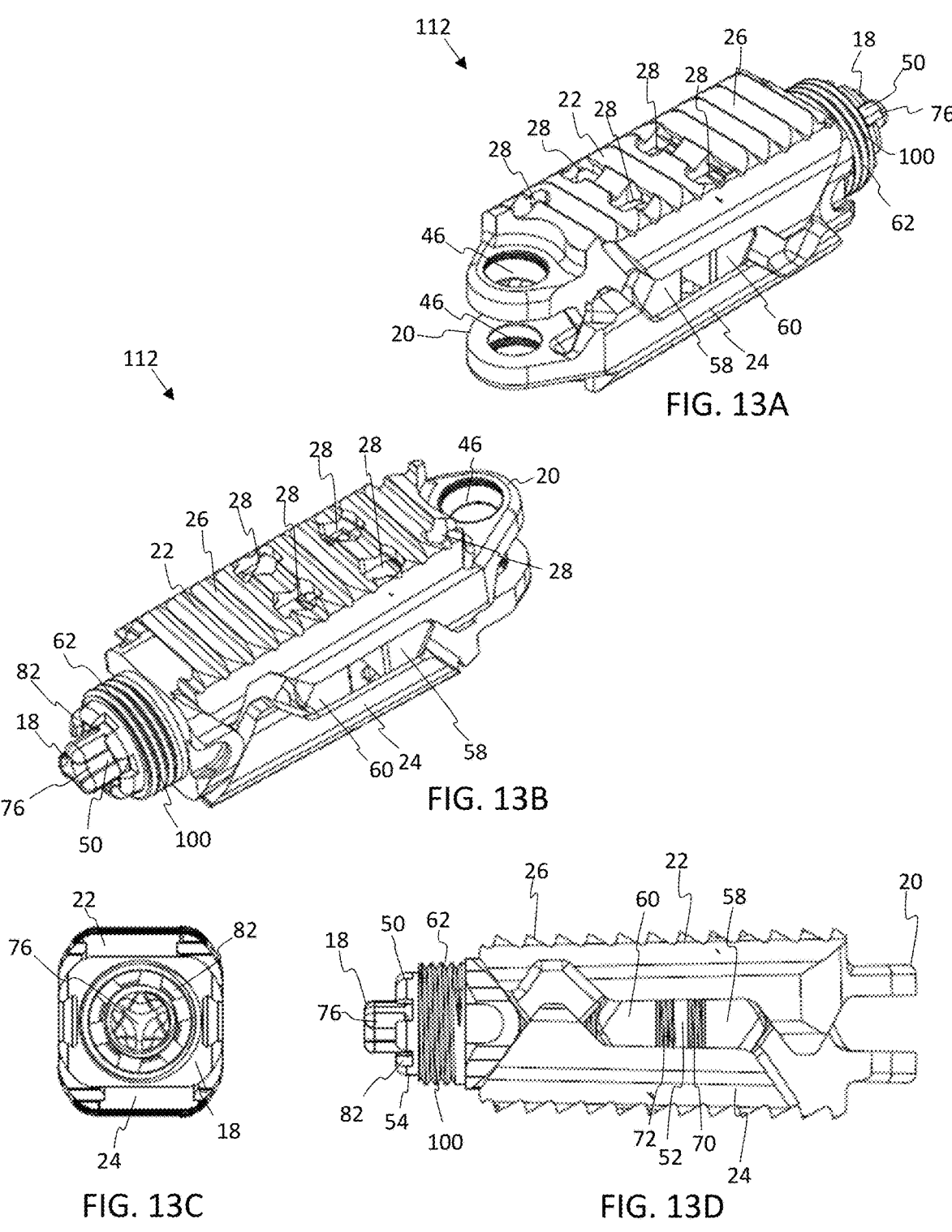
FIGS. 13A-13G show perspective, rear, side, top, and cross-sectional views, respectively, of the lateral leg shown in FIG. 10 in another expanded configuration.
Figures 13E, 13F, 13G:
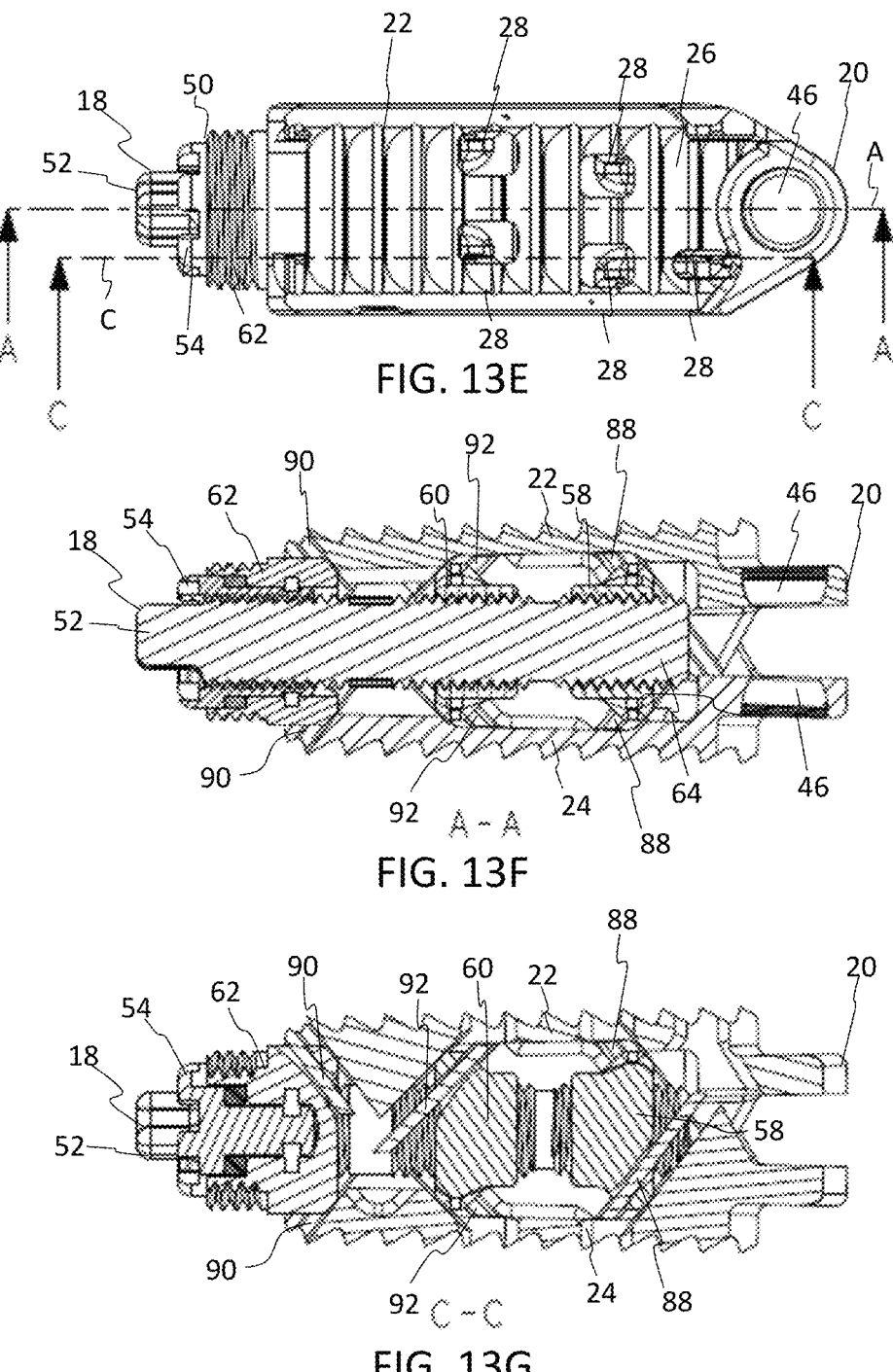
Figures 14A, 14B, 14C, 14D, 14E:
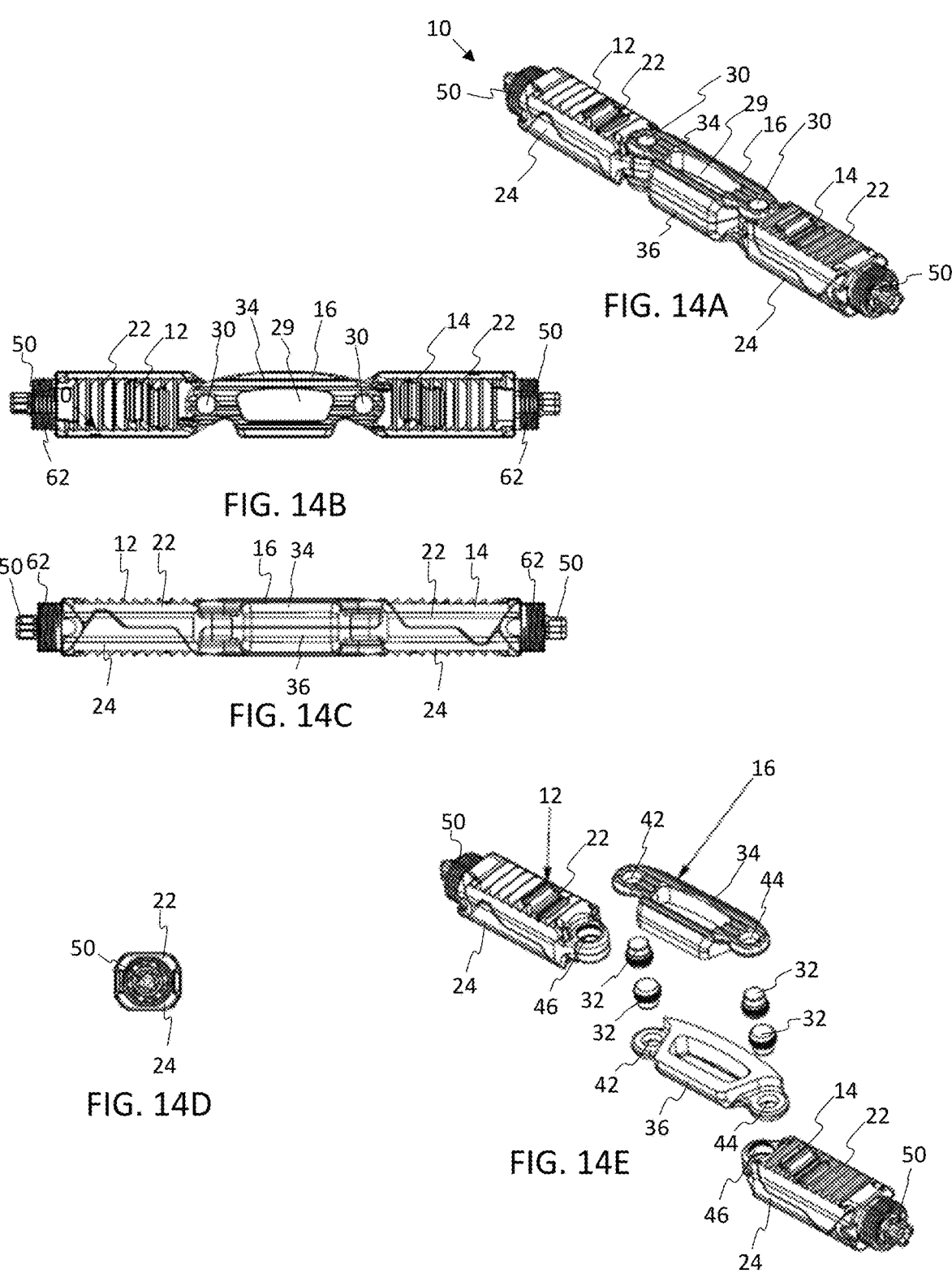
FIGS. 14A-14E show perspective, top, rear, side, and exploded views of the expandable fusion device according to one embodiment, in a fully collapsed and linear orientation configured to be inserted into the body.
Figure 17A:
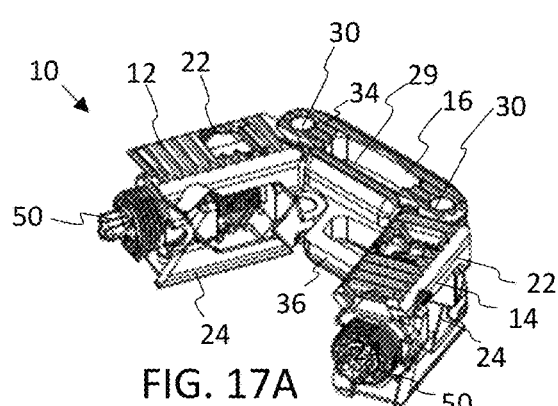
FIGS. 17A-17E show perspective, top, rear, side, and exploded views of the expandable fusion device in FIGS. 16A-16E with both lateral legs and attached link plates expanded in parallel.
Figure 17B:
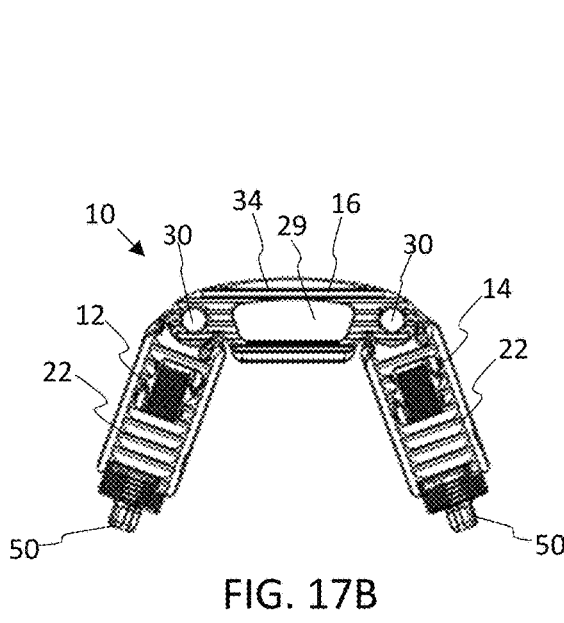
Figure 17C:
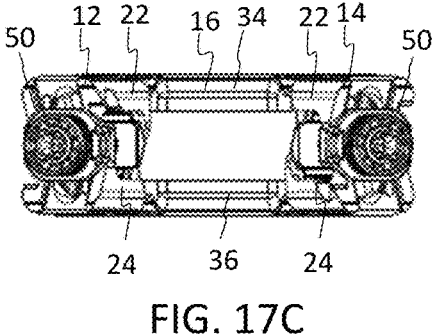
Figure 17E:
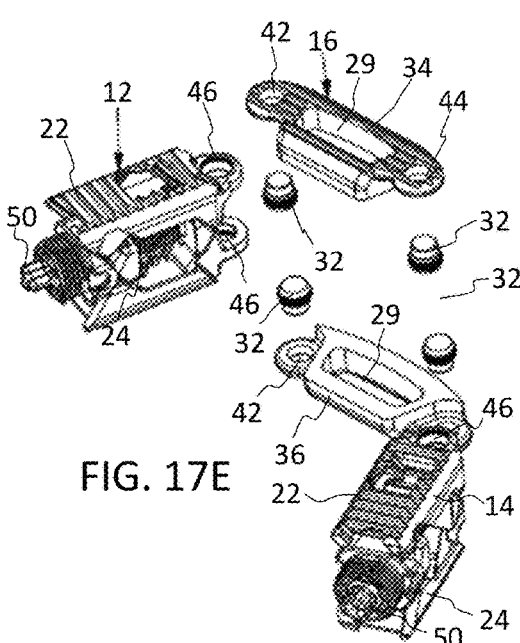
Figure 17D:
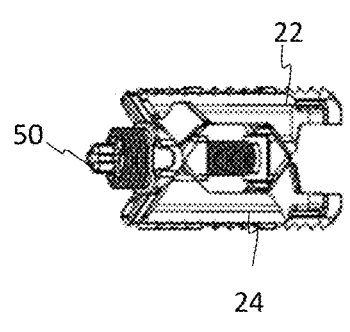
Figure 17D:
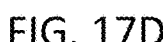
Figure 18A:
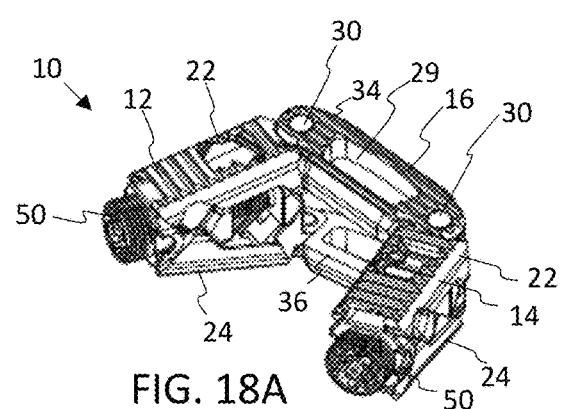
FIGS. 18A-18E show perspective, top, rear, side, and exploded views of the expandable fusion device in FIGS. 17A-17E with the lateral legs non-uniformly expanded.
Figure 18B:
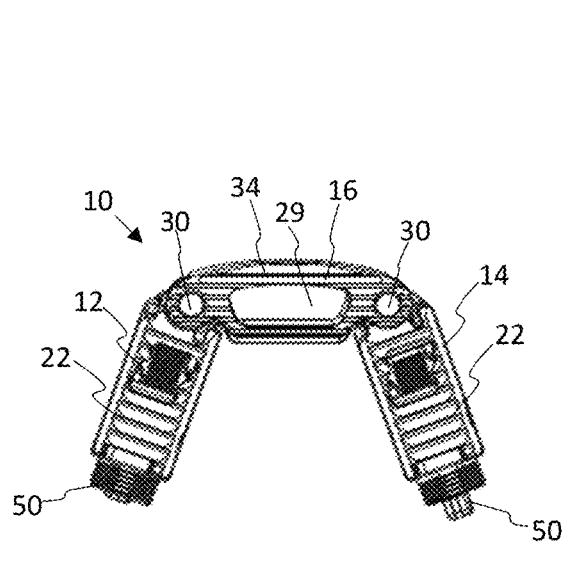
Figure 18C:
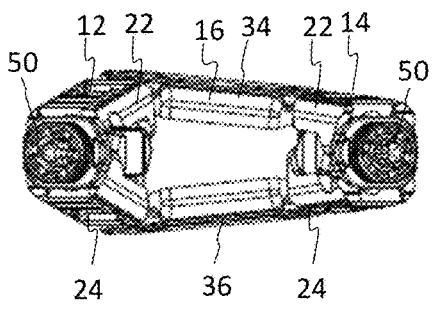
Figure 18E:
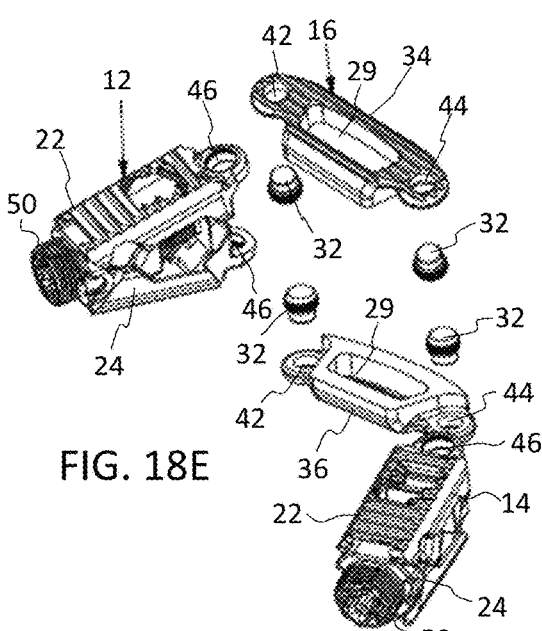
Figure 18D:
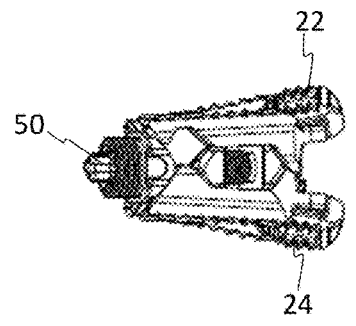
Figures 19A, 19B, 19C, 19D, 19E:
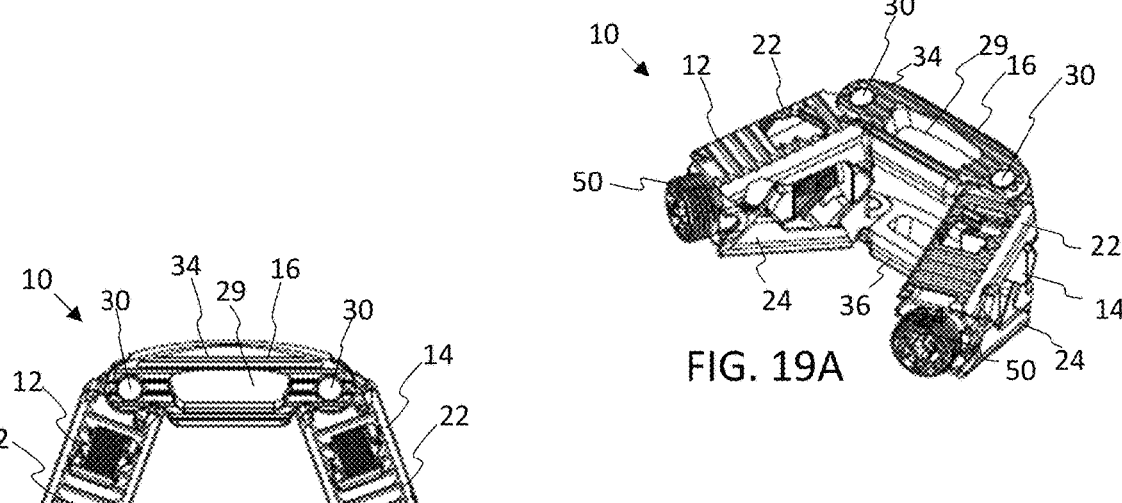
FIGS. 19A-19E show perspective, top, rear, side, and exploded views of the expandable fusion device in FIGS. 17A-17E with both lateral legs uniformly expanded.

FIG. 7E shows the lateral leg 12 with a central longitudinal axis A and a longitudinal axis C offset to axis A. FIG. 7F shows FIG. 7E along line A-A and FIG. 7G shows FIG. 7E along line C-C. As best seen in FIG. 7F, the front driving ramp 58 includes a threaded bore 59, and the front driving ramp 58 is positioned on the first threaded portion 70 of the actuator 52. The front driving ramp 58 is threadedly moveable along the length of the first threaded portion 70. The mid-ramp 60 includes a threaded bore 61, and the mid-ramp 60 is positioned on the second threaded portion 72 of the actuator 52. The mid-ramp 60 is threadedly moveable along the length of the second threaded portion 72 of the actuator 72. The rear ramp 62 is engaged with the nut 54, which is positioned along the third threaded portion 74 and is moveable along the length of the third threaded portion 74. The driving ramps 56 are each moveable along their respective threaded portions 70, 72, 74 to move the upper and lower endplates 26, 28, and thereby expand the lateral leg 12, 14. The threaded portions 70, 72, 74 may have the same or different outer diameters and/or handedness. The proximal end 66 of the actuator shaft 64 may include a first instrument retention feature, such as a ribbed neck 76. The ribbed neck 76 may include knurled neck grips or other suitable engagement surfaces, which are configured to interface with a driver instrument to thereby rotate the actuator shaft 64.

The actuation assembly 50 may include a rotatable nut 54. The rotatable nut 54 may be configured to move the rear ramp 62 independent of the mid-ramp 60 and front ramp 58. The nut 54 may extend from a proximal end 78 to a distal end 80. The proximal end 78 may include a second instrument retention feature, such as a slotted head 82. The slotted head 82 may include slots or other suitable engagement surfaces configured to interface with a driver instrument to thereby rotate the nut 54. When only the nut 54 is rotated clockwise, the rear ramp 62 may be translated forward, decreasing its distance to the front ramp 58 such that the posterior height increases and the anterior height decreases, thus decreasing the lordotic angle of the spacer. When the nut 54 remains stationary and only the actuator 52 is rotated clockwise, the mid ramp 60 moves away from the front ramp 58 increasing the anterior height, at the same time the rear ramp 62 moves away relative to the front ramp 58 as the actuator 52 advances through the nut 54. increasing the gap between the rear ramp 62 and the front ramp 58 increases the lordotic angle of the spacer. When both the actuator 52 and the nut 54 are rotated clockwise at the same time, the rear ramp 62 and front ramp 58 do not move relative to each other. Only the mid ramp 60 translates away from the front ramp 58 and towards the rear ramp 62. This results in expansion of the endplates 26, 28 in parallel. It will be appreciated that the movement of the driving ramps 58, 60, 62 and resulting expansion may be operated by the actuator 52 and/or nut 54 with any suitable configurations and mechanisms.

The driving ramps 58, 60, 62 engage with upper and lower endplates 26, 28 to thereby move the upper and lower endplates 26, 28 outwardly in height. It will be appreciated that the lower endplate 28 is identical, or a mirror image of, the upper endplate 26 and the description for the upper endplate 26 herein applies equally to the lower endplate 28. The upper endplate 26 includes an outer surface 84 configured to engage the adjacent vertebrae and an inner surface 86 configured to mate with the driving ramps 58, 60, 62. The inner surface 86 may include one or more ramped surfaces 88, 90, 92. In the embodiment shown, the inner surface 86 includes at least one first ramped surface 88 near the distal end of the endplate 26, 28, at least one second ramped surface 90 near the proximal end of the endplate 26, 28, and at least one third ramped surface 92 between the first and second ramped surfaces 88, 90. For example, the inner surface 86 may include a pair of first ramped surfaces 88, a pair of second ramped surfaces 90, and a pair of third ramped surfaces 92. The first and second ramped surfaces 88, 90 may face the proximal end, and the third ramped surface 92 may face the distal end of the endplate 26, 28.

The ramped surfaces 88, 90, 92 may be angled continuous surfaces with a given angle of slope. It is contemplated that the slope of the ramped surfaces 88, 90, 92 may be equal or can differ from each other. The ramped surfaces 88, 90, 92 may be generally straight ramped surfaces or may be curved ramped surfaces. The ramped surfaces 88, 90, 92 may include male slide ramps or protruding ramps. The first and second ramped surfaces 88, 90 may be spaced apart at an equal distance such that the ramped surfaces 88, 90 are substantially parallel to one another. The third ramped surface 92 may be angled opposite to the first and second ramped surfaces 88, 90. In this way the apex of the third ramp 92 may meet or near the apex of the second ramp 90 and the base of the third ramp 92 may extend toward the base of the first ramp 88. Although a specific arrangement of ramped surfaces 88, 90, 92 is shown, it is envisioned that the number, location, and configuration of ramped surfaces 88, 90, 92 may be modified or selected by one skilled in the art.

The driving ramps 58, 60, 62 may include one or more ramped surfaces 94, 96, 98. The ramped surfaces 94, 96, 98 of the driving ramps 58, 60, 62 may be configured and dimensioned to engage the corresponding ramped surfaces 88, 90, 92 of the upper and lower endplates 26, 28, respectively. For example, the front ramp 58 may include one or more ramped surfaces 94, mid-ramp 60 may include one or more ramped surfaces 96, and rear ramp 62 may include one or more ramped surfaces 98. For example, the front ramp 58 may include a first pair of upper ramped surfaces 94 and a second pair of lower ramped surfaces 94. The mid-ramp 60 may include a first pair of upper ramped surfaces 96 and a second pair of lower ramped surfaces 96. The rear ramp 62 may include a first pair of upper ramped surfaces 98 and a second pair of lower ramped surfaces 98. The ramped surfaces 94, 96, 98 may be angled continuous surfaces with a given angle of slope. It is contemplated that the slope of the ramped surfaces 94, 96, 98 may be equal or can differ from each other.

The ramped surfaces 94, 96, 98 may be generally straight ramped surfaces or may be curved ramped surfaces. The ramped surfaces 94, 96, 98 may include female slide ramps or recessed ramps configured to receive the male ramped surfaces 88, 90, 92 of the upper and lower endplates 26, 28, respectively. A dovetail type connection may be formed between the ramped surfaces for stability and reliability, although other mating and sliding engagements can be used. It will be appreciated that the male and female ramps may be reversed or may be otherwise configured to provide for slidable mating between the ramps.

The first ramped surface 88 of the endplate 26, 28 may be configured to slidably interface with the ramped surface 94 of the front driving ramp 58. The second ramped surface 90 of the endplate 26, 28 may be configured to slidably interface with the ramped surface 98 of the rear ramp 62. The third ramped surface 92 of the endplate 26, 28 may be configured to slidably interface with the ramped surface 96 of the mid-ramp 60. As one or more of the driving ramp 58, 60, 62 moves, the ramped surface or surfaces 94, 96, 98 pushes against the corresponding ramped surface or surfaces 88, 90, 92 of the upper and lower endplates 26, 28. In this manner, the individual driving ramps 58, 60, 62 control the rate of expansion of the upper and lower endplates 26, 28. The upper and lower endplate 26, 28 are pushed outwardly into the expanded configuration.

The actuation assembly 50 may further include one or more of the following features. The driving rear ramp 62 may include an outer threaded portion 100 at the proximal end which may be configured to be retained by an insertion instrument. One or more securing rings or washers 102 may be provided to secure the nut 54 to the assembly 50. For example, the securing washer 102 may be received in an annular channel 104 near the distal end 80 of the nut 54, thereby connecting the rear ramp 56 to the nut 54. One or more friction rings may also be provided to provide drag or thrust resistance to the nut 54 and/or driving ramps 58, 60, 62, respectively. A split ring 106 may be provided to capture and secure the actuator 52 in the assembly 50. The split ring 106 may be provided along a non-threaded portion 108 of the shaft 64, for example, having a reduced diameter between the second and third threaded portions 72, 74.

With emphasis on FIGS. 10-13, another embodiment of an expandable lateral leg 112 is shown. Lateral leg 112 is similar to lateral legs 12, 14, with the addition of a retaining ring or snap ring 114 in the actuation assembly 50. The retaining ring or snap ring 114 may be used to further secure the nut 54 to the rear driving ramp 56. The snap ring 114 may fit into a recessed groove inside the rear driving ramp 56, for example. Once installed, the exposed portion of the snap ring 114 may act as a shoulder to retain the rear driving ramp 56 to the nut 54. FIGS. 11A-11G show the expandable lateral leg 112 in its fully collapsed position. FIGS. 12A-12G show the expandable lateral leg 112 in one expanded position, where the front ramp 58 is advanced toward the distal end 20 and the mid-ramp 60 is advanced away from the front 58 toward the proximal end 18 of the lateral leg 112. FIGS. 13A-13G show the upper and lower endplates 22, 24 expanded substantially in parallel.

Turning now to FIGS. 14-19, the implant 10 may be articulated and/or expanded into a number of different configurations. In FIGS. 14A-14E the implant 10 is shown in a fully collapsed and linear orientation, which is configured to be inserted into the body of a patient, for example, through a cannula. In FIGS. 15A-15E, the first lateral leg 12 is articulated relative to the link plates 16 joining the first lateral leg 12 to the second lateral leg 14. For example, the first lateral leg 12 is hinged at an angle about pins 32 and link plates 16 and second lateral leg 14 remain in a linear orientation along longitudinal axis A. In FIGS. 16A-16E, the first and second lateral legs 12, 14 are both articulated. For example, the first lateral leg 12 is hinged at a first angle relative to the link plates 16 and the second lateral leg 14 is hinged at a second angle relative to the link plates 16. The first and second angles may be the same or different. In this widened orientation, the implant 10 has a large footprint configured to maximize contact with the vertebral bodies. In FIGS. 17A-17E, the lateral legs 12, 14 are shown expanded in parallel, which thereby provides for the link plates 34, 36 expanded in parallel as well. In FIGS. 18A-18E, the lateral legs 12, 14 are non-uniformly expanded relative to one another. By expanding one lateral leg 12, 14 more or less than the other, coronal adjustments may be made to the spine. In FIGS. 19A-19E, both of the lateral legs 12, 14 are shown uniformly expanded with greater anterior heights and the attached link plates 34, 36 are passively expanded in parallel.

Figure 20:
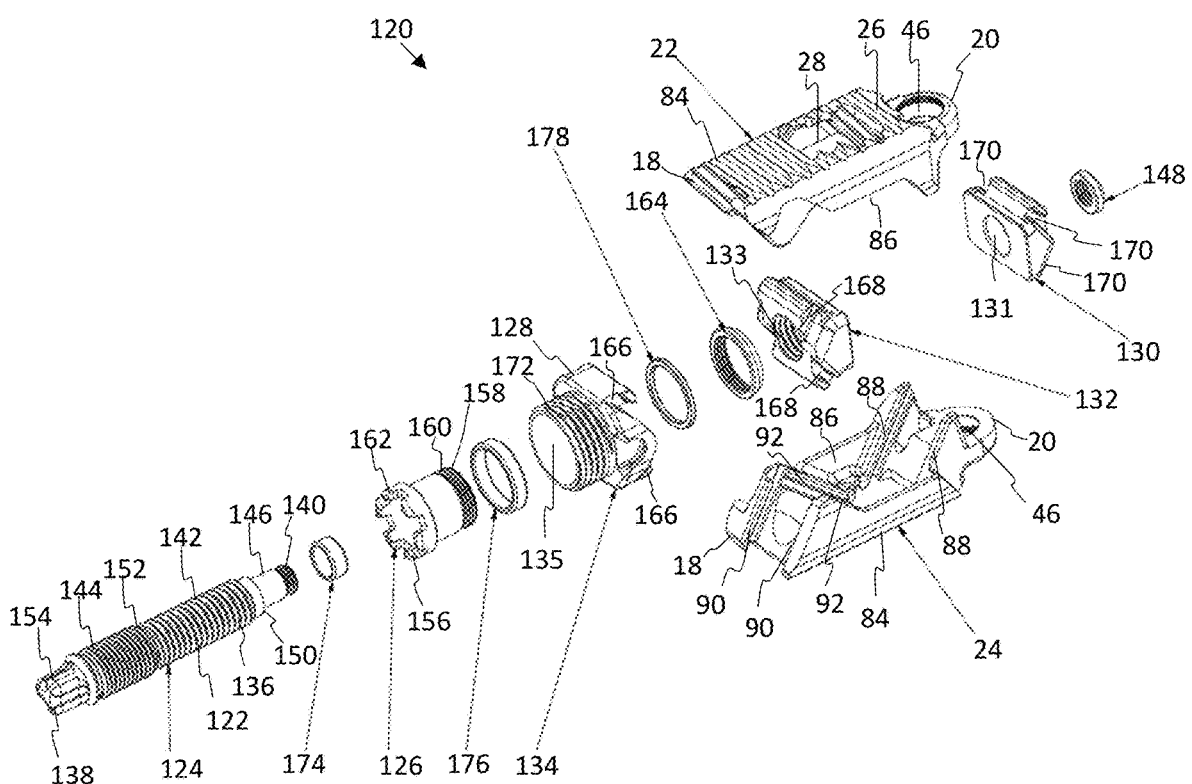
FIG. 20 is an exploded view of one of the expandable lateral legs according to another embodiment.
Figures 21A, 21B, 21C, 21D, 21E:
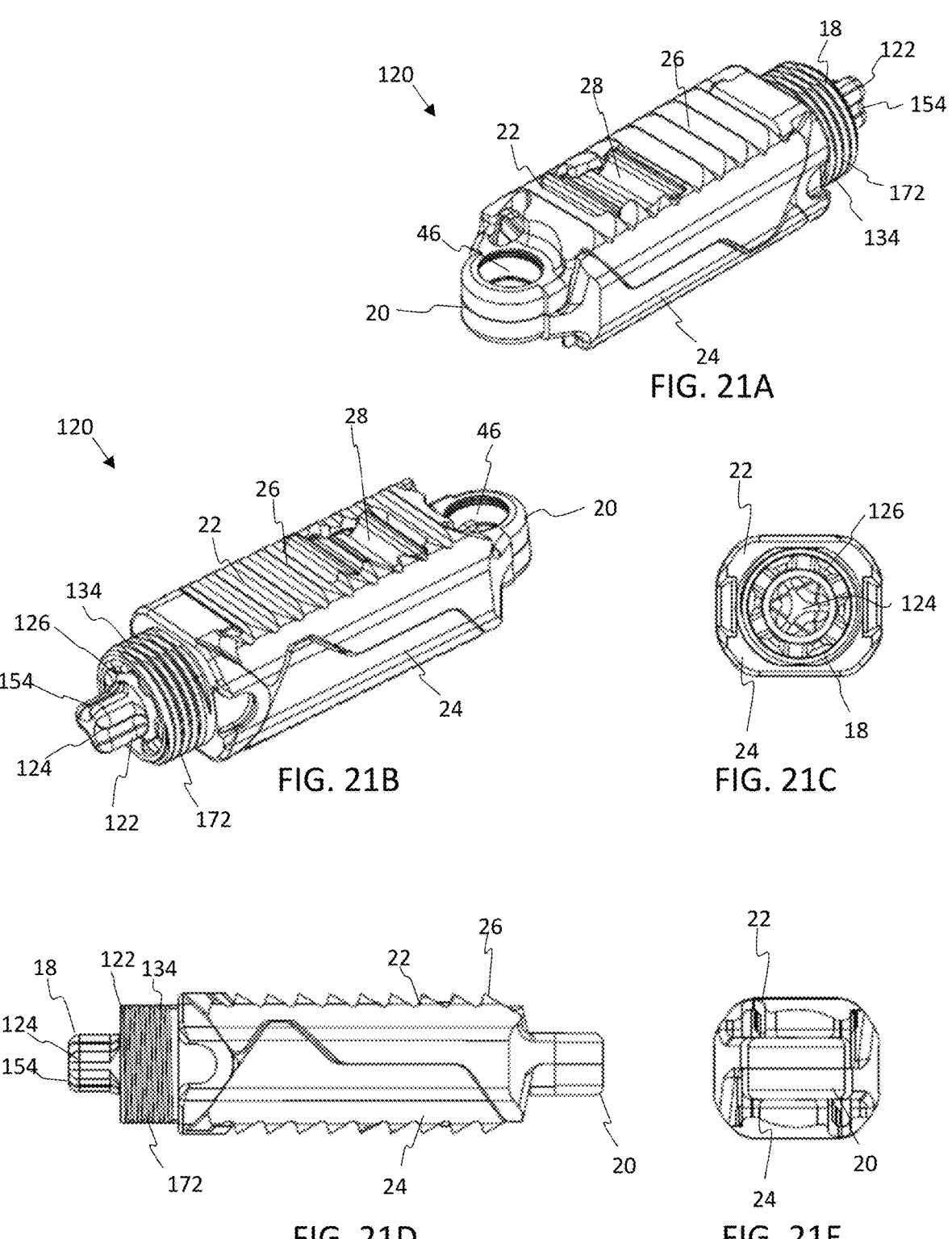
FIGS. 21A-21H show perspective, rear, side, front, top, and cross-sectional views of the lateral leg of FIG. 21 in a fully collapsed position.
Figures 21F, 21G, 21H:
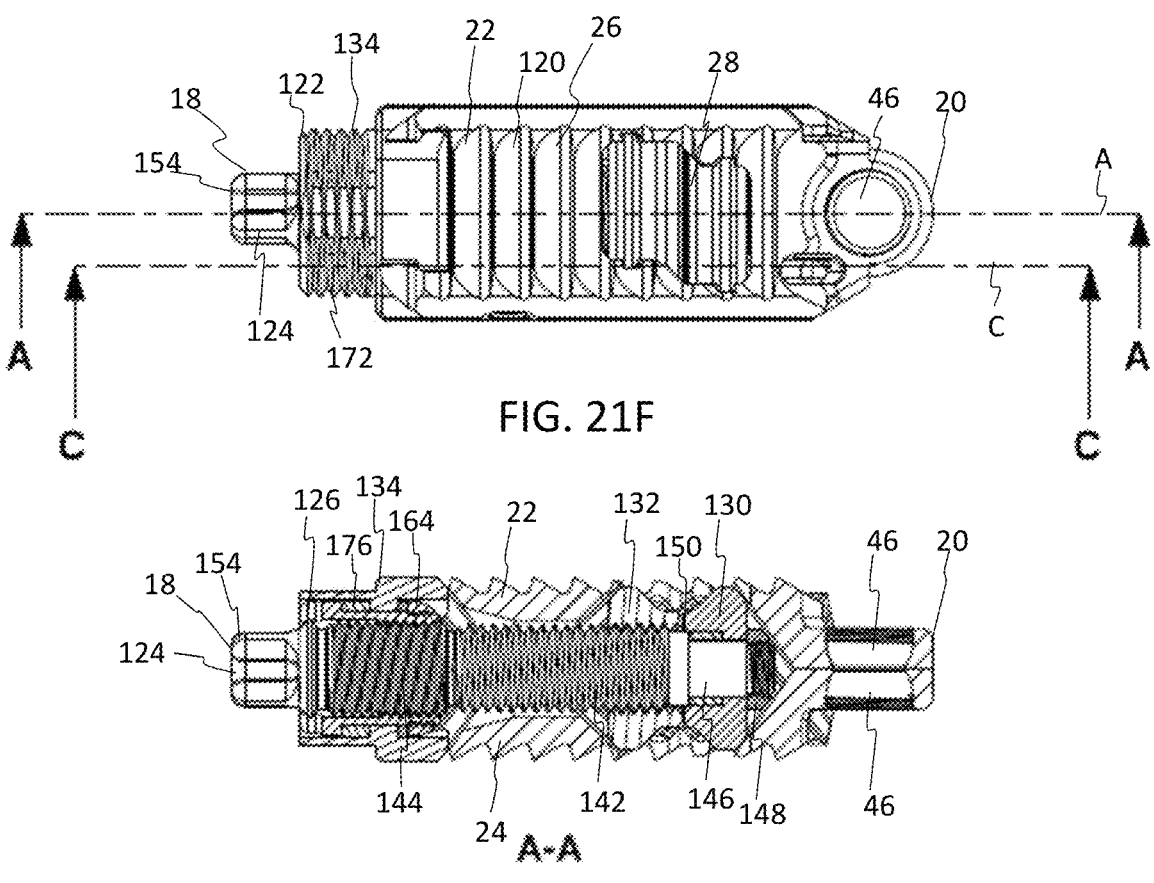

Turning now to FIG. 20, another embodiment of an expandable lateral leg 120 is shown. Lateral leg 120 is similar to lateral legs 12, 14, 112 except an alternative actuation assembly 122 is provided. The upper and lower endplates 22, 24 are the same or similar to the endplates described herein except the endplates 22, 24 include a single central graft window 28. The lateral leg 120 includes an actuation assembly 122 with an actuator 124 and a nut 126 configured to move a plurality of internal ramps 128, which expand the endplate 22, 24 in height. The plurality of ramps 128 may include a plurality of driving ramps including a front ramp 130, a mid-ramp 132, and a rear ramp 134. The front ramp 130 may include a central longitudinal bore 131, the mid-ramp 132 may include a central longitudinal bore 133, and the rear ramp 134 may include a central longitudinal bore 135. The plurality of driving ramps 130, 132, 134 may be positioned along the length of the actuator 124 and are configured to engage and drive the upper and lower endplates 22, 24, respectively. When one or more of the driving ramps 130, 132, 134 are moved and slide against the upper and lower endplates 22, 24, the lateral leg 120 expands in height. The expansion may include the ability to individually adjust the anterior and/or posterior heights of the lateral legs 120.

The actuation assembly 122 is configured to expand the height of the respective lateral legs 120. The actuation assembly 122 includes rotatable drive screw or actuator 124 and rotatable drive nut 126 configured to move a plurality of internal ramps 128. Each lateral leg 120 includes at least three driving ramps: front ramp 130, mid-ramp 132, and rear ramp 134, which interface with the actuator 124. The actuator 124 may include a shaft 136 extending from a proximal end 138 to a distal end 140. The shaft 136 includes a first threaded portion 142, a second threaded portion 144, and a non-threaded portion 146. The first threaded portion 142 may be positioned between the non-threaded portion 146 and the second threaded portion 144. The first and second threaded portions 142, 144 may have the same or different attributes including outer diameters, handedness, thread form, thread angle, lead, pitch, etc.

Figures 22A, 22B, 22C, 22D, 22E:
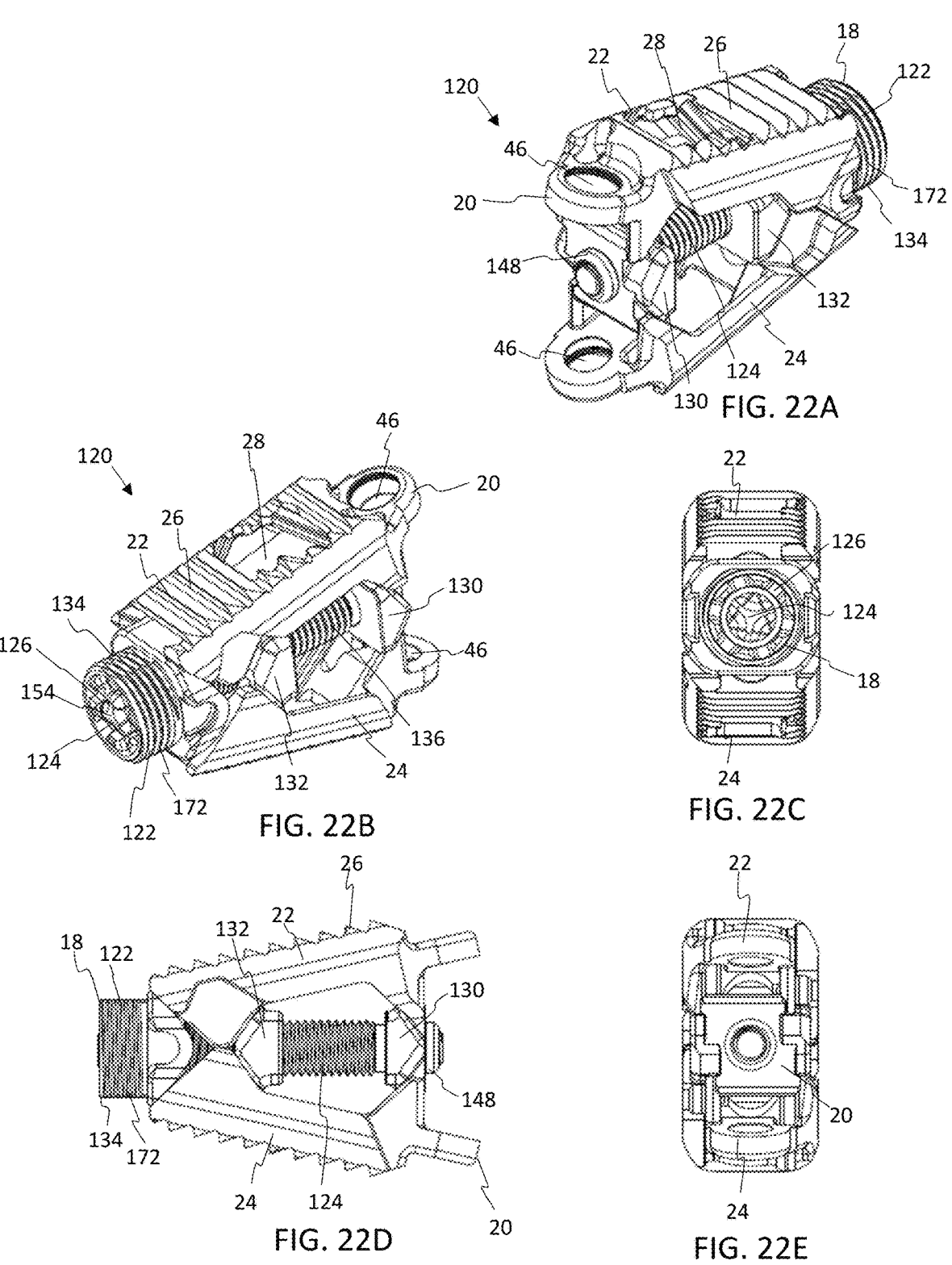
FIGS. 22A-22H show perspective, rear, side, front, top, and cross-sectional views of the lateral leg of FIG. 21 in one expanded position.
Figures 22F, 22G, 22H:
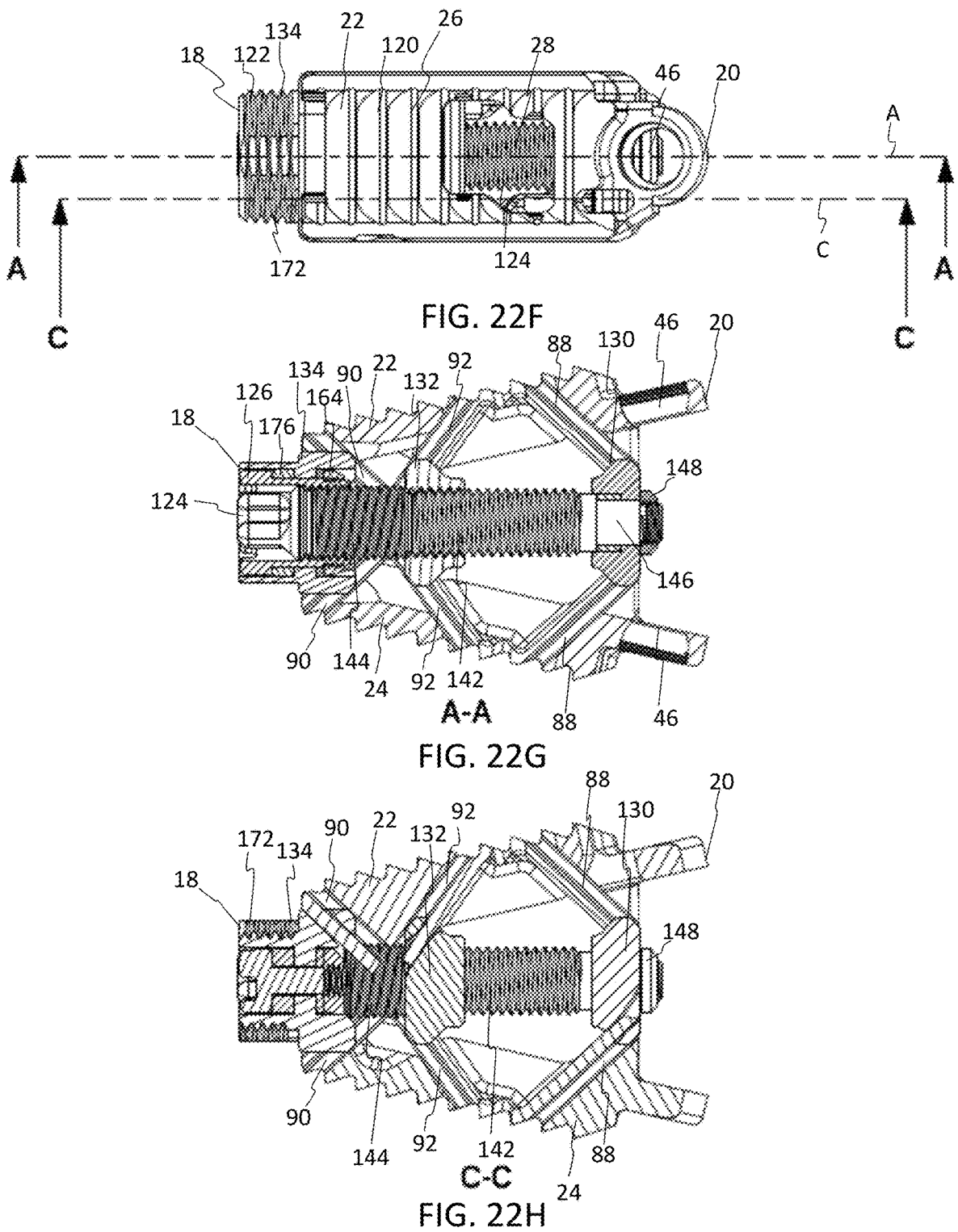
Figures 23A, 23B, 23C, 23D, 23E:
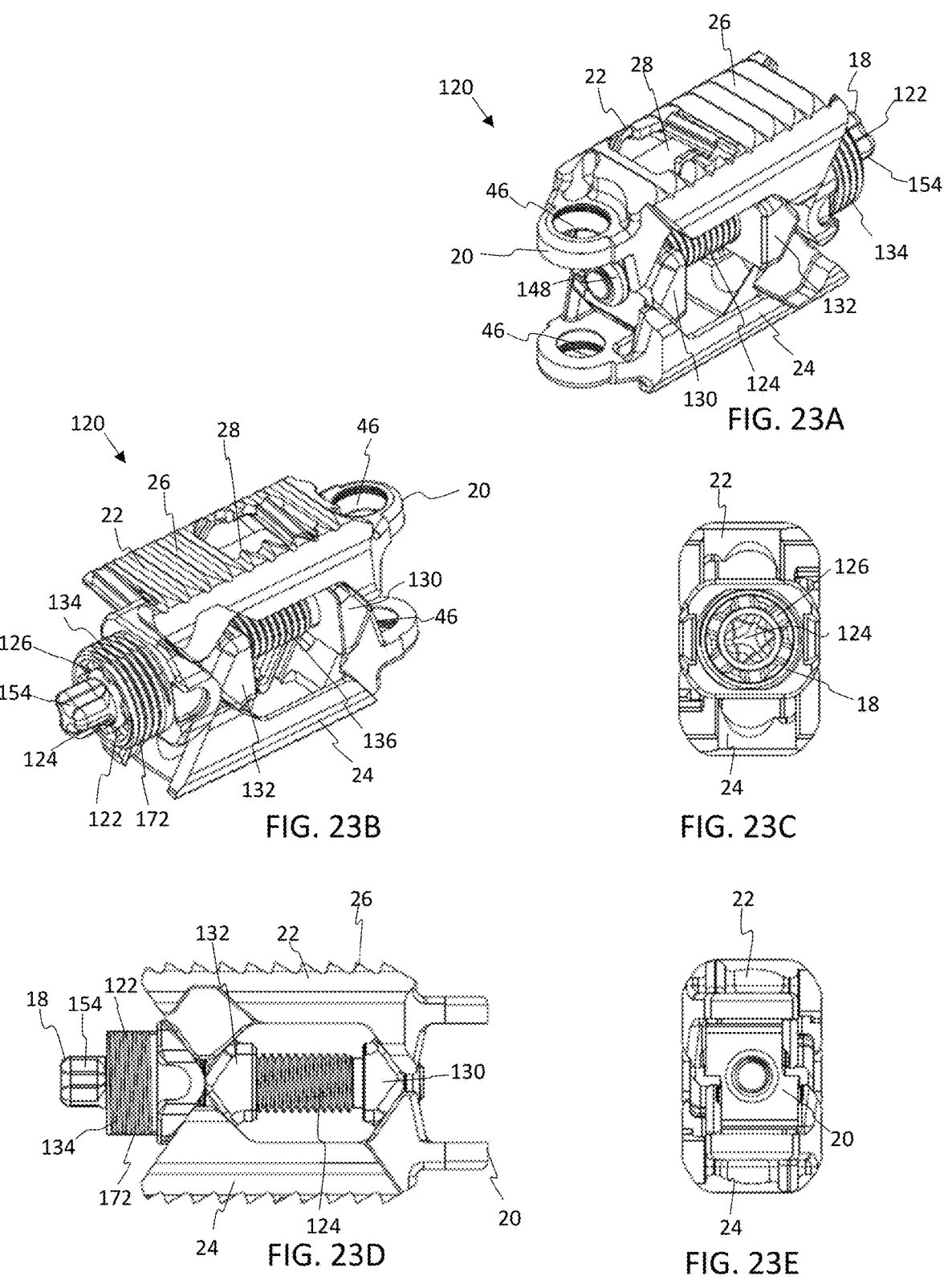
FIGS. 23A-23H show perspective, rear, side, front, top, and cross-sectional views of the lateral leg of FIG. 21 with the endplates expanded in parallel.
Figures 23F, 23G, 23H:
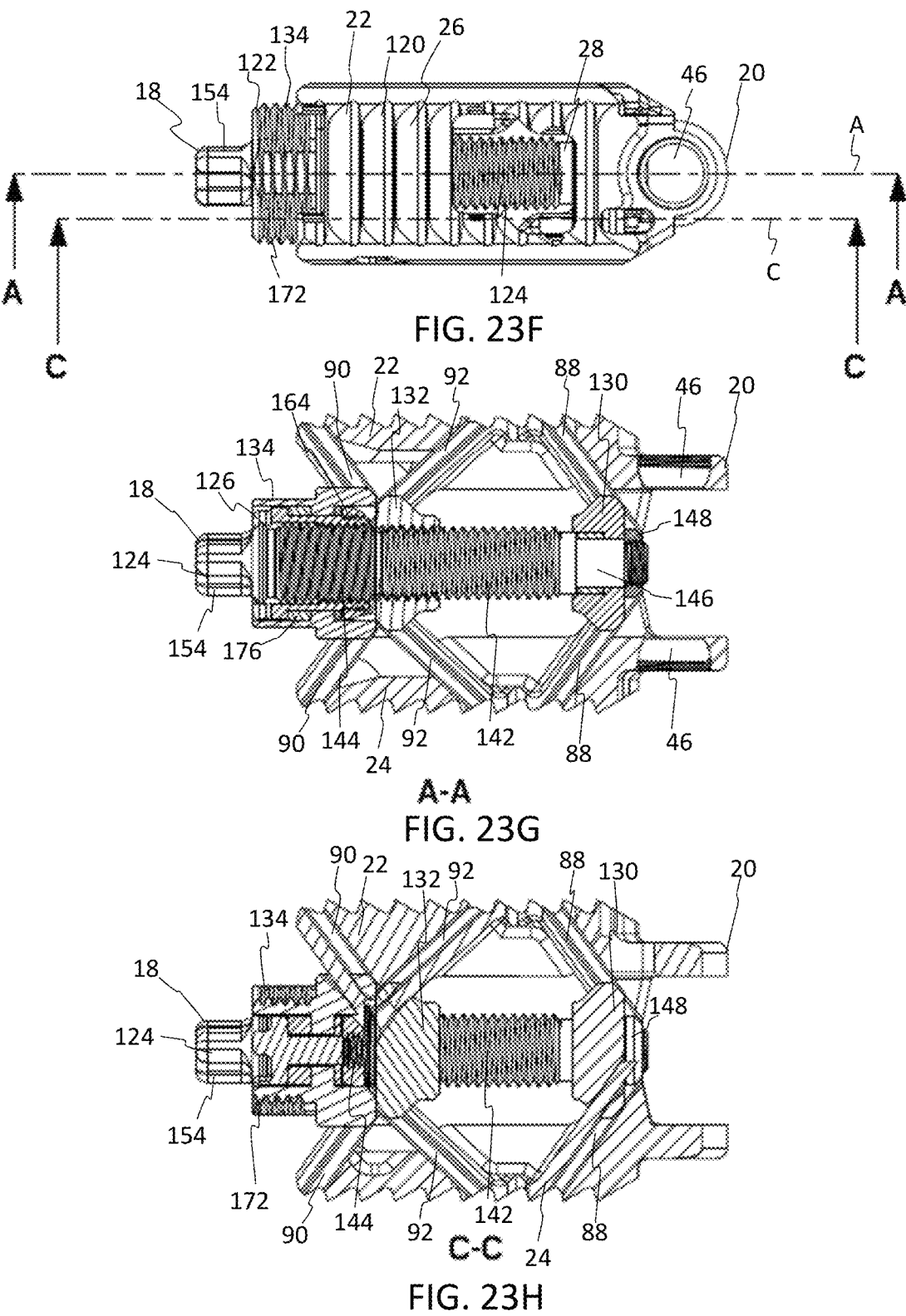
Figures 24A, 24B, 24C, 24D, 24E:
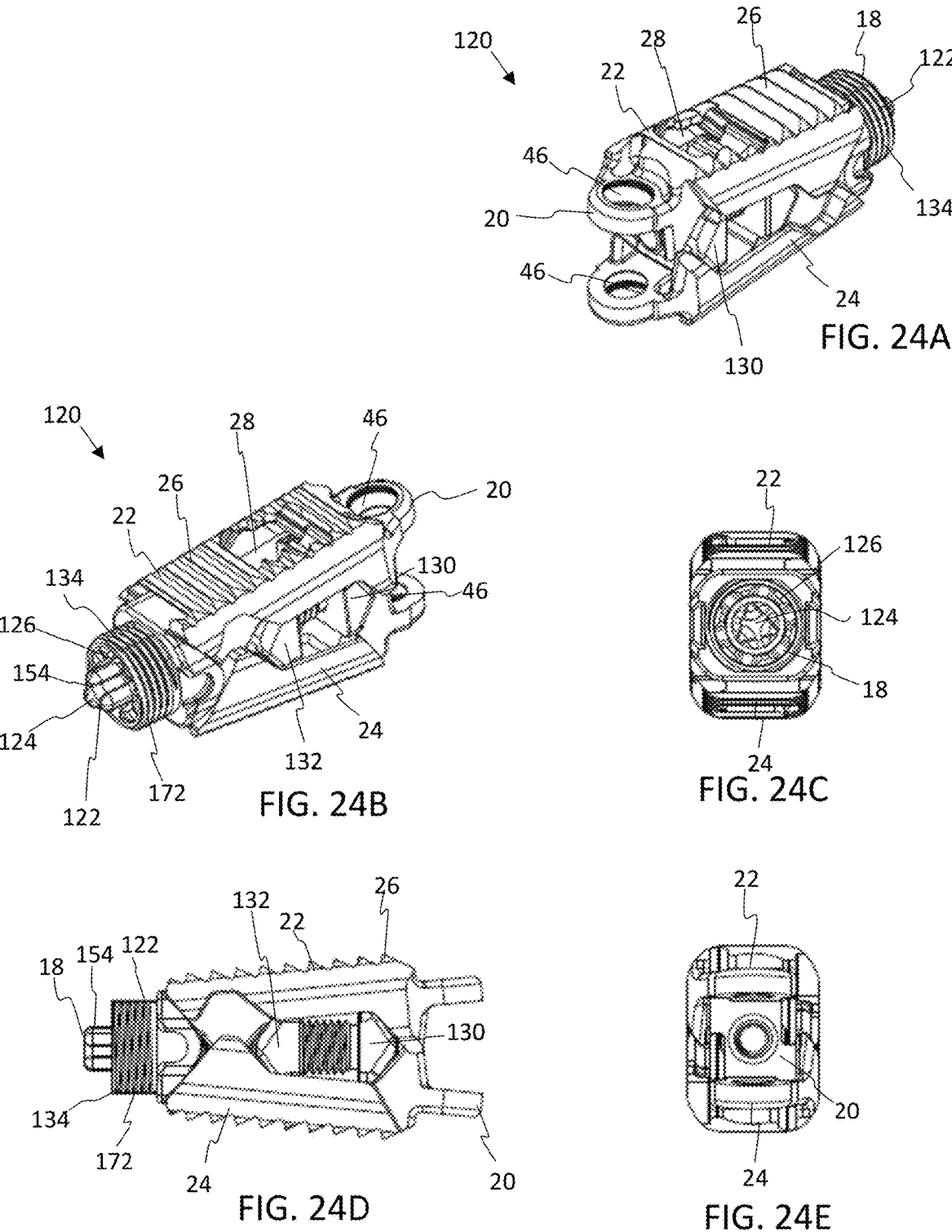
FIGS. 24A-24H show perspective, rear, side, front, top, and cross-sectional views of the lateral leg of FIG. 21 in another expanded position.
Figures 24F, 24G, 24H:
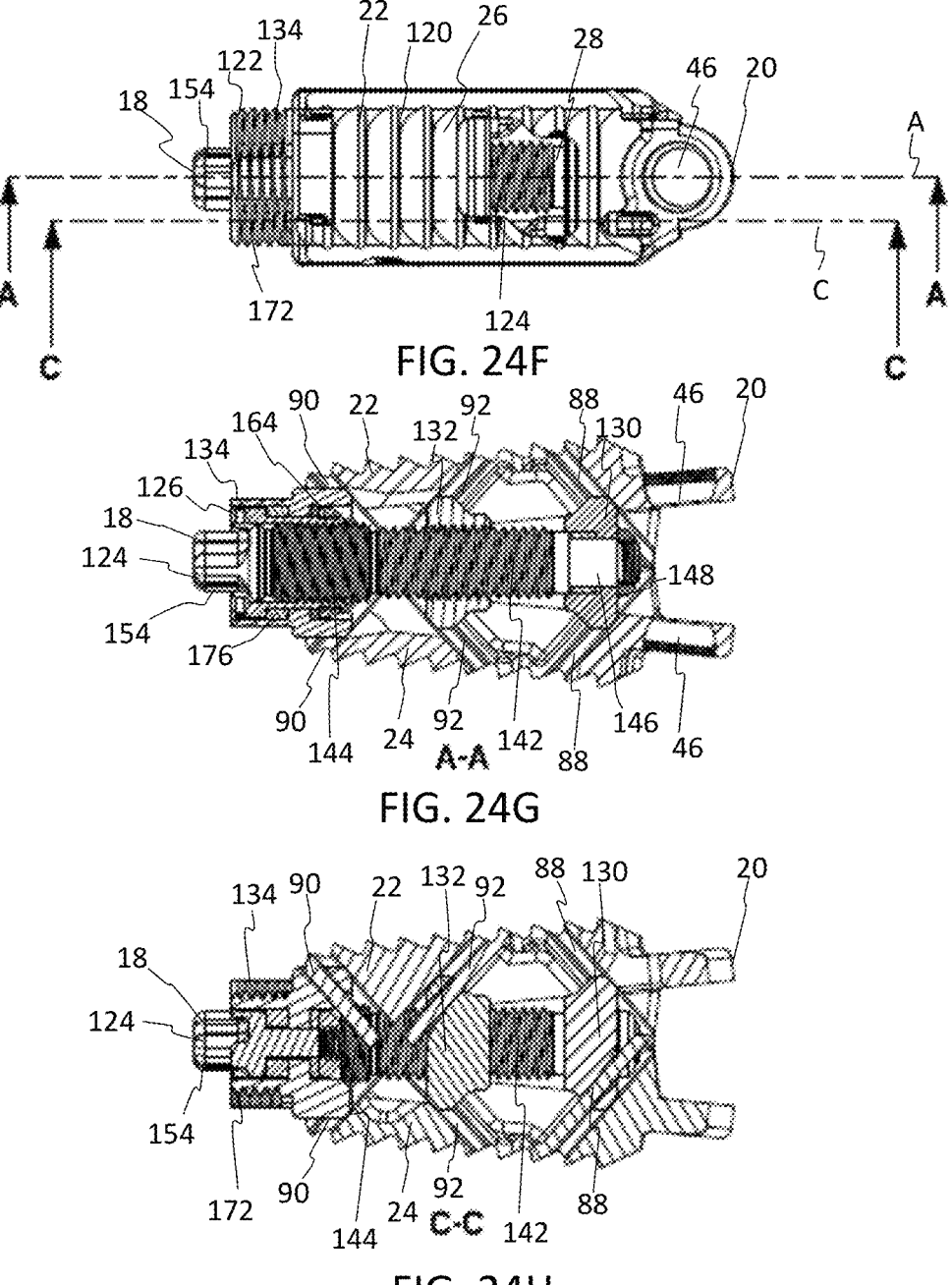
Figures 25A, 25B:
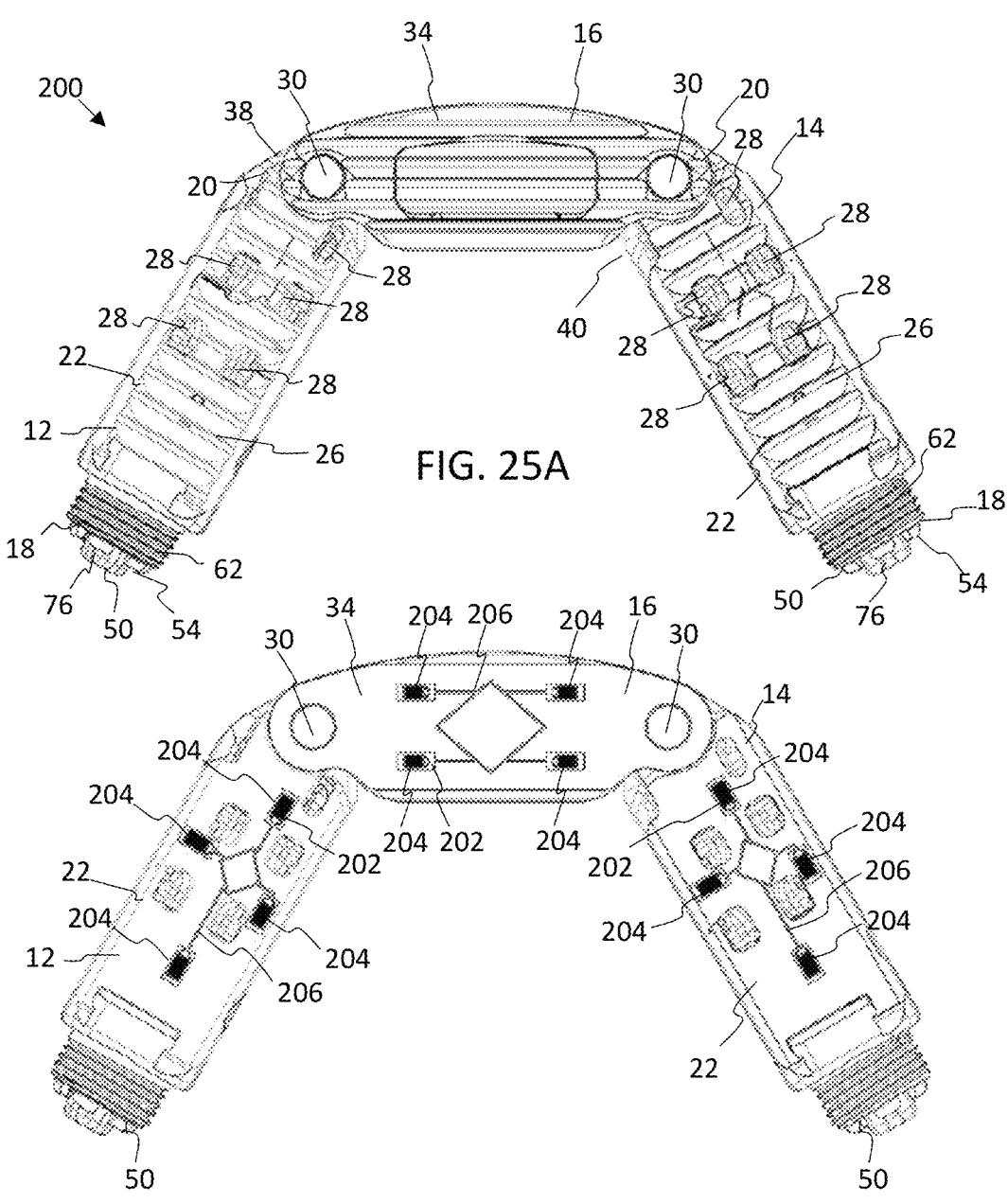
FIGS. 25A-25D show top, partial cross-sectional, and perspective views of an embodiment of the implant having one or more strain gauges configured to measure the forces acting on the endplates and/or the link plates.
Figure 25C:
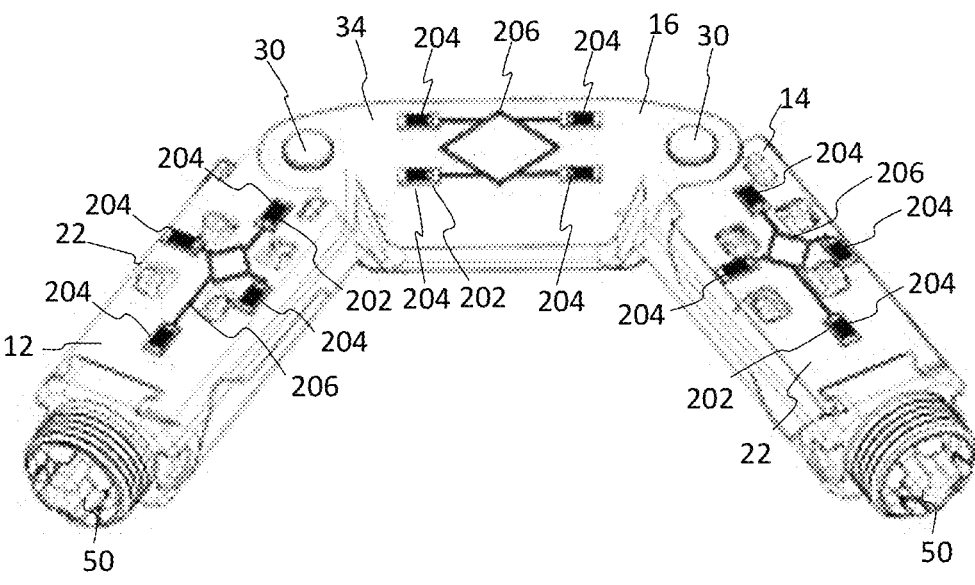
Figure 25D:
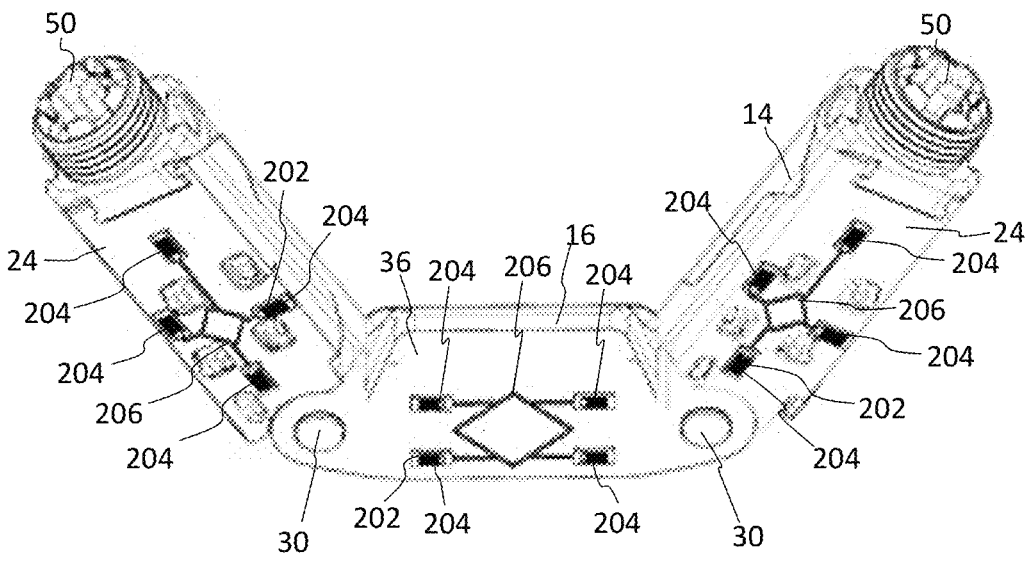

In FIGS. 21A-21H, the lateral leg 120 is shown in a fully collapsed configuration. In FIGS. 22A-22H, the lateral leg 120 is shown expanded in height with a greater anterior height. In FIGS. 23A-23H, the lateral leg 120 is shown expanded with the endplates 22, 24 generally in parallel. In FIGS. 24A-24H, the lateral leg 120 is shown expanded to a lesser degree with an increased anterior height. As best seen in FIG. 22G, the front driving ramp 130 includes a non-threaded bore 131, which is positioned on the non-threaded portion 146 of the actuator 124. The front driving ramp 130 may be located between internally threaded locking cap 148 and a shoulder 150 defined between the first threaded portion 142 and the non-threaded portion 146. In this manner, the front ramp 130 is secured to the actuator shaft 136.

The mid-ramp 132 includes a threaded bore 133, which is positioned on the first threaded portion 142 and is moveable along the length of the first threaded portion 142 in order to move the mid-ramp 132 and thereby move the upper and lower endplates 22, 24 to expand the lateral leg 120. The rear ramp 134 is engaged with the nut 126, which is positioned along the second threaded portion 144 in order to move the rear ramp 134. The rear ramp 134 is moveable along the length of the second threaded portion 144 to move the upper and lower endplates 22, 24 and expand the lateral leg 120. The first threaded portion 142 may have a smaller outer diameter and different handedness than the second threaded portion 144. The first threaded portion 142 may transition to the second threaded portion 144 at a second shoulder 152. The proximal end 138 of the actuator shaft 136 may include a first instrument retention feature, such as a ribbed neck 154. The ribbed neck 154 may include knurled neck grips or other suitable engagement surfaces, which are configured to interface with a driver instrument to thereby rotate the actuator shaft 136.

The actuation assembly 122 may also include rotatable drive nut 126. The rotatable nut 126 may be configured to move the rear ramp 134 independent of the mid-ramp 132 and front ramp 130. The nut 126 may extend from a proximal end 156 to a distal end 158. The distal end 158 may include an outer threaded portion 160 configured to mate with a threaded cap or internally threaded ring 164. In an alternative embodiment, the threaded portion 160 may be configured to mate with a corresponding internal threaded portion in the bore 135 through the rear driving ramp 134. The proximal end 156 may include a second instrument retention feature, such as a slotted head 162. The slotted head 162 may include slots or other suitable engagement surfaces configured to interface with a driver instrument to thereby rotate the nut 126. When only the nut 126 is rotated clockwise, the rear ramp 134 may be translated forward, decreasing its distance to the front ramp such that posterior height increases and the anterior height decreases. When the nut 126 remains stationary and only the actuator 124 is rotated clockwise, increasing the gap between the rear ramp 62 and the front ramp 58 increases the lordotic angle of the spacer. When both the actuator 124 and the nut 126 are rotated clockwise at the same time, the rear ramp 134 and mid-ramp 132 may slide together, thereby moving the endplates 22, 24 in parallel. It will be appreciated that the movement of the driving ramps 130, 132, 134 and resulting expansion may be operated by the actuator 124 and/or nut 126 with any suitable configurations and mechanisms.

The driving ramps 130, 132, 134 may include one or more ramped surfaces 166, 168, 170. The ramped surfaces 166, 168, 170 of the driving ramps 130, 132, 134 may be configured and dimensioned to engage the corresponding ramped surfaces 88, 90, 92 of the upper and lower endplates 22, 24, respectively. For example, the rear ramp 134 may include one or more ramped surfaces 166, mid-ramp 132 may include one or more ramped surfaces 168, and front ramp 130 may include one or more ramped surfaces 170. The ramped surfaces 166, 168, 170 may be angled continuous surfaces with a given angle of slope. It is contemplated that the slope of the ramped surfaces 166, 168, 170 may be equal or can differ from each other. The ramped surfaces 166, 168, 170 may be generally straight ramped surfaces or may be curved ramped surfaces. The ramped surfaces 166, 168, 170 may include female slide ramps or recessed ramps configured to receive the male ramped surfaces 88, 90, 92 of the endplates 22, 24. It will be appreciated that the male and female ramps may be reversed or may be otherwise configured to provide for slidable mating between the ramps.

The second ramped surface 90 of the endplate 22, 24 may be configured to slidably interface with the ramped surface 166 of the rear ramp 134. The first ramped surface 88 of the endplate 22, 24 may be configured to slidably interface with the ramped surface 170 of the front ramp 130. The third ramped surface 92 of the endplate 22, 24 may be configured to slidably interface with the ramped surface 168 of the driving mid-ramp 132. As one or more of the driving ramps 130, 132, 134 moves, the ramped surface or surfaces 166, 168, 170 pushes against the corresponding ramped surface or surfaces 88, 90, 92 of the upper and lower endplates 22, 24, respectively. In this manner, the individual driving ramps 130, 132, 134 control the rate of expansion of the upper and lower endplates 22, 24, which thereby controls the expansion of the anterior, posterior, and central heights of upper and lower endplates 22, 24. Accordingly, movement of the driving ramps 130, 132, 134, causes the upper and lower endplate 22, 24 to be pushed outwardly into the expanded configurations.

The lateral leg 120 may further include one or more of the following features. The rear ramp 134 may include an outer threaded portion 172 at the proximal end which may be configured to be retained by an insertion instrument. One or more friction rings or washers 174, 176, 178 may be provided to provide drag or thrust resistance to one or more of the moveable components in the assembly 122. The friction rings 174, 176, 178 may include PEEK washers or may be composed of another suitable material. For example, friction ring 174 may be provided to apply resistance to the drive screw 124. Friction ring 176 may be provided to apply resistance to the drive nut 126. A thrust washer 178 may be provided to apply resistance to the rear driving ramp 134.

In order to improve the access profile of the interbody implant 10 while maximizing cortical bone contact surface area, methods and systems of installing, articulating and/or expanding the implant may include one or more of the following. The implant may enter the disc space with a linear configuration and articulate to increase surface area contact on the anterior apophyseal ring. The orientation and position of the interbody implant in its final implanted position may be optimized by pre-/intra-op scans and/or normal population statistics that determine bone mineral density maps of the vertebral body. Robotic and/or navigation guidance may be used to correctly orient the interbody. Further details of robotic and/or navigational systems can be found in U.S. Patent Publication No. 2017/0239007, which is incorporated herein by reference in its entirety for all purposes.

In one embodiment, the implant may be implanted with one or more of the following steps: (1) A determination may be made on final optimal implant location to optimize bone mineral density of the contacted bone/implant interface. (2) Robotic and/or navigation may be used to determine the potential trajectories that will allow for this optimal implant location to be achieved. (3) A cannula may be docked on the disc space through Kambin's triangle, or the anatomical area that is bordered by the disc space, exiting nerve root, and traversing nerve root. (4) The expandable interbody may be inserted in a linear, non-expanded orientation. (5) The expandable interbody is actuated into the widened U-shaped footprint that fully maximizes surface contact area with the vertebral body. (6) The lateral legs of the expandable interbody are then expanded. If necessary, an additional portal may be used on the contralateral side of the disc space to provide an additional window through which to attach a driver and expand the opposite lateral leg. The expansion in height may be provided to precisely restore normal spinal alignment and evenly distribute the load across the vertebral endplates.

The expandable fusion devices described herein may be manufactured from a number of biocompatible materials including, but not limited to, titanium, stainless steel, titanium alloys, non-titanium metallic alloys, polymeric materials, plastics, plastic composites, PEEK, ceramic, and elastic materials.

The features of the embodiments described herein may provide one or more of the following advantages. A small insertion profile, such as an 8 mm insertion width into the disc space, may reduce the required skin, fascia, muscle, and/or ligamentous disruption. A controlled lordosis may be provided through placement of the interbody around the lateral anterior edges of the vertebral body and independent control of the anterior and posterior aspects of the cage. The large footprint and implant placement may serve to reduce the concerns of subsidence as well as increase the stability profile of the implant. The implant may have full independent control for adjustment of sagittal and coronal balance. It will be appreciated that different or additional advantages may also be achieved based on the disclosure herein.

Turning now to FIGS. 25A-27D, an embodiment of an implant 200 including one or more strain gauges 202 is shown. Implant 200 is similar to implant 10 described herein with the addition of the strain gauges 202 in the endplates 22, 24 and/or link plates 16. By adding one or more strain gauges 202, the implant 200 may measure the force, pressure, tension, and/or weight distribution across the surface area of the endplates 22, 24 and/or link plates 16. This may reduce the probability of subsidence and/or allow for precise placement of the implant 200 to provide a stable construct between interbody and bone.

In order to enhance precision placement of the implant 200 with equal distribution of force across the endplates 22, 24 and/or link plates 34, 36, one or more strain gauges 202 with one or more differential motion sensors 204 may be affixed to the endplates 22, 24 and/or link plates 34, 36. One or more sensors 204 may be distributed across the upper and lower endplates 22, 24 and/or upper and lower link plates 34, 36. The strain gauges 202 may be distributed across the implant 200 in order to provide the ability to measure differential pressures across the implant 200.

The strain gauge 202 may include a plurality of sensors 204 and a circuitry 206 connecting the sensors 204. The strain gauges 202 may include, for example, a thin strip of metal designed to measure mechanical load by changing resistance when stressed. The strain gauge 202 may be embedded in or affixed to the material of the endplates 22, 24 and/or link plates 34, 36. The strain gauge 202 may be recessed into or placed near the outer surfaces of the endplates 22, 24 and/or link plates 34, 36. In one embodiment, the strain gauge 202 is embedded within a 3D printed material. For example, the strain gauge 202 may be embedded within a 3D printed titanium material forming the endplates 22, 24 and/or link plates 34, 36. The gauges 202 and sensors 204 may be embedded within the foundation of the 3D printed endplates 22, 24 and/or link plates 34, 36, thereby providing complete integration between the material contacting the vertebral body and the sensors 204 registering the strain on that endplate 22, 24 and/or link plate 34, 36.

Figure 26A:
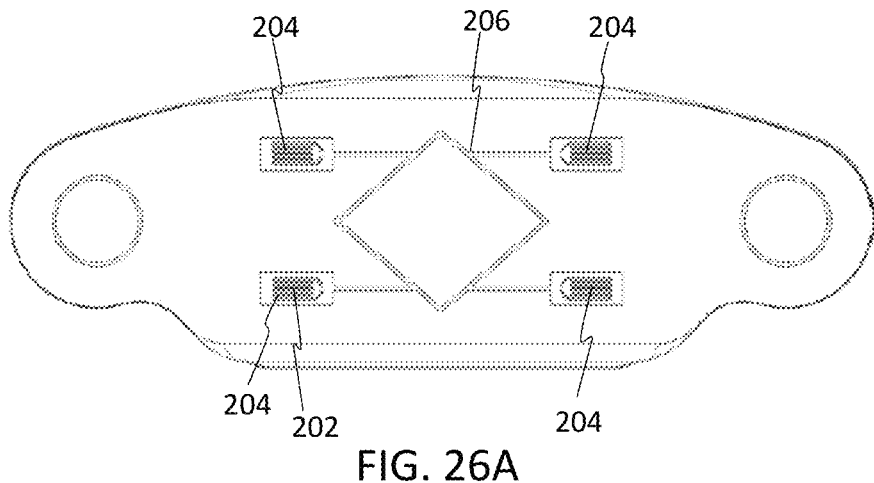
FIGS. 26A-26C show alternative arrangements for the strain gauges and circuitry configurations.
Figure 26B:
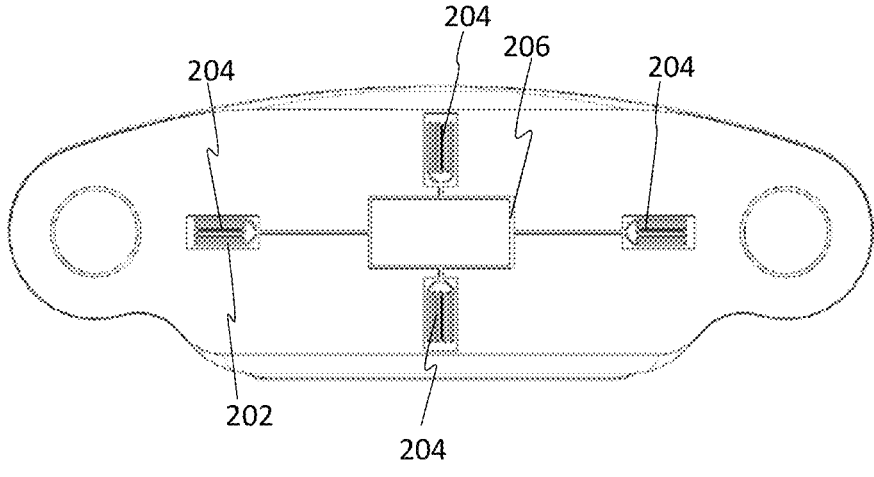
Figure 26C:
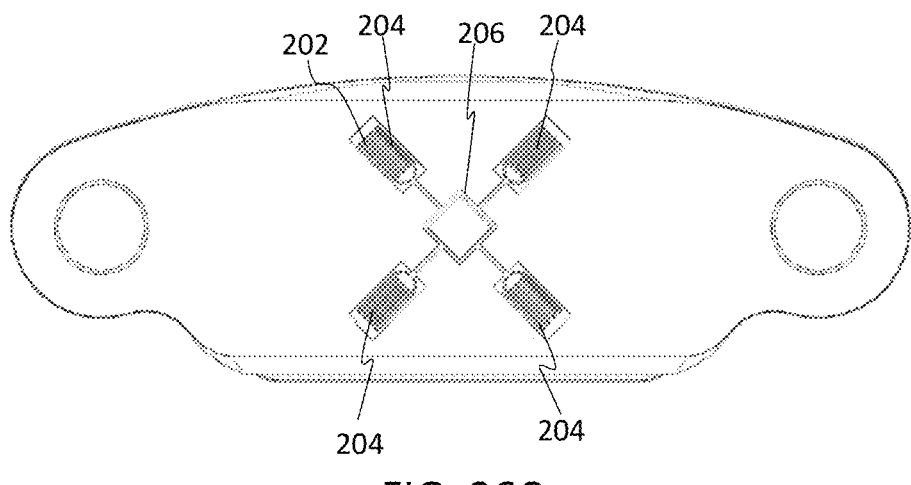
Figures 27A, 27B, 27C, 27D:
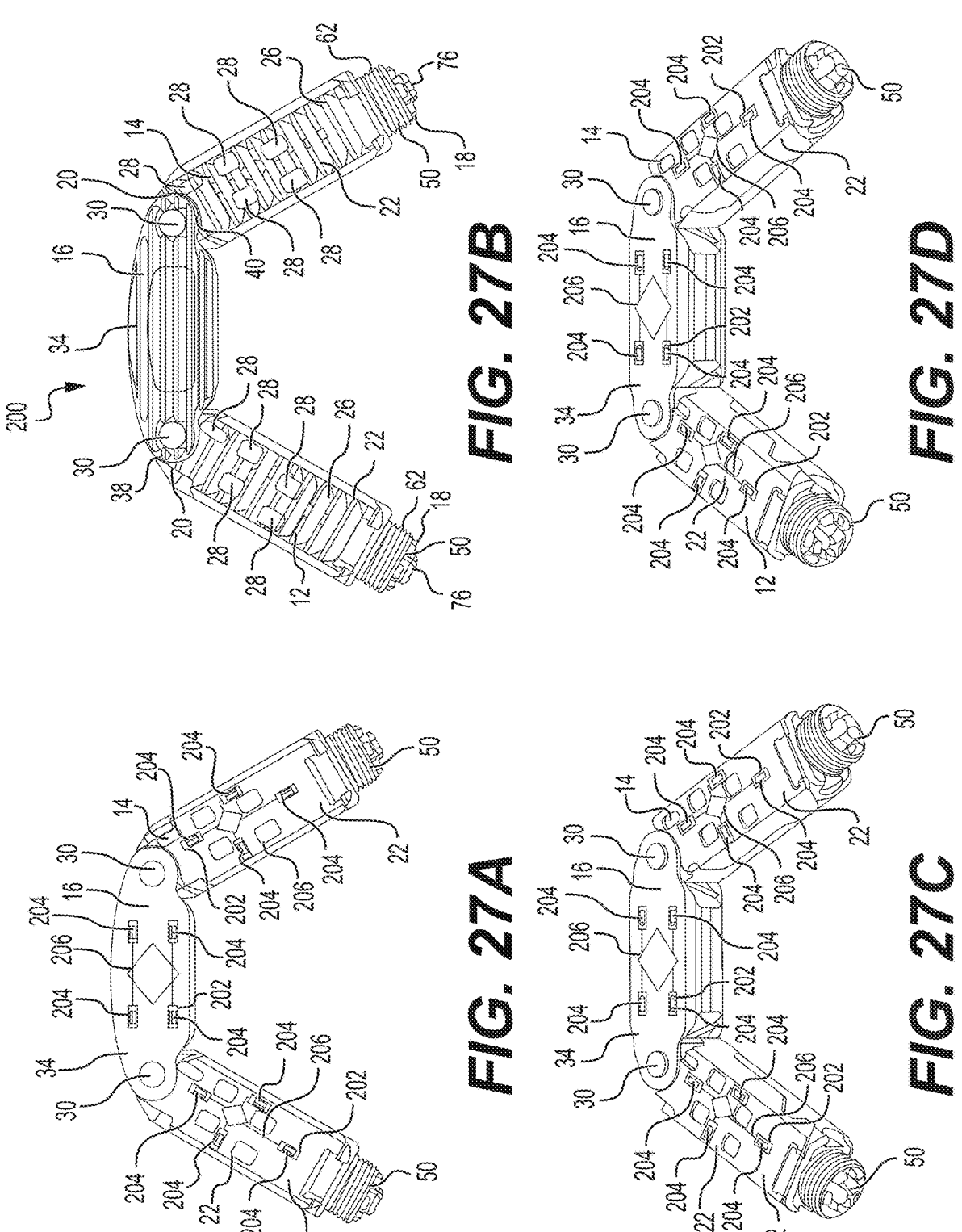
FIGS. 27A-27D show an embodiment of the implant with various strain gauges embedded in the endplates and link plates.
Figure 28A:
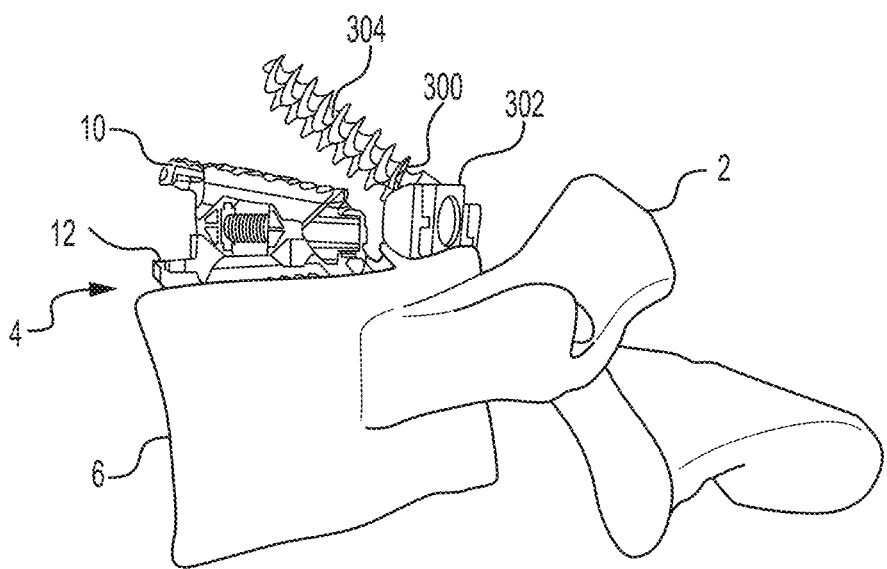
FIGS. 28A-28D show lateral, posterior, axial, and anterior perspective views, respectively, of the expandable fusion device with a supplemental intradiscal plating system according to one embodiment positioned in the disc space between adjacent vertebrae (the upper vertebra is omitted for clarity)
Figure 28B:
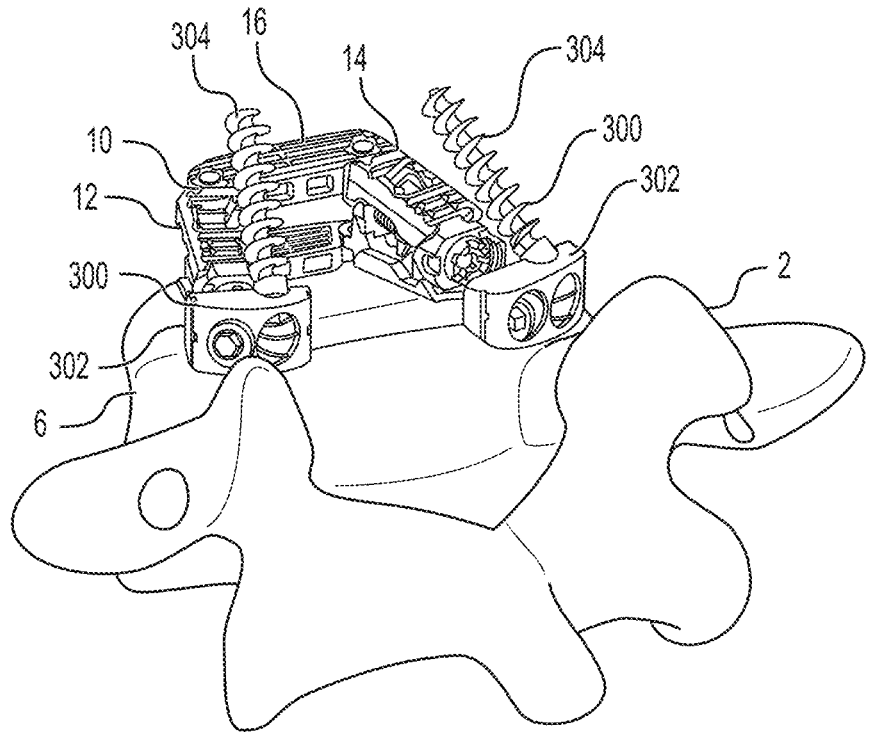
Figure 28C:
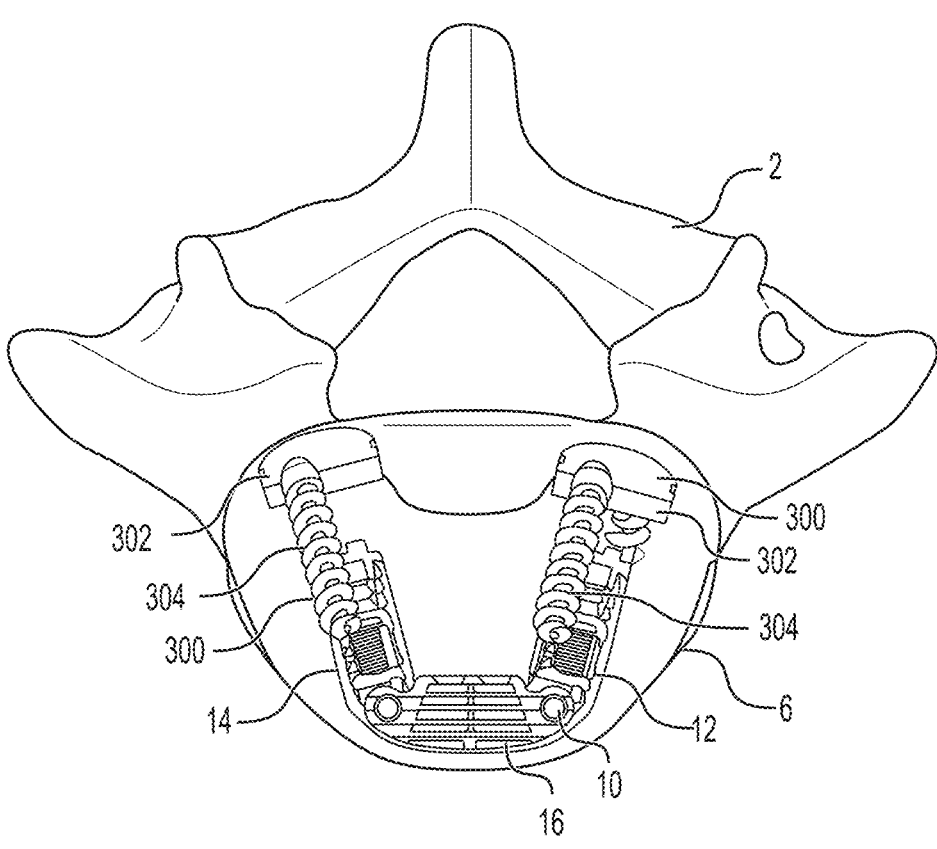
Figure 28D:
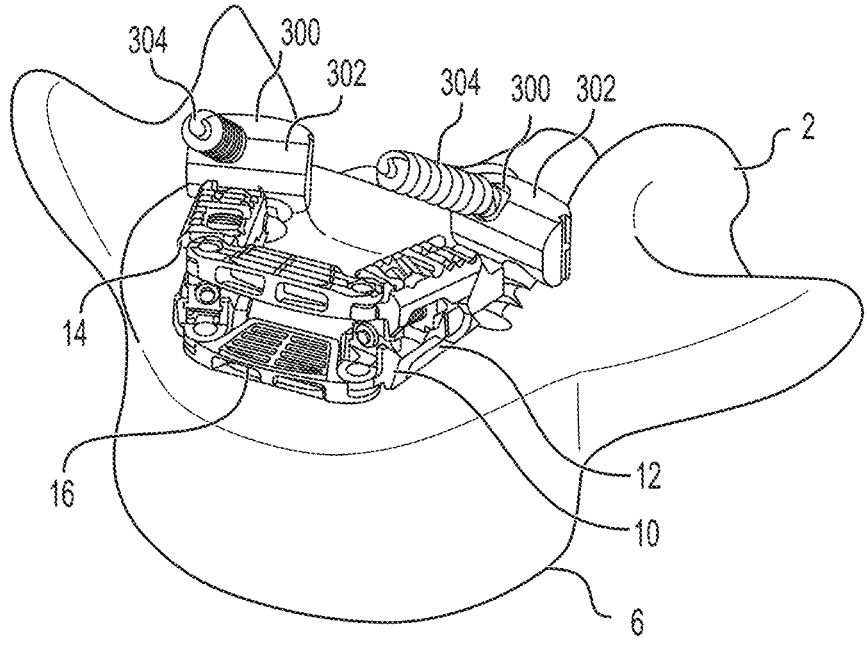

As shown in FIGS. 26A-26C, alternative arrangements for the strain gauges 202 are shown. The strain gauge resistance changes may be measured in a bridge circuit 206 to allow for precise measurement of small resistance changes. The circuit 206 may include a full-bridge, half-bridge, or quarter-bridge circuit. In the embodiments shown, the circuit 206 is a full-bridge configuration, which may be more sensitive to resistance changes. The gauge 202 may include four sensors 204 connected to legs of the circuit 206. In FIG. 26A, a first pair of sensors 204 are aligned and a second pair of sensors 204 are aligned such that the first and second pairs of sensors 204 are arranged in parallel. In FIG. 26B, a first pair of sensors 204 are aligned and a second pair of sensors 204 are aligned such that the sensors 204 are arranged in perpendicular. In FIG. 26C, the full-bridge system has four strain gauge sensors 204 with an X-type configuration with each sensor 204 connected to the four legs of the bridge circuit 206.

As shown in FIGS. 27A-27D, a first type of strain gauge 202 may be provided on lateral legs 12, 14 and a second type of strain gauge 202 may be provided on link plates 16. The positions of the sensors 204 may be identified through different circuitries 206 designed to measure the forces acting on the endplates 22, 24 and/or link plates 34, 36 throughout the surface area of the implant 200. The expansion of the implant 200 in its final implanted position may be optimized with the strain gauges 202 to measure the forces registering contact with both the superior and inferior vertebral bodies.

The features of the embodiments described herein may provide one or more of the following advantages. The integrated 3D printed endplates with embedded sensors 204 may allow for endplates 22, 24 and/or link plates 34, 36 to be printed with embedded sensors 204 in a one step process. The strain gauges 202 may help to improve surgeon understanding of the forces that are acting on the interbody placement. The ability to measure forces acting on the implant 200 may allow for measurements in the change in electrical resistance to create an understanding of the external forces acting on the implant 200. Increased endplate-to-bone contact may result of the measurement capabilities to increase the equal distribution of contact with the vertebral body across the surface area of the implant 200.

Turning now to FIGS. 28-45, the expandable interbody fusion device 10 may be used alone or in combination with one or more intradiscal fixation implants. The intradiscal fixation implant may include supplemental fixation systems 300, 400 or integrated standalone fixation systems 350, 360, 460. The supplemental fixation system may include an intradiscal plating system 300, 400 with one or more flexible screws or anchors 304 or a splayed anchor 404, for example. The supplemental systems 300, 440 may work in concert with the expandable fusion device 10. The supplemental intradiscal systems may be introduced bilaterally, posterior to the interbody 10 and in the intradiscal space 4. The integrated systems 350, 360, 460 may integrate the anchors 304, 404 directly with the expandable device to provide for a standalone system. The fixation system may be inserted on the same trajectory and orientation as the interbody 10, whether the system is integrated or supplemental. The integrated standalone or supplemental systems may help to reduce iatrogenic effects caused by disruption and violation of posterior structural anatomy and soft tissue.

With emphasis on FIGS. 28-36, supplemental intradiscal fixation implants 300 are shown according to one embodiment. As shown in FIGS. 28A-28D, the entire fixation system may include expandable interbody implant 10 and a pair of intradiscal fixation implants 300 for fusing two adjacent vertebrae 2 (only the inferior vertebra 2 is shown for clarity). The expandable interbody implant 10 is positioned in the disc space 4 between the superior and inferior vertebral bodies 6. The interbody implant 10 may be placed along the apophyseal ring for cortical bone support. The expandable interbody implant 10 may include dual, independent expansion and angulation to adjust lordosis and/or coronal balance, thereby allowing for restoration of spinal anatomical alignment.

Each supplemental intradiscal fixation implant 300 may include a plate 302 and one or more anchors 304. The plate 302 is configured to be positioned posteriorly in the disc space 4 and the anchors 304 may be angled to protrude upwardly and/or downwardly into the adjacent vertebral bodies 6, thereby providing additional stability. First and second supplemental fixation implants 300 may be inserted bilaterally into the disc space 4 and secured with the anchors 304. The overall fixation system may provide for superior segmental correction from stabilization device 10 with independently controlled sagittal and coronal correction and increased stability from supplemental fixation 300. The placement and proper insertion of supplemental fixation systems 300 provides for quality bone purchase, avoidance of violating the expanded interbody spacer 10, and provides a positive contribution to the overall construct stability.

Figure 29A:
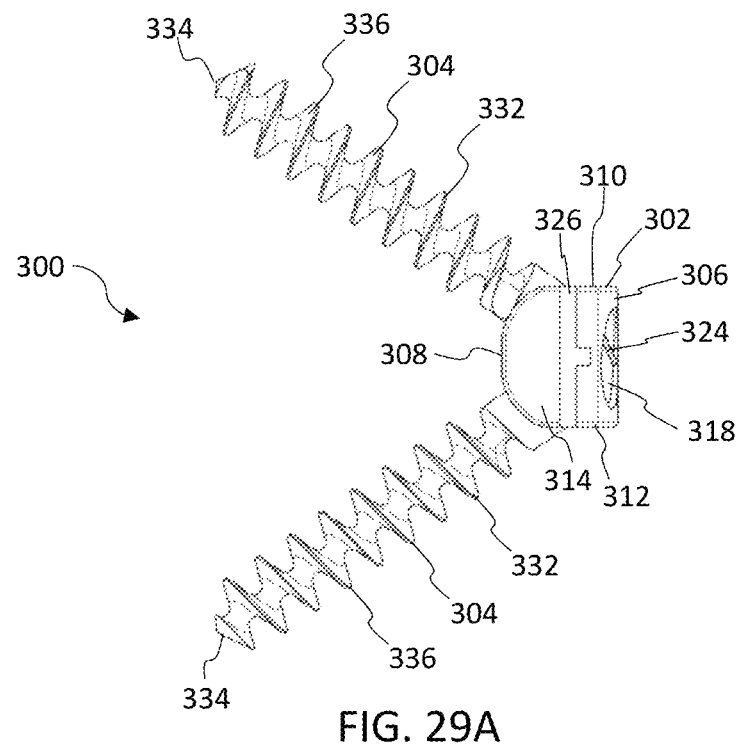
FIGS. 29A-29C show side, front, and rear views, respectively, of the supplemental intradiscal plating system according to one embodiment.
Figures 29B, 29C:
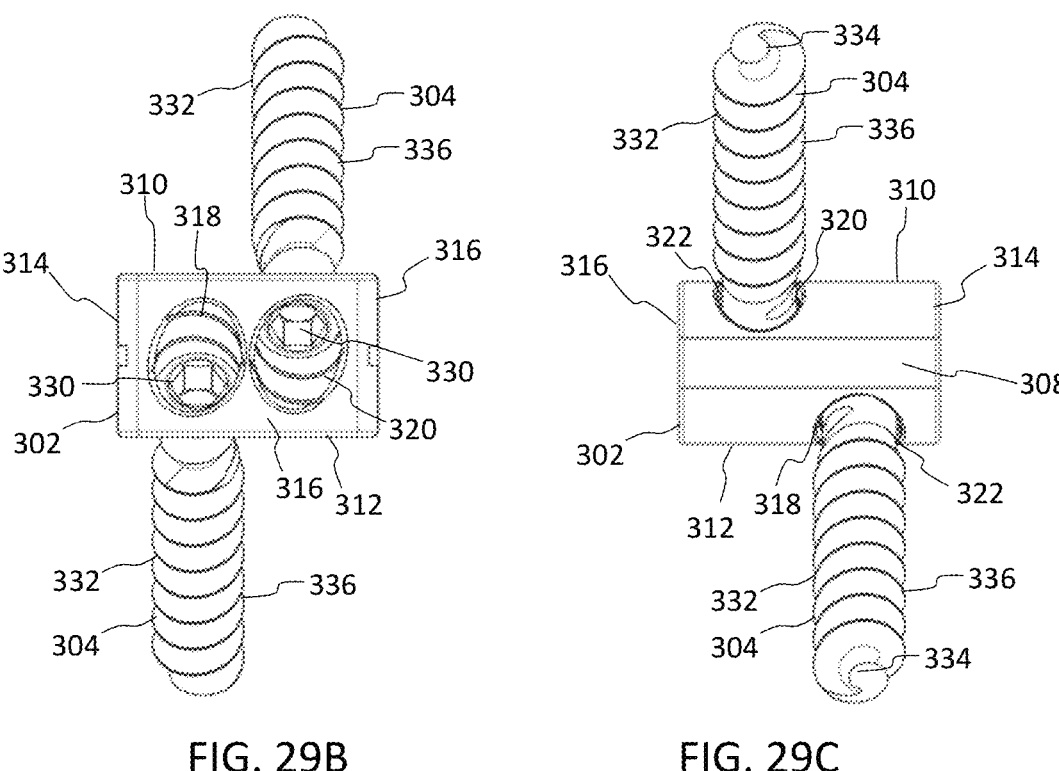
Figures 30A, 30B:
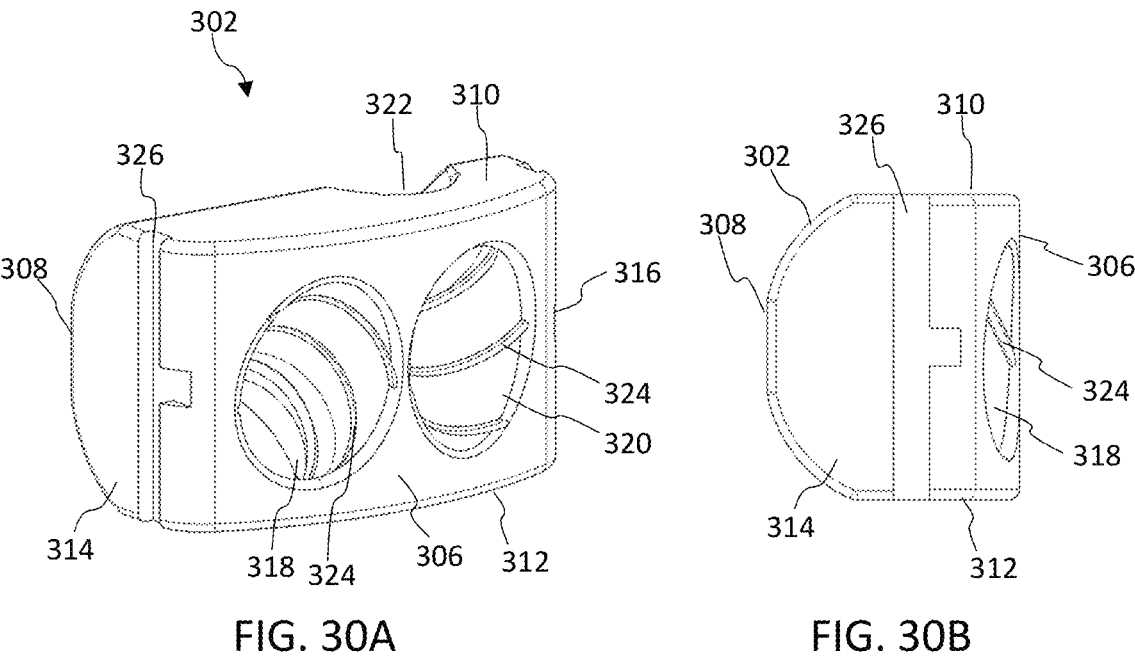
FIGS. 30A-30D show perspective, side, front, and cross-sectional views, respectively, of the plate used in the intradiscal plating system according to one embodiment.
Figures 30C, 30D:
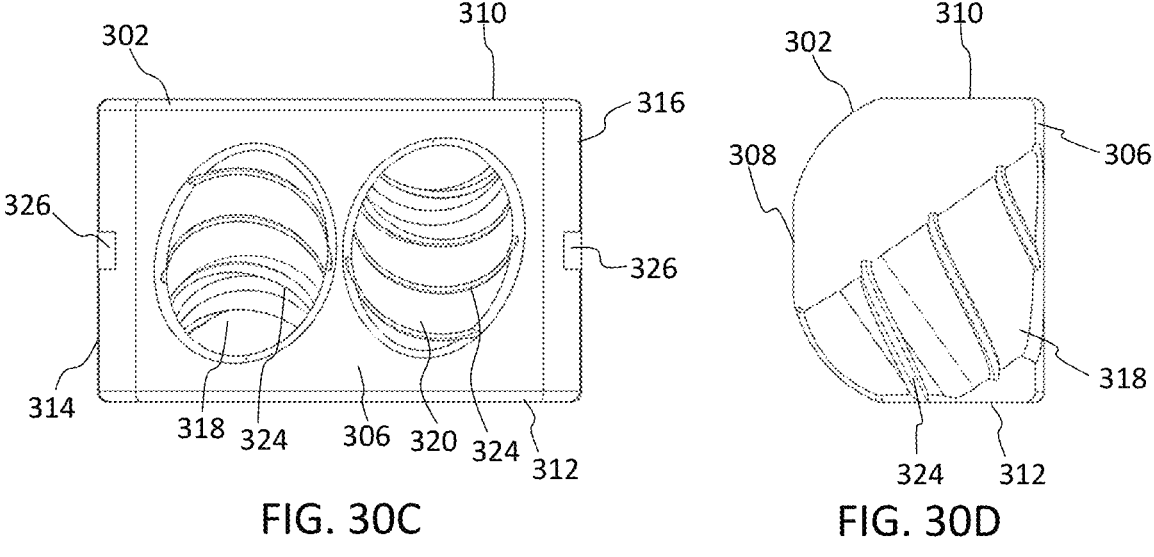

With further emphasis on FIGS. 29A-29C, the supplemental fixation system 300 includes plate 302 and anchors 304. As best seen in FIGS. 30A-30D, the plate 302 includes a body with front face 306 and opposite rear face 308, top or upper face 310 and bottom or lower face 312, and opposing sides 314, 316. The front face 306 may be curved between the sides 314, 316, for example, with a convex curve. The top and bottom faces 312 may be generally planar. The rear face 308 may bump out with a planar section between first and second curved portions. The convex curves of the rear face 308 may connect the upper and lower faces 310, 312, for example. The side faces 314, 316 may be generally planar and parallel to one another. It will be appreciated that any of the plate faces may be flat, curved, or suitably contoured to fit in the disc space 4.

First and second openings 318, 320 extend through the plate 302 between the front and rear faces 306, 308. The first opening 318 may be angled such that the opening 318 is oriented downwardly and the second opening 320 may be angled such that the opening 320 is oriented upwardly. The first and second openings 318, 320 are configured to retain anchors 304. One or more cutouts 322 may be provided in the upper and/or lower faces 310, 312 to accommodate the body of the anchor 304. The plates 302 may include threaded and/or non-threaded openings 318, 320. In one embodiment, the openings 318, 320 define one or more threads 324 configured to mate with corresponding threads 336 on the anchor 304, thereby guiding insertion of the anchors 304.

The side surfaces 314, 316 may define one or more instrument retention slots 326. For example, an elongate slot 326 may be provided between the upper face 310 and the lower face 312. The slot 326 may include a T-shaped groove with a central recess extending toward the front face 306. The instrument retention slot 326 may be configured to be gripped by an insertion instrument, for example. It will be appreciated that the instrument retention slots 326 may be otherwise suitably configured for this purpose.

The anchor 304 may include screws, fasteners, clamps, or the like configured to engage bone. With further emphasis on the embodiment shown in FIGS. 31A-31C, the anchor 304 may include a screw having a head 330 and a shaft 332 extending from the head 330 to a distal end 334. The distal end 334 may include a pointed sharp tip, blunt end, or other suitable shape configured to engage bone. The shaft 332 may include one or more threads 336. It will be appreciated that the threaded shaft 336 may have a number of different features, such as thread pitch, shaft diameter to thread diameter, overall shaft shape, and the like.

The screws 304 may include fixed and variable angles screws. Variable angle screws may not exceed 10° conical angulation, for example. The screw head 330 may have any general shape, but in one embodiment, at least a portion of the screw head 330 may have a curved surface in order to allow for rotational movement and/or angular adjustment of the anchor 304 with respect to the plate 302. For example, at least a portion of the screw head 330 may be rounded, for example, as a portion of a sphere. The screw head 330 may have a tool engagement surface 338, for example, that can be engaged by a screw-driving instrument or other device. In one embodiment, the bone screw head 330 has a hex recess 338 for driving the screw 304 into bone. It will be appreciated that any suitably shaped tool engagement surface 338 may be provided.

Figure 31A:
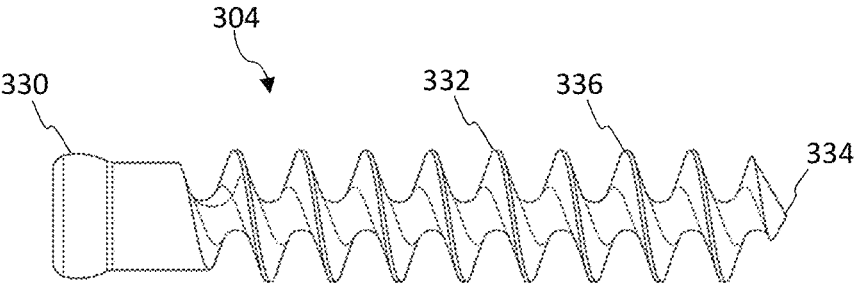
FIGS. 31A-31C show straight and bent configurations of flexible screws used in the intradiscal plating system according to one embodiment.
Figure 31B:
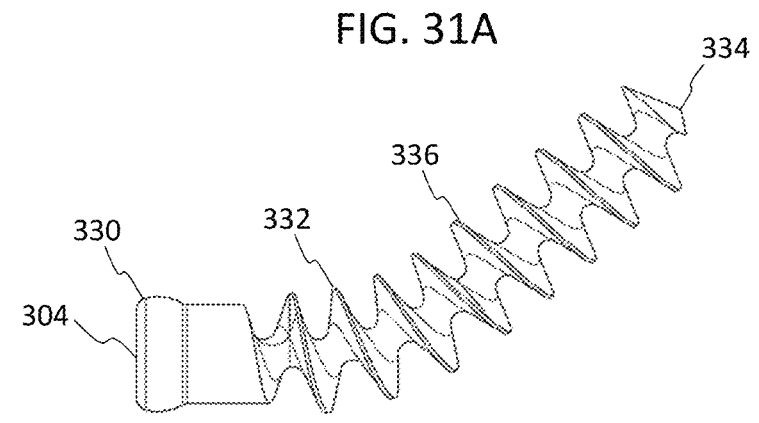
Figure 31C:
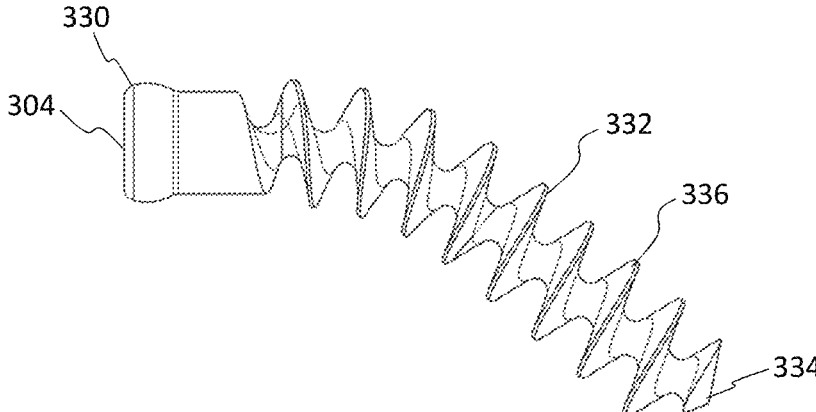

According to one embodiment, the anchor 304 is flexible such that the anchor 304 can be inserted in a straight profile, bent, and then driven at an angle into bone. For example, the shaft 332 or a portion thereof is flexible along its length to allow for bending of the anchor 304 as it passes through the plate 302. FIG. 31A shows the anchor 304 in a straight configuration and FIGS. 31B and 31C show the anchor 304 in a bent configuration. The anchor 304 may be composed of a nickel titanium alloy, such as nitinol or other shape-memory material, which allows the anchor 304 to bend into the curved state. The super elasticity of nitinol may allow for the material to be drawn into the bent or curved configuration from its natural state. In its relaxed state, the nitinol anchor 304 may have a straight profile. In its bent state, the nitinol anchor 304 may have a curve or bend up to 45°, for example. The shape memory effect and superelasticity allow for the material to deform in shape and recover its original shape.

The diameter and thread profile of the flexible nitinol screw 304 may be controlled to improve the super elastic properties in proportion to its strength. The anchor 304 may be driven in a straight (0° or curved state)(≤45° in a direction to allow for the screw 304 to directionally translate while threading into patient anatomy. A variety of intradiscal plating offerings may be accessible for varying patient anatomy to help preserve the posterior height and improve mechanically applied posterior compression. This also reduces the likelihood of pushing the lumbar spine into kyphosis.

Figure 32A:
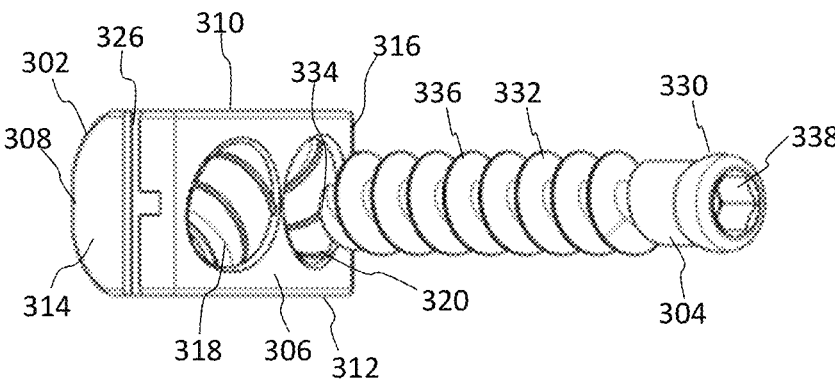
FIGS. 32A-32E show steps for deploying the flexible screws of the intradiscal fixation system according to one embodiment.
Figure 32B:
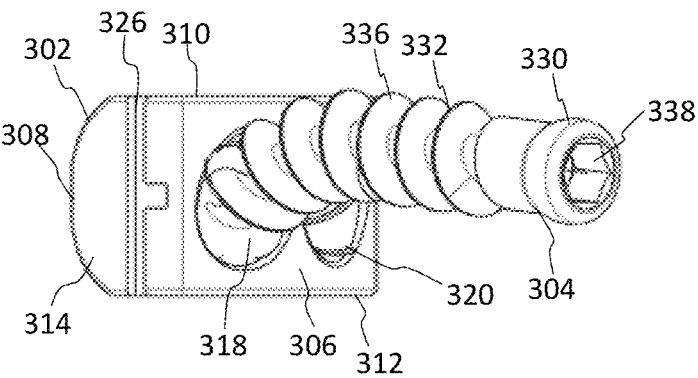
Figure 32C:
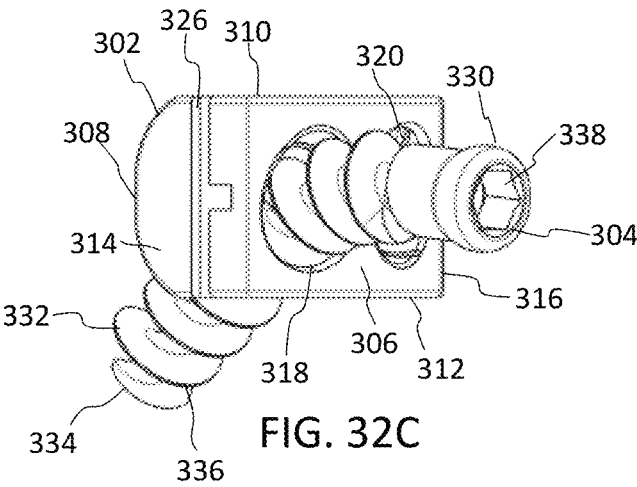
Figures 32D, 32E:
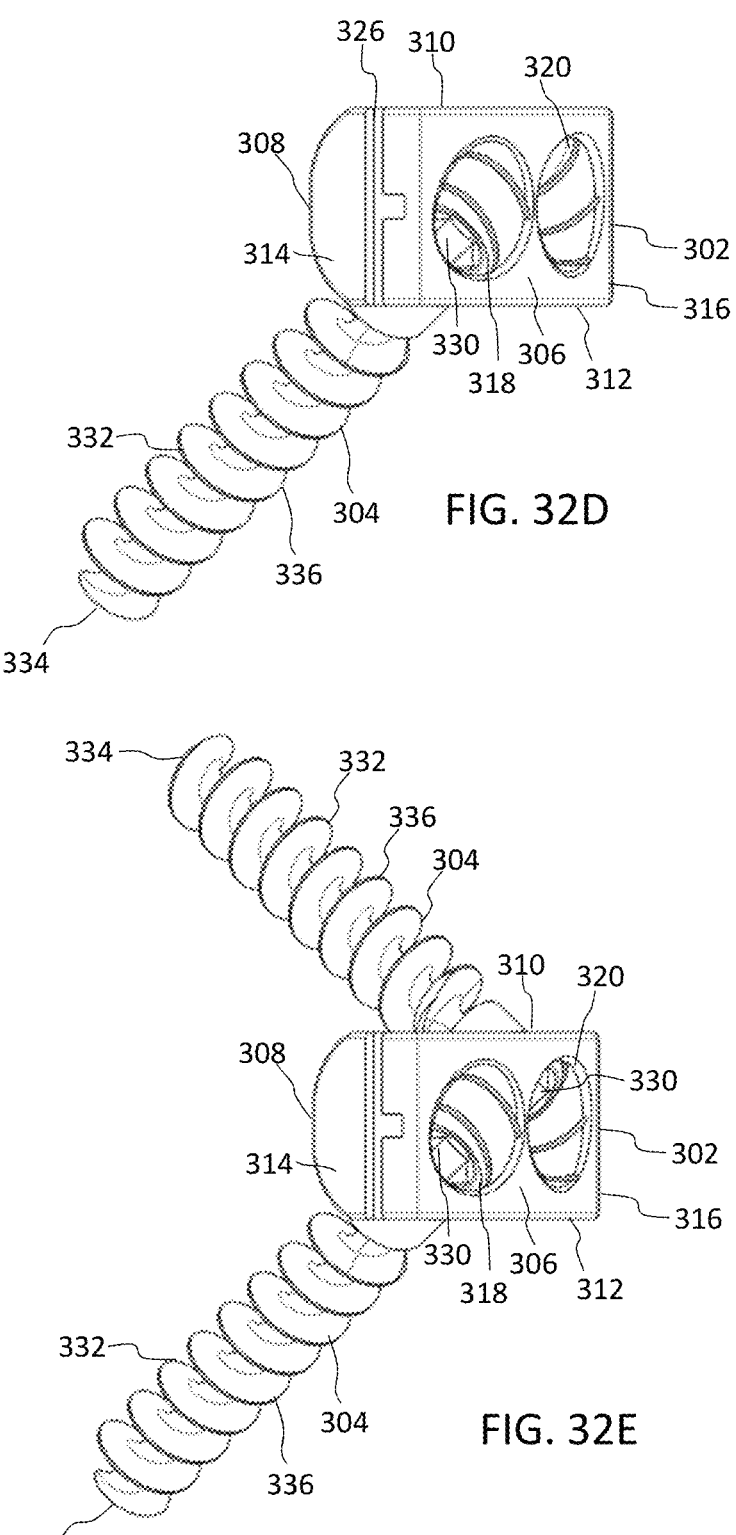

With further emphasis on FIGS. 32A-32E, insertion of the anchors 304 into plate 302 are shown according to one embodiment. In FIG. 32A, the distal end 334 of the anchor 304 is aligned with the first opening 318. The anchor 304 is in the straight configuration. In FIG. 32B, the distal end 334 of the anchor 304 enters opening 318, thereby forcing the tip of the anchor 304 to bend. The threads 336 of the anchor 304 may engage with the threads 324 in the opening 318 to guide the anchor 304 and facilitate bending of the shaft 332. In FIG. 32C, the anchor 304 continues to travel through opening 318 such that the shaft 332 is bent as it is driven into bone. FIG. 32D shows the anchor 304 fully inserted into opening 318 such that the head 330 is engaged with the opening 318. The anchor 302 returns to the straight configuration. The second anchor 304 is inserted into second opening 320 in a similar manner with the anchor 304 bending during insertion as it passes through the plate 302 and straightening afterwards. FIG. 32E shows the final configuration with both anchors 304 returned to the straight configurations: the first anchor 304 angled downwardly into the inferior vertebral body 6 and the second anchor 304 angled upwardly into the superior vertebral body 6. It will be appreciated that the number, angle, and position of anchors 304 may be modified to achieve the desired attachment to bone.

When inserting flexible screws 304, the flexible screws 304 may be inserted on a low-profile trajectory (not exceeding the height of plating and/or inserter profile). The flexible screws 304 may be forced into a predetermined bend radius that angles the inferior and superior screws. For example, the predetermined bend radius may be between about 30°-45° relative to the cephalad-caudal plane. Screws 304 may be driven individually or simultaneously depending on the user's preference and the type of inserter and/or driver being used. The flexible screws 304 may self-lock once fully driven into intradiscal plating 302. Screw backout would require movement of the patient that drives the screw to rotate and bend simultaneously, which is unlikely. Movement is possible when the inserter, driver, and plating are used in place to mechanically drive the intradiscal fixation system. The flexible screw profile may provide for screw lagging capabilities that help to mechanically drive posterior compression to increase interbody-endplate contact, which in turn improves construct stability and spinal correction.

When fully assembled, the intradiscal fixation system 300 may be inserted bilaterally on the posterior edge of the vertebral body disc space 4. Because the anchors 304 are flexible, they can be inserted through a low, straight profile, bent and then driven at an angle when paired with the inserter, driver and intradiscal plating 302. The placement and proper insertion of the fixation system 300 provides quality bone purchase, avoidance of violating the expanded interbody spacer 10, and provides a positive contribution to the overall construct stability. Multiple screw thread geometries, lengths, and diameters can be paired with various plating offerings in terms of height and screw angulation to help improve bone purchase and ease of insertion to promote fixation strength and stability.

Figure 33:
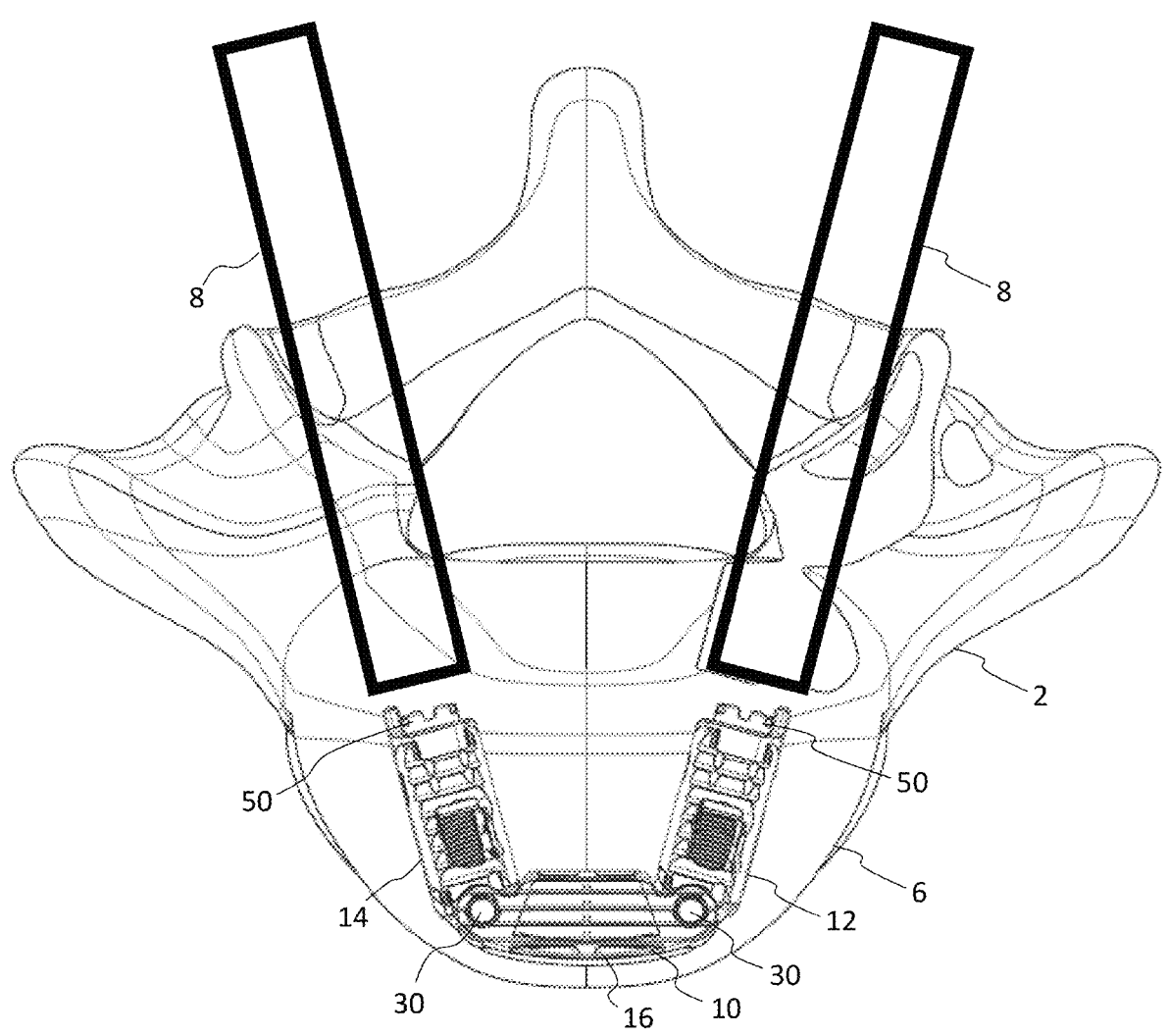
FIG. 33 is a top-down view of the expandable fusion device positioned in the disc space and the minimally invasive working corridors that may be used to access the disc space according to one embodiment.
Figure 34:
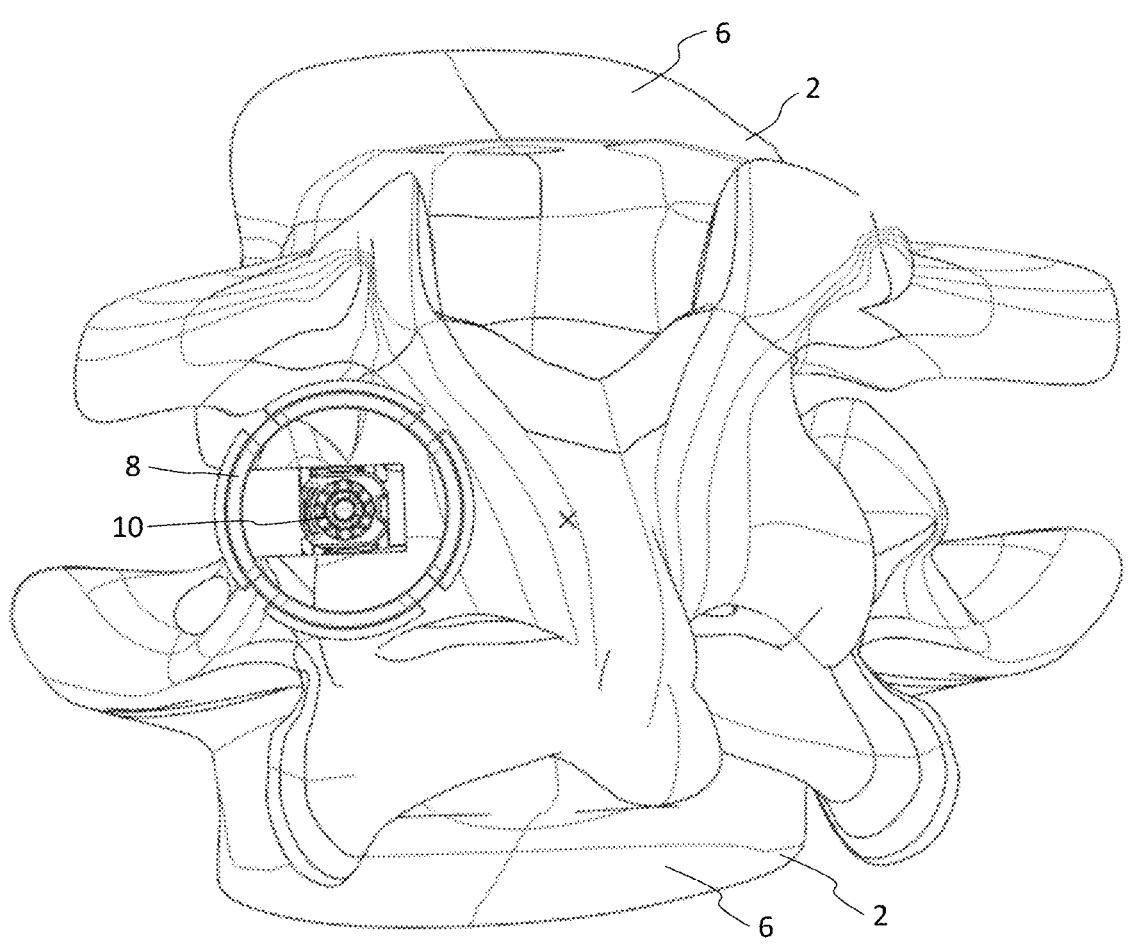
FIG. 34 is a posterior perspective view of one working corridor to access the disc space and install the expandable fusion device and intradiscal fixation system.
Figure 35A:
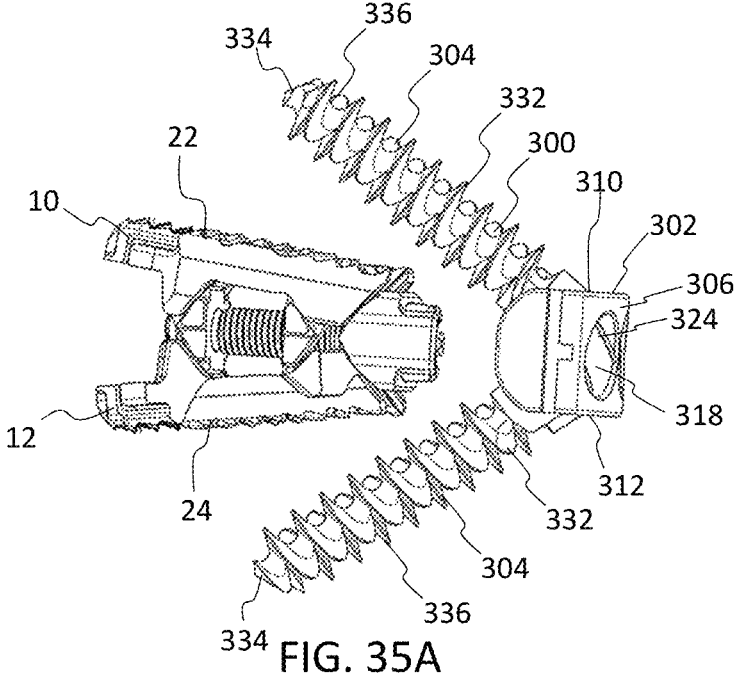
FIGS. 35A-35D show side, posterior, top, and anterior perspective views, respectively, of the expandable fusion device and supplemental intradiscal plating system according to one embodiment.
Figure 35B:
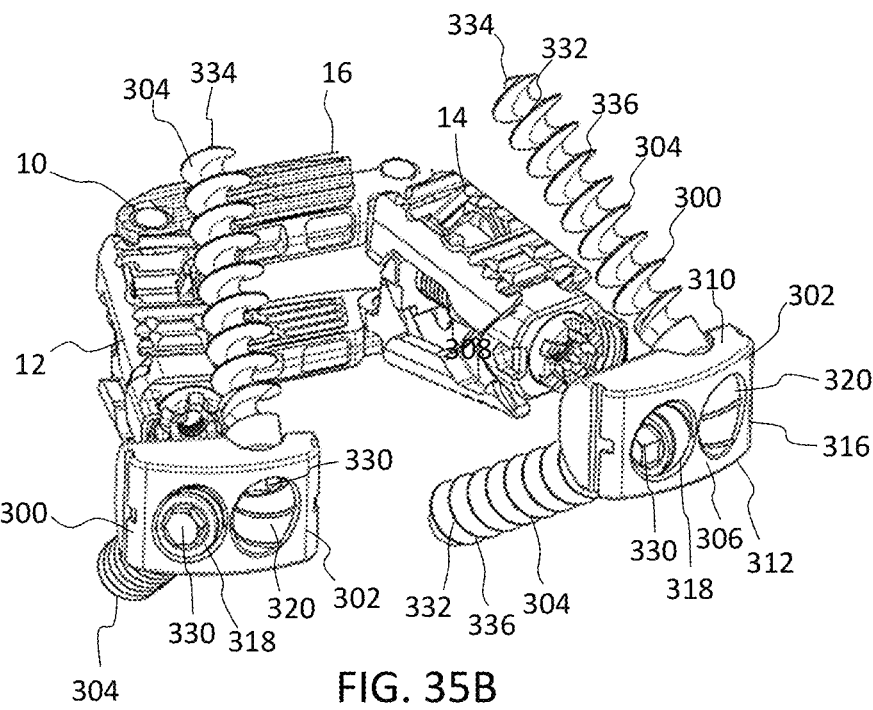
Figure 35C:
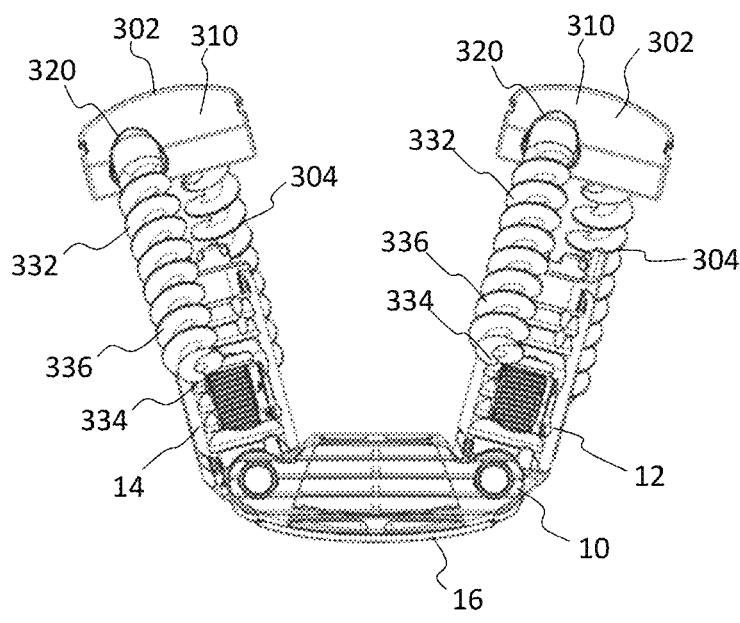
Figure 35D:
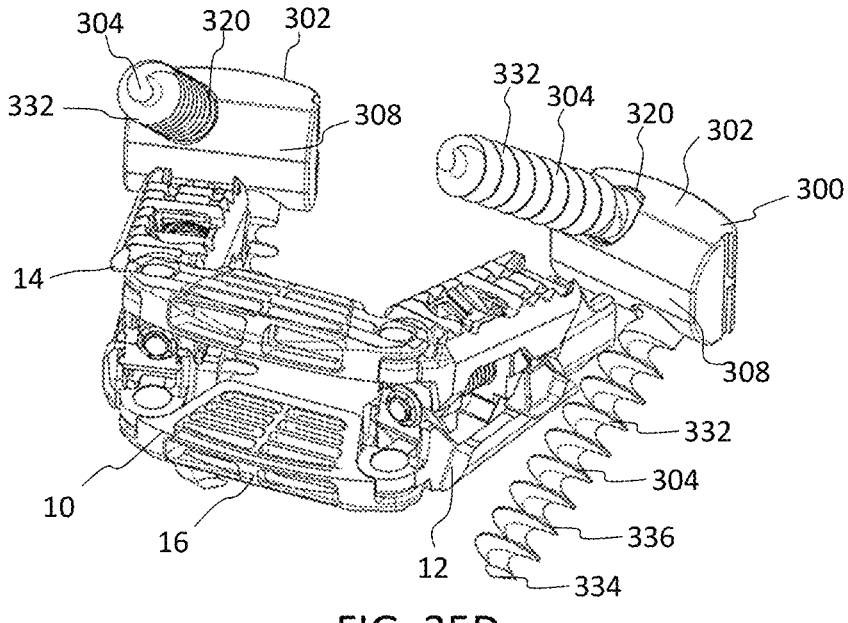
Figure 36A:
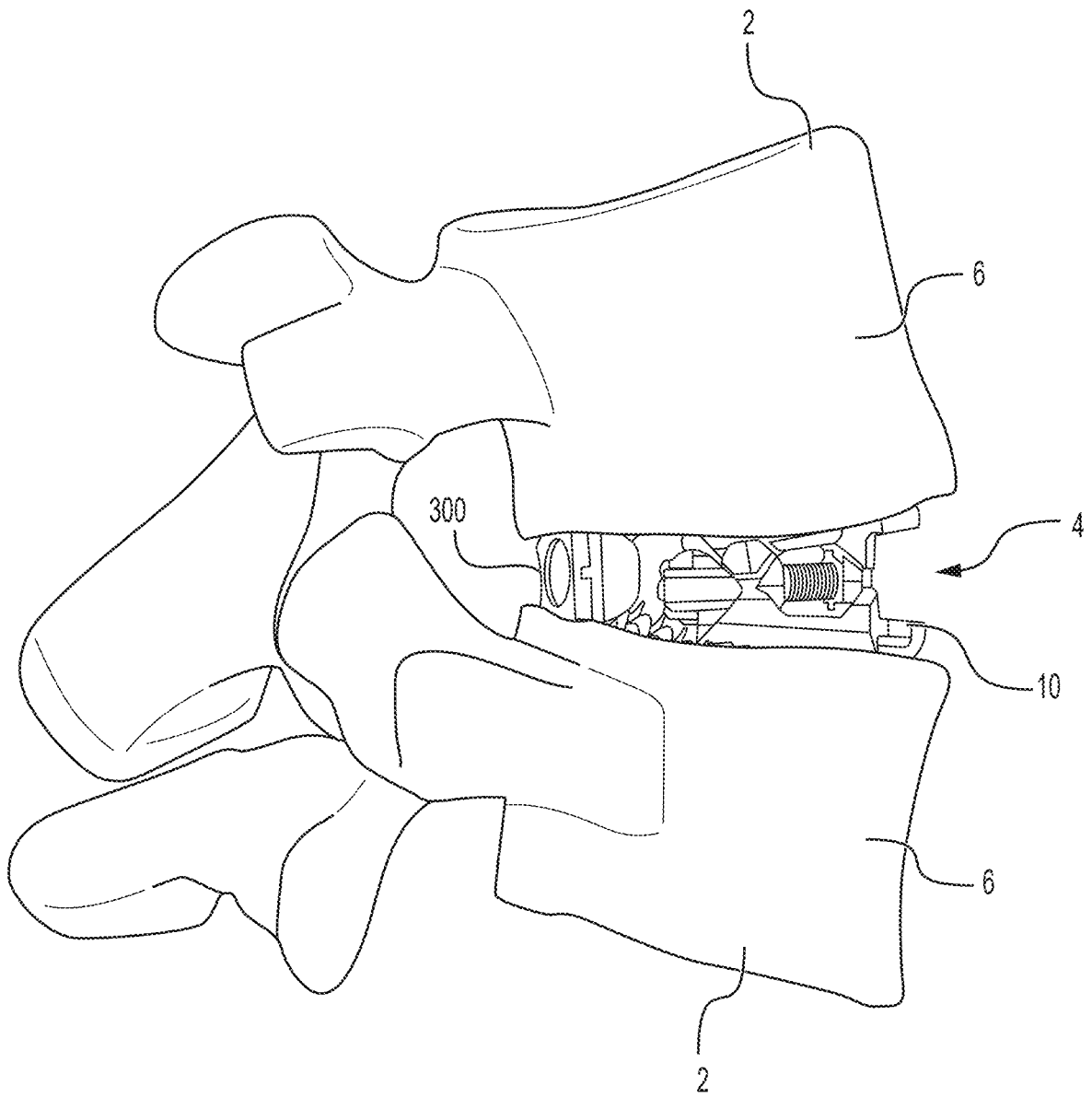
FIGS. 36A-36E show lateral, posterior, top-down, anterior perspective views, respectively, of the expandable fusion device and supplemental intradiscal plating system installed bilaterally into the disc space between adjacent vertebrae.
Figure 36B:
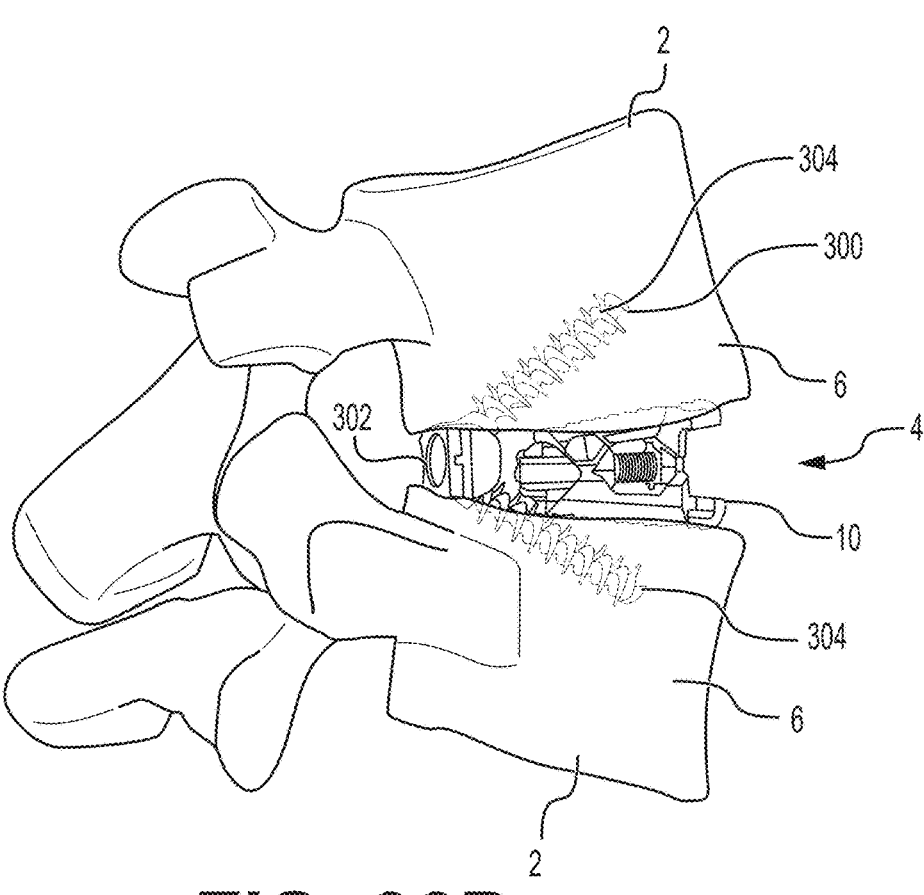
Figure 36C:
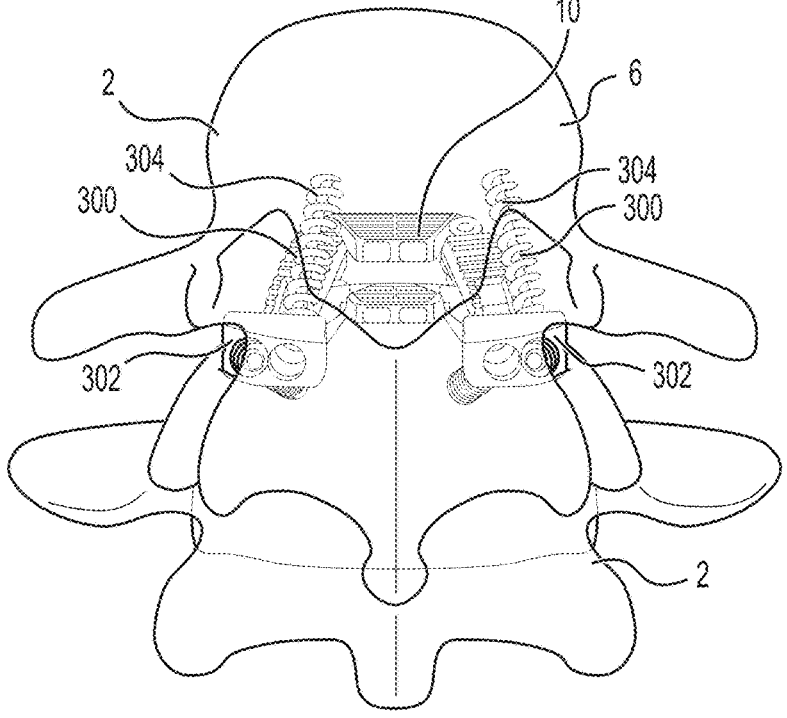
Figure 36D:
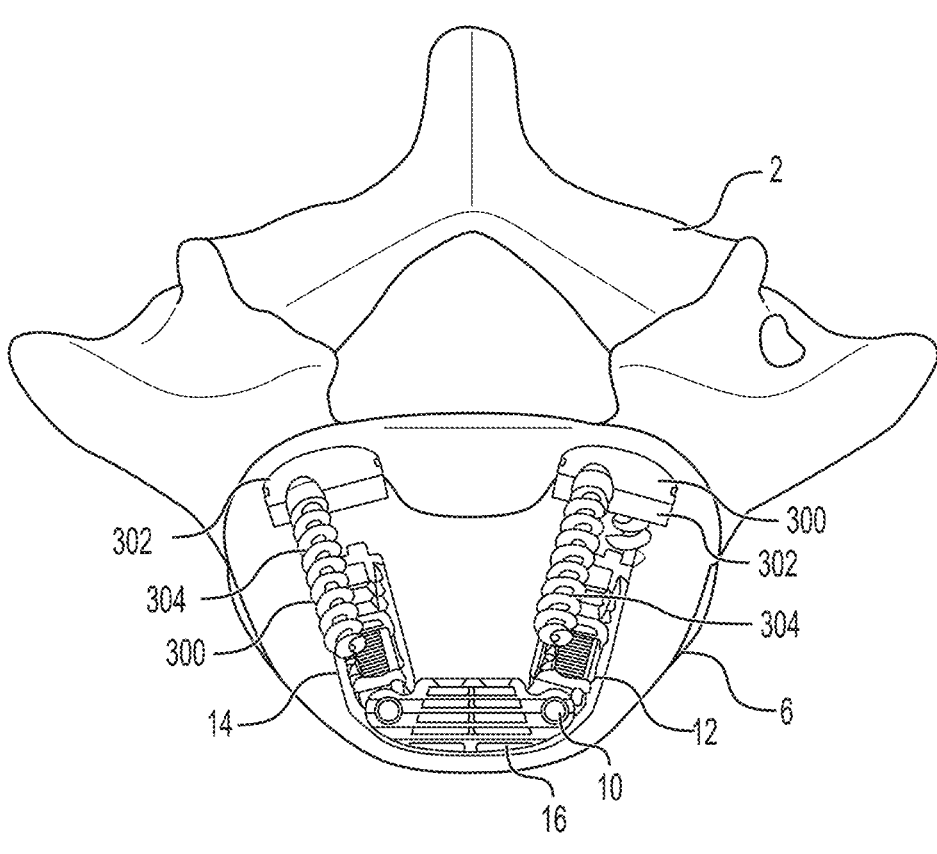
Figure 36E:
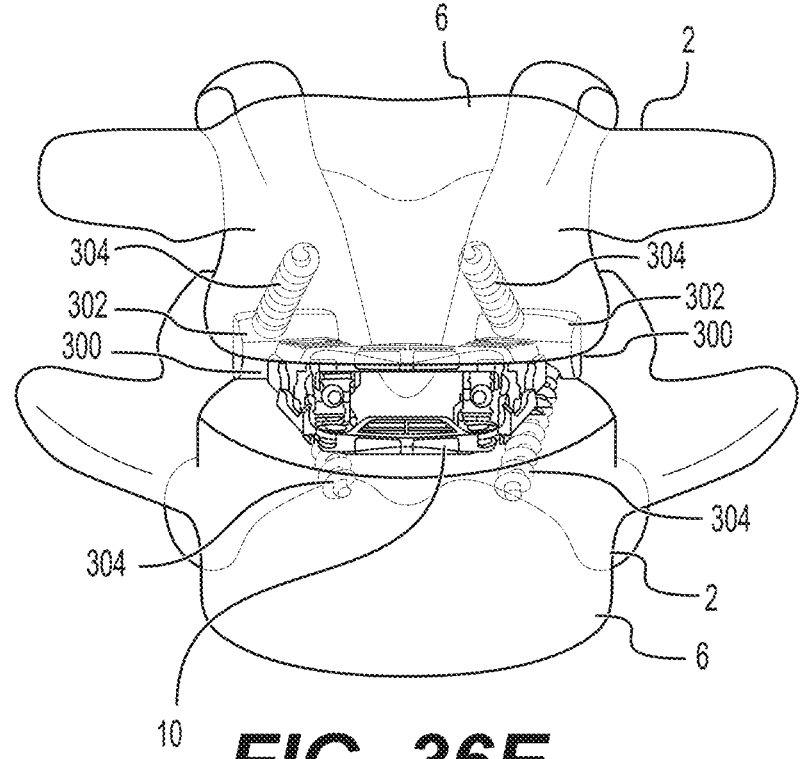
Figure 37A:
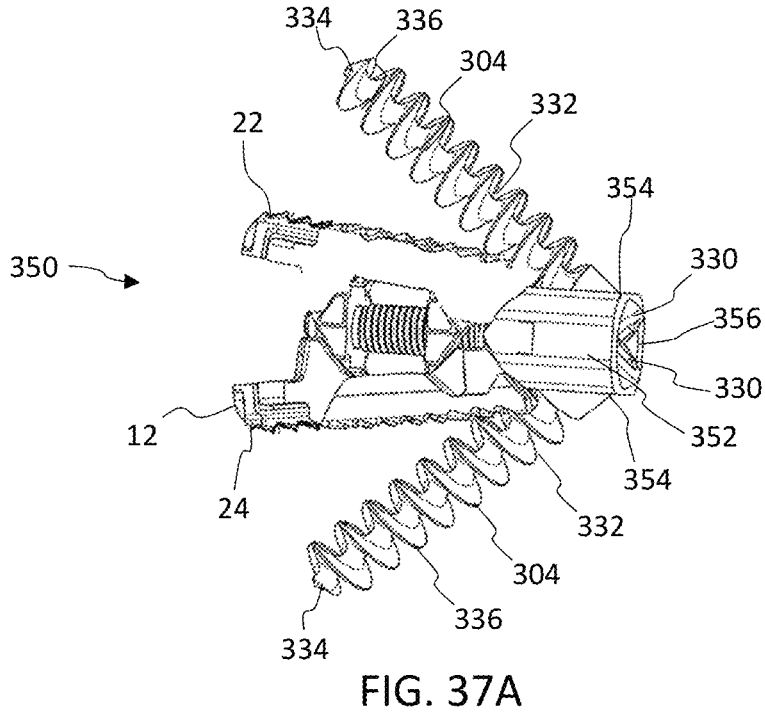
FIGS. 37A-37D show side, top, anterior, and posterior views, respectively, of the intradiscal fixation system integrated with the expandable fusion device according to one embodiment.
Figure 37B:
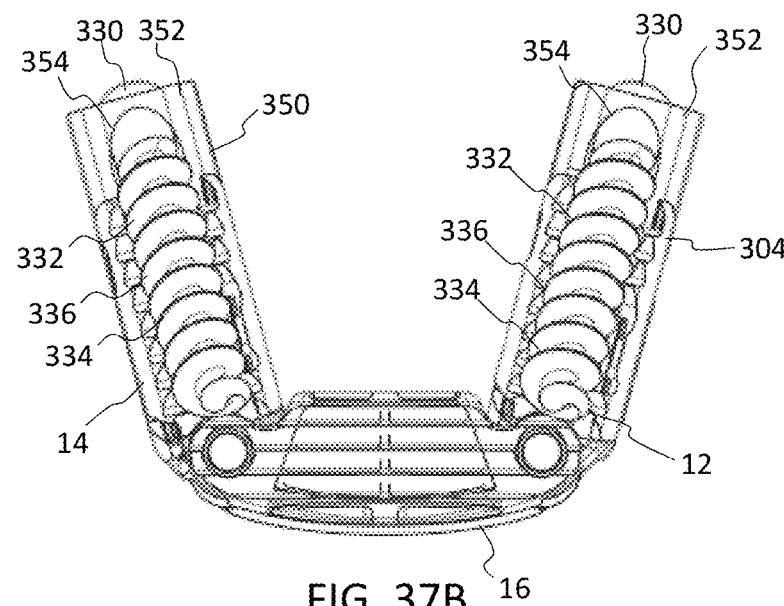
Figure 37C:
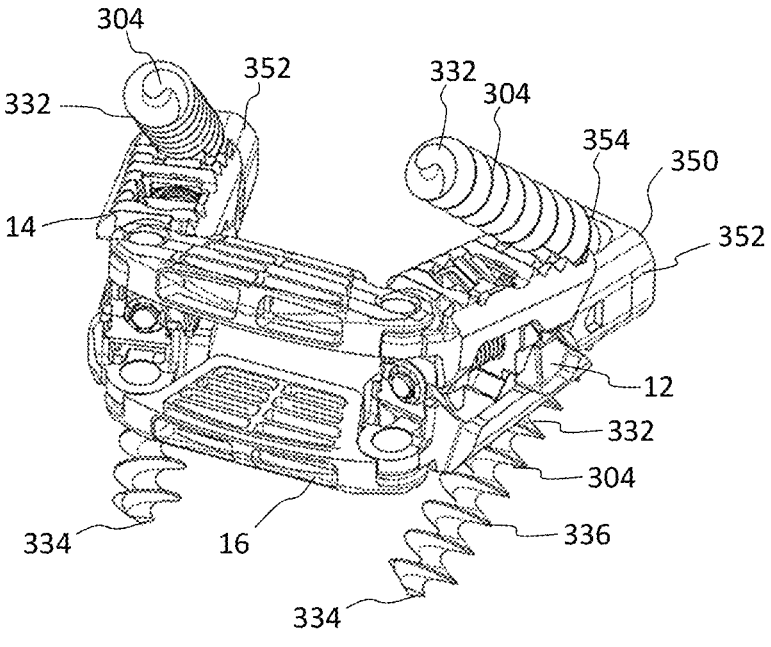
Figure 37D:
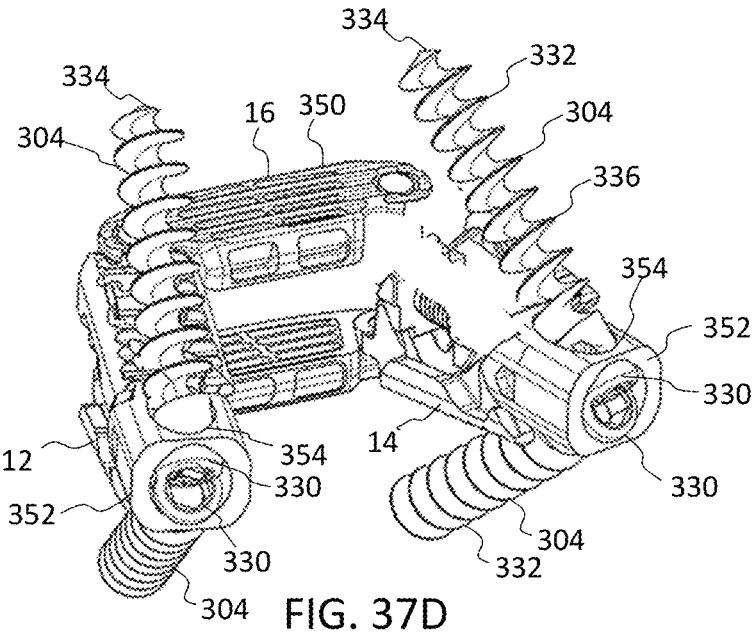
Figure 38A:
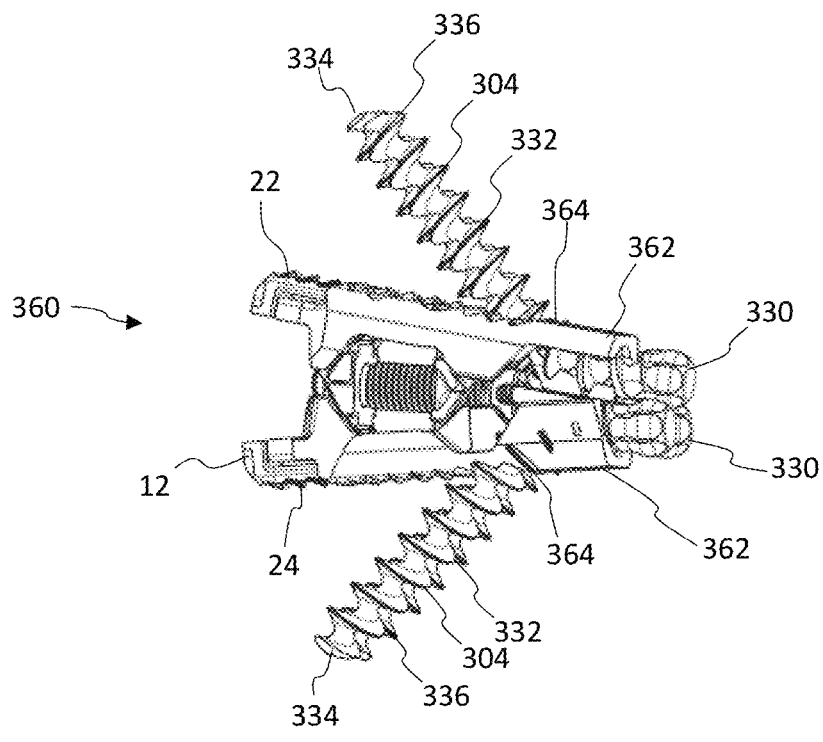
FIGS. 38A-38D show side, top, anterior, and posterior views, respectively, of the intradiscal fixation system integrated with the expandable fusion device according to another embodiment.
Figure 38B:
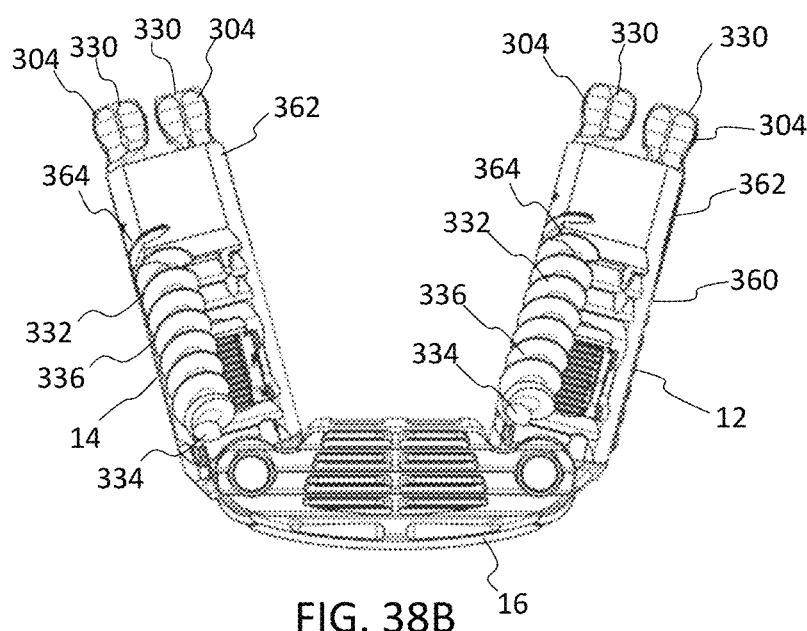
Figure 38C:
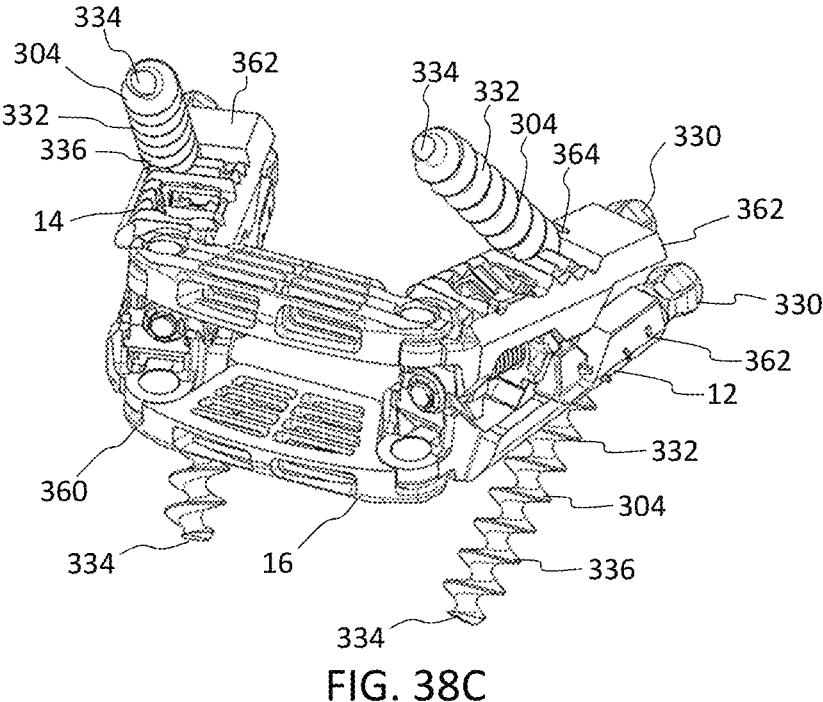
Figure 38D:
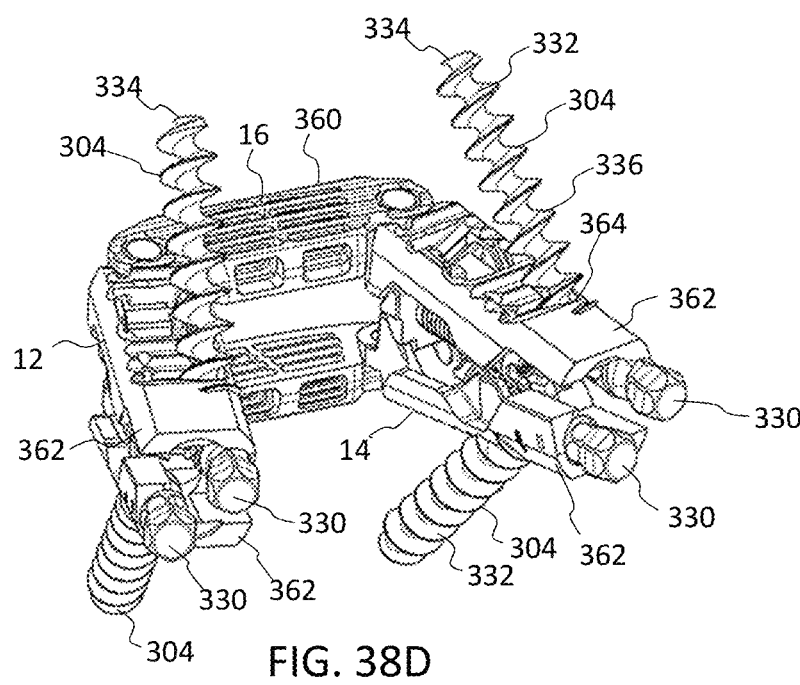
Figure 39A:
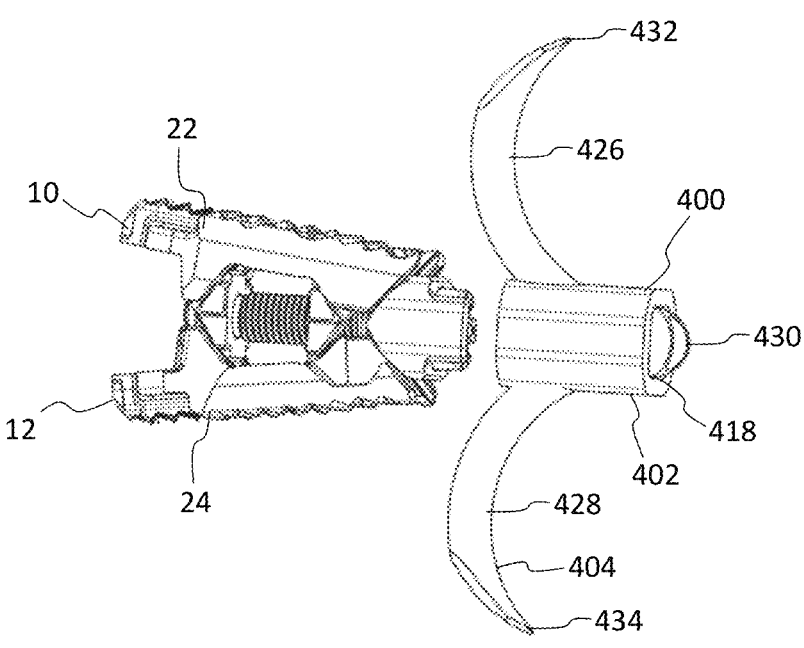
FIGS. 39A-39D show side, top, posterior, and anterior views, respectively, of the expandable fusion device with a supplemental intradiscal plating system having a splayed anchor according to one embodiment.
Figure 39B:
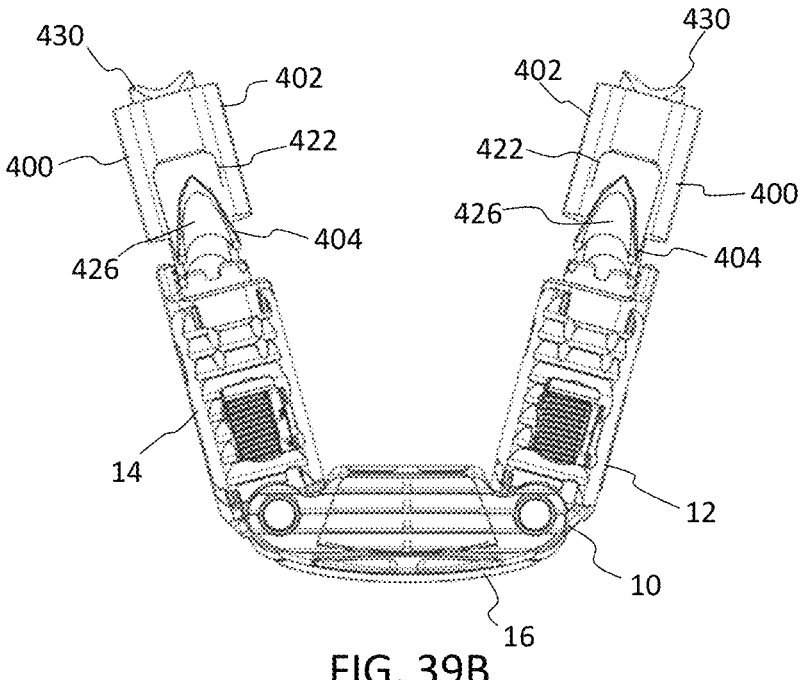
Figure 39C:
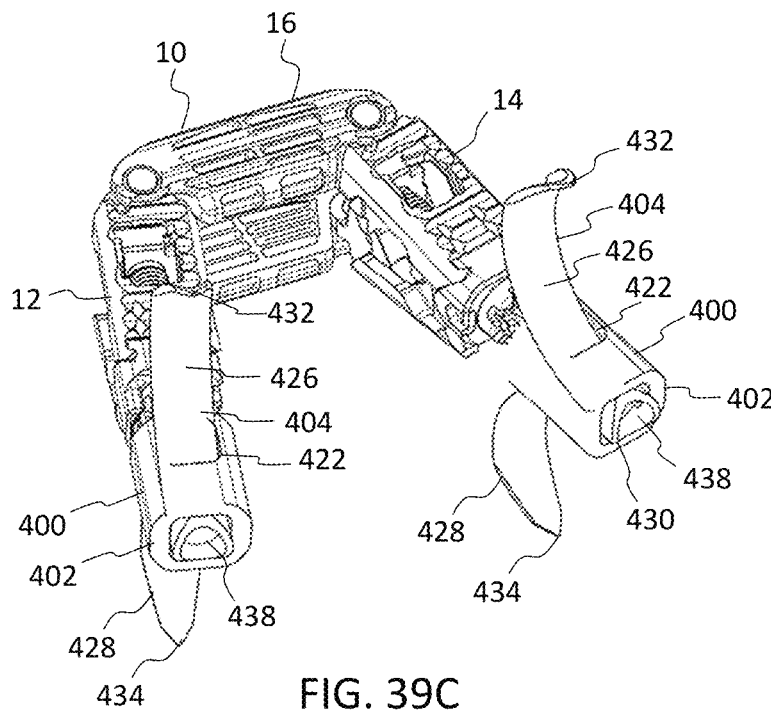
Figure 39D:
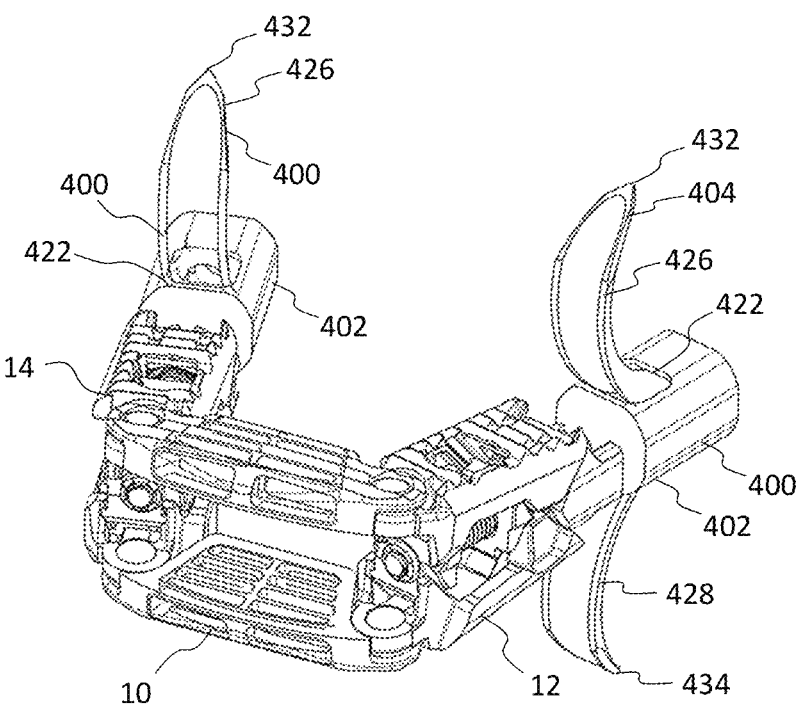
Figure 40A:
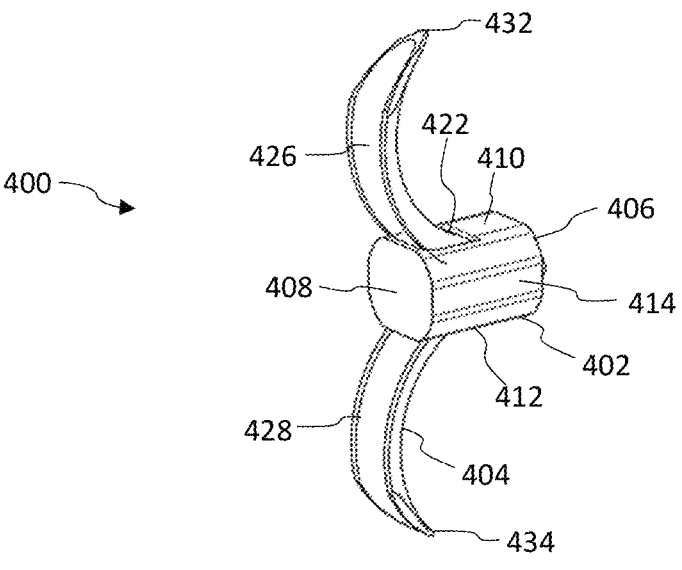
FIG. 40A-40B show perspective and side views, respectively, of the supplemental plate and deployed splayed anchor according to one embodiment.
Figure 40B:
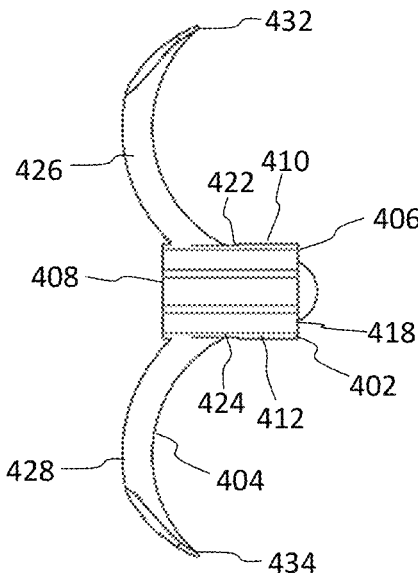

Turning now to FIGS. 33 and 34, the expandable implant 10 and intradiscal fixation systems 300 may be introduced bilaterally through minimally invasive working corridors. FIGS. 33 and 34 show a method for inserting the expandable implant 10 and supplemental intradiscal implants 300 posteriorly and into the intradiscal space 4 between the adjacent vertebral bodies 6. The method may be accomplished through one or more of the following steps in any suitable order: (1) accessing the disc space 4 from a transforaminal approach through Kambin's Triangle or a traditional posterior disc access method; (2) docking one or more tubes or cannulas 8 on the posterior edge of disc space 4 and pressing between the inferior and superior endplates to protect the exiting and traversing nerve roots; (3) performing a discectomy with instrumentation to clear the disc space 4 for the interbody 10 to be placed; (4) placing the interbody footprint 10 to optimize segmental correction and stability prior to inserting the fixation implants 300; and (5) inserting the supplemental fixation systems 300 in the disc space 4 on the same trajectory and orientation as the interbody 10.

FIGS. 35A-35D show the overall system including the expandable implant 10 and a pair of supplemental fixation implants 300. A first supplemental implant 300 may be aligned with the first leg 12 and a second supplemental implant 300 may be aligned with the second leg 14 of the expandable implant 10. Each plate 302 is aligned with the central longitudinal axis of the respective lateral leg 12, 14. In this way, the rear 308 of each plate 302 faces the respective actuation assemblies 50 of the implant 10. The supplemental fixation implants 300 may be introduced secondarily to the expandable implant spacer 10 to improve stability of the intervertebral level.

FIGS. 36A-36E show the overall system implanted into the disc space 4 between adjacent vertebrae 2. The expandable implant 10 may be inserted posteriorly, for example, through minimally invasive access, articulated into position, and expanded in height. Subsequently, two supplemental intradiscal implants may be introduced along the same trajectories as the implant 10. For example, the plates 302 may be inserted on to the posterior edge of the disc space 4 and then the flexible anchors 304 may be inserted into bone. The flexible anchors 304 are configured to bend while being inserted through the plates 302, thereby improving bone purchase and ease of insertion to promote fixation strength and stability.

Turning now to FIGS. 37-38, embodiments of integrated fixation systems 350, 360 are shown. In these embodiments, the anchors 304 are directly combined with the expandable implant spacer body, thereby reducing risk and steps involved with introducing additional implants while providing a more compressed design to fit varying patient anatomy.

With further reference to FIGS. 37A-37D, the integrated fixation implant 350 may include an integrated plate portion 352 for receiving the anchors 304. The components of integrated implant 350 are the same as that for expandable implant 10 except the plate portion 352 mates with the proximal ends 18 of the lateral legs 12, 14 to form the integrated implant 350. The plate portion 352 includes one or more openings 354 configured for receiving the anchors 304. For example, a first opening 354 may be provided from a rear surface through to a top surface of the plate portion 352 and a second opening 354 may be provided from a rear surface through a bottom surface of the plate portion 352. In this manner, a pair of anchors 304 may be used to secure the implant 350 to the superior and inferior vertebral bodies 6. The first and second openings 354 may be centrally located on the plate portion 352 such that the upper and lower anchors 304 are aligned along the same plane. A central opening 356 may extend through the body of the plate portion 352 such that the actuation assembly 50 may be accessed before the anchors 304 are installed. The proximal ends 18 of the upper and lower endplates 22, 24 may include a cutout to receive a portion of the respective anchors 304. The integrated implant 350 may function similarly to the supplemental system 300 whereby after the implant 350 is expanded, the anchors 304 may be introduced, bent during insertion through openings 354, and straighten into the final construct. In this embodiment, the head 330 of the anchor 304 may be inset, flush, or extend outside of the plate portion 352 when fully installed.

With further emphasis on FIGS. 38A-38D, the integrated fixation implant 360 may include endplate extensions 362 for receiving the anchors 304. The components of integrated implant 360 are the same as that for expandable implant 10 except the endplate extension 362 extend the lateral legs 12, 14 to form the integrated implant 350. The endplate extension 362 includes one or more openings 364 configured for receiving the anchors 304. For example, a first cutout or opening 364 may be provided from a rear surface through to a top surface of the upper endplate extension 362 and a second opening 364 may be provided from a rear surface through a bottom surface of the lower endplate extension 362. In this manner, a pair of anchors 304 may be used to secure the implant 360 to the superior and inferior vertebral bodies 6. The first and second openings 364 may be offset to one another such that the upper and lower anchors 304 are not aligned along the same plane. A cutout or gap between the upper and lower endplate extensions 362 may provide for access to the actuation assembly 50 before the anchors 304 are installed. The integrated implant 360 may function similarly to system 350 whereby after the implant 350 is expanded, the anchors 304 may be introduced, and bent during insertion through openings 354. In this embodiment, the heads 330 of the anchors 304 may extend outside of the endplate extensions 362 when fully installed. In this manner, the shaft 332 of the anchors 304 may remain bent inside the extensions 362 in the fully installed position. The remainder of the shafts 332 straighten and angle upward and downward, respectively, into the adjacent vertebral bodies 6, thereby further securing and stabilizing the device in the disc space 4.

Turning now to FIGS. 39-43, the expandable interbody fusion device 10 may be used in combination with one or more intradiscal fixation implants 400. With further emphasis on FIGS. 40A-40B, the supplemental intradiscal fixation system 400 may include a plate 402 and split or splayed anchor 404. The splayed anchor 404 may be inserted through a low/straight profile configuration, guided to the correct depth, and actuated into a deployed configuration through the body of the plate 402.

As best seen in FIGS. 41A-41D, the plate 402 includes a body with front face 406 and opposite rear face 408, top or upper face 410 and bottom or lower face 412, and opposing sides 414, 416. The front and rear faces 406, 408 may be generally planar and parallel with one another. The top and bottom faces 410, 412 may also be generally planar and parallel with one another. The sides 414, 416 may bump out with a planar section between first and second curved portions. The sides 414, 416 may curve between the upper and lower faces 410, 412, for example, with a convex curve. It will be appreciated that any of the plate faces may be flat, angled, curved, or otherwise suitably contoured to fit in the disc space 4.

With further emphasis on FIG. 41D, a bifurcated channel 418 extends through the plate 402. The bifurcated channel 418 may extend between the front face 406 and top and bottom faces 410, 412, thereby guiding insertion of the splayed anchor 404. The bifurcated channel 418 may include a central channel 420 with an upper branch 422 and a lower branch 424. The central channel 420 may begin at the front face 406 and thereafter split into upper branch 422 which terminates as an outlet at upper face 410 and lower branch 424 which terminates as an outlet at lower face 412. The upper and lower branches 422, 424 may be curved or angled to guide the split anchor 404 into the superior and inferior vertebral bodies 6.

With emphasis on FIGS. 42A-42C, the split or splayed anchor 404 is shown according to one embodiment. The splayed anchor 404 includes a body with a first upper arm, blade, or prong 426 and a second lower arm, blade, or prong 428. The upper and lower prongs 426, 428 meet at a proximal end 430 to form a U-shaped loop or bend. The proximal bend 430 between prongs 426, 428 may be about 360° or less. The proximal end 430 may define an opening 438 therethrough. The opening 438 may allow access and/or may interface with an instrument. The upper prong 426 terminates at free end 432 and the lower prong 428 terminates at free end 434. The free ends 432, 434 may be sharpened or pointed in order to pierce bone. Each prong 426, 428 may have blade-like body with an enlarged width relative to its thickness. The width may be generally smaller than the width of the body of the plate 402. Each prong 426, 428 is sized and shaped to be received through the upper and lower branches 422, 424 through the plate 402, respectively.

As best seen in FIG. 42A, the double-pronged anchor 404 may have a straight profile where the upper and lower prongs 426, 428 are aligned substantially in parallel. In the low profiled configuration, the upper and lower prongs 426, 428 may be touching or may have a small gap 436 therebetween. The free ends 432, 434 may be generally aligned with the proximal bend 430, thereby forming the lower profile shape.

The prongs 426, 428 may be flexible such that the free ends 432, 434 are configured to deploy into bone. As shown in FIG. 42B, the free ends 432, 434 of the prongs 426, 428 may bend outward and away from one another. FIG. 42C shows a fully deployed configuration where the prongs 426, 428 are curved outwardly such that the upper prong 426 is configured to engage the superior vertebra 2 and the lower prong 428 is configured to engage the inferior vertebra 2.

The prongs 426, 428 may be composed a nickel titanium alloy, such as nitinol or other shape-memory material, which allows the prongs 426, 428 to bend into the curved state. The properties of a shape-memory material may allow for the anchor 404 to be drawn into the straight configuration from its natural curved state. In its relaxed state, the prongs 426, 428 may have a curve or bend up to 60° or up to 45°, for example, relative to its straight configuration. In its straight state, the prongs 426, 428 may be aligned substantially parallel to one another for easy deployment. The super elastic properties of nitinol allow the low profile configuration shown in FIG. 42A to be loaded into a deployment tube straight and then later deployed through the low-profile corridor back into its curved state shown in FIG. 42C.

The deployment may be assisted with guided plating 402 to help ensure proper placement, deployment, and bone purchase of the anchor system 400. For example, the anchor 404 may be guided into the channel 418 in the front face 406 of the plate 402. As the anchor 404 is pushed or translated forward, the prongs 426, 428 are guided into the respective branches 422, 424, thereby splaying the prongs 426, 428 apart. As the prongs 426, 428 are guided through respective branches 422, 424, prongs 426, 428 curve outwards into their curved configurations. Multiple anchor geometries, tip profiles, and bend radius offerings can be paired with various plating offerings in terms of height, width, and locking caps to help improve bone purchase and ease of insertion to promote fixation strength and stability.

Turning now to FIGS. 43A-43D, the anchor 404 may be deployed through plate 402 with instrument 450. The instrument 450 may include an outer tube 452 and an inner tube 454 extending through outer tube 452. A distal end of the tube 454 may be configured to engage with the front face 406 of the plate 402. The instrument 450 may be configured to push the anchor 404 through plate 402, to thereby deploy the prongs 426, 428 of the anchor 404. For example, the anchor 404 may be positioned in tube 454. When inside tube 454, the anchor 404 may be aligned in the straight configuration.

After the split anchor 404 is loaded into the deployment instrument 450 (for example, though a mode of mechanically actuating the curved anchor 404 into the straight tube 454), the intradiscal plating 402 that assists with guiding the anchors 404 onto the correct trajectory may be attached to the deployment instrument 450 to pre-load the fixation system prior to introducing into the disc space 4. Once properly loaded, instrumentation may be navigated on trajectory and to the appropriate depth for deployment. As for a mode of deployment, the split anchor 404 may be deployed by impaction forces, mechanical actuation, pneumatically actuated, or the like. All modes may be restrained by a hard stop to avoid excessive forces pushing the systems in the anterior direction, thereby potentially damaging bone purchase and intradiscal anatomy. Once fully deployed, a locking cap 440 may be threaded or snapped on to lock the split anchor 404 into the guided plating 402 to increase segment stability and reduce risk of backing out.

Figure 43A:
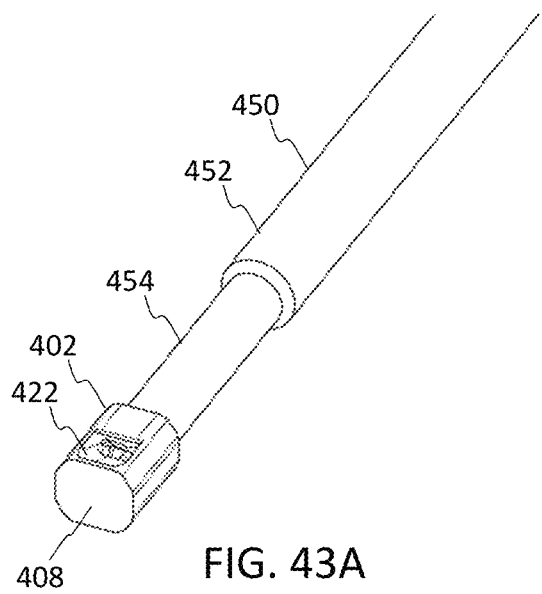
FIGS. 43A-43D show an instrument and steps for deploying the splayed anchors according to one embodiment.
Figure 43B:
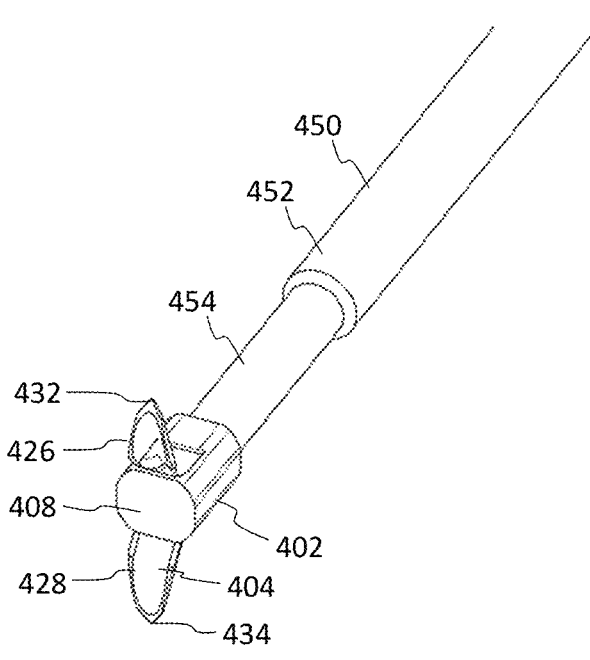
Figure 43C:
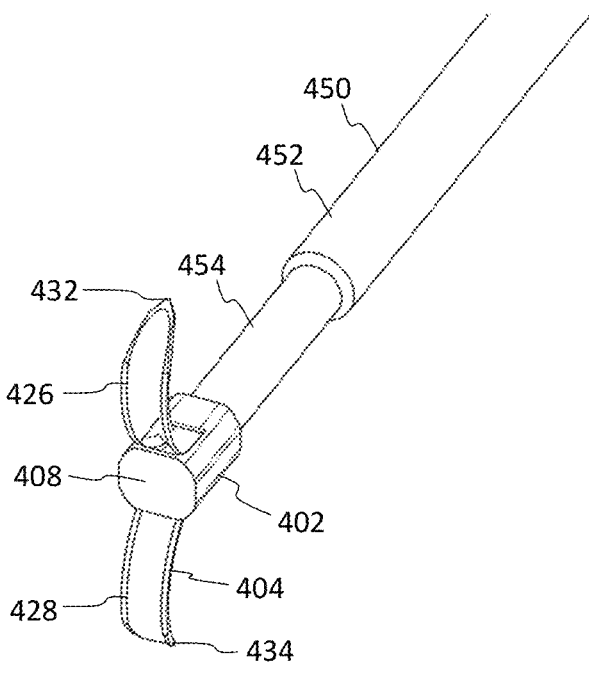
Figure 43D:
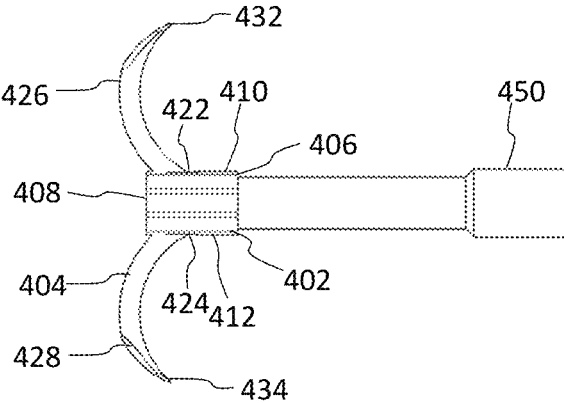
Figures 44A, 44B:
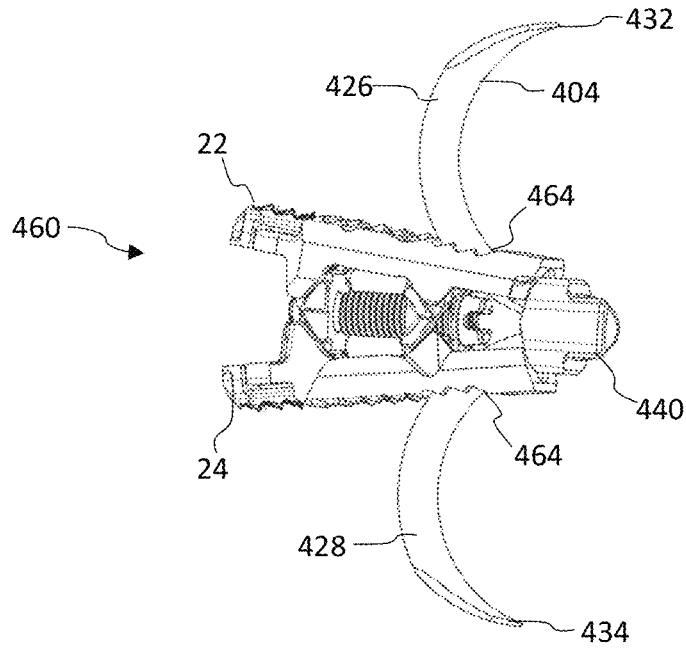
FIGS. 44A-44D show side, top, posterior, and anterior views, respectively, of an expandable fusion device with an integrated fixation system with splayed anchors according to one embodiment.
Figure 44C:
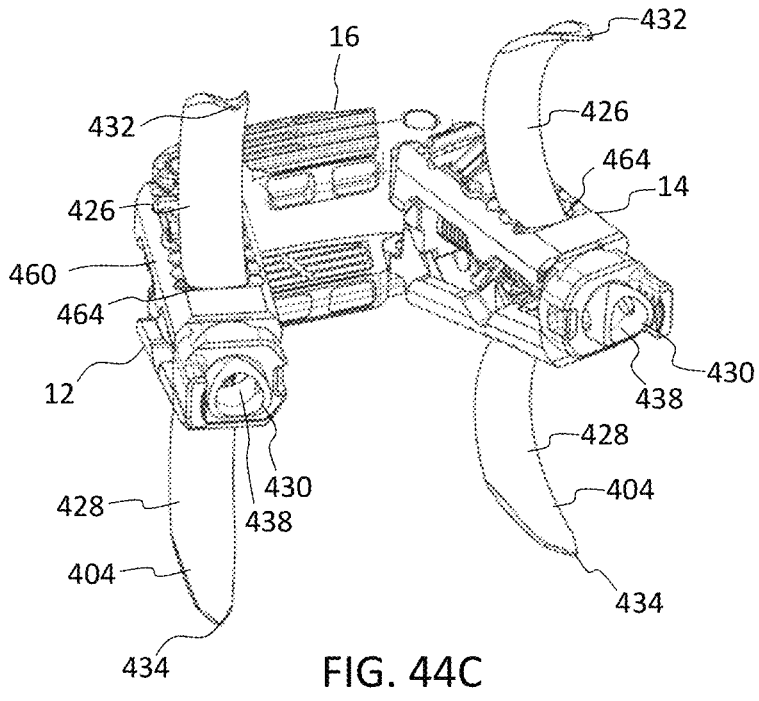
Figure 44D:
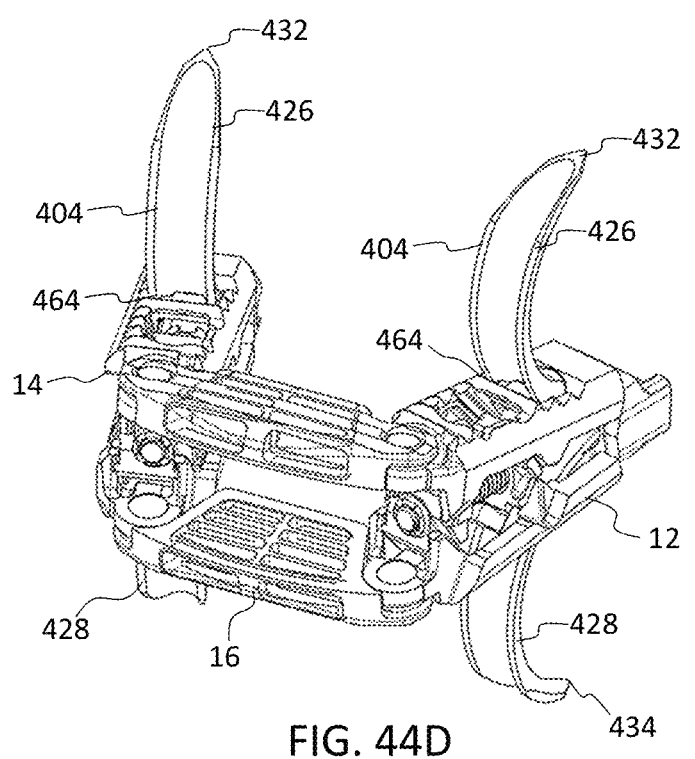
Figure 45A:
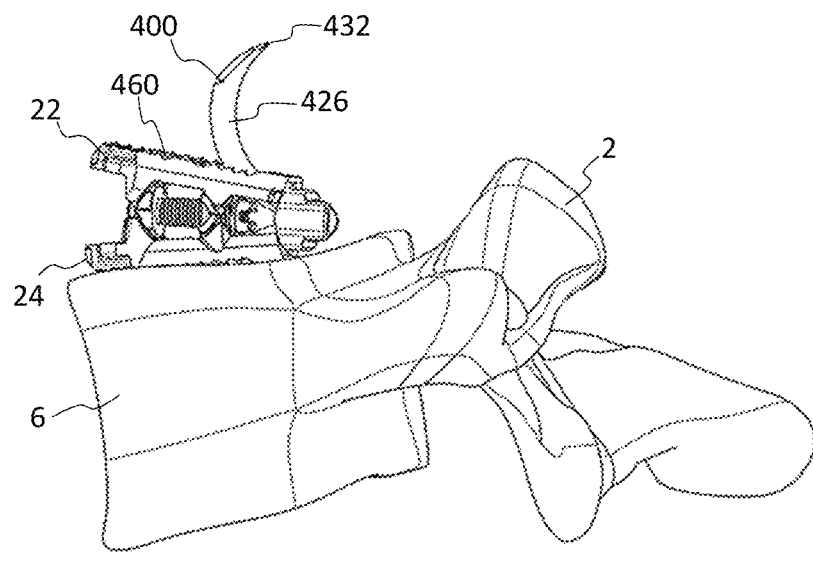
FIGS. 45A-45D show lateral, posterior, axial, and anterior views, respectively, of the integrated fixation and expandable fusion device positioned in the disc space between adjacent vertebrae (the upper vertebra is omitted for clarity)
Figure 45B:
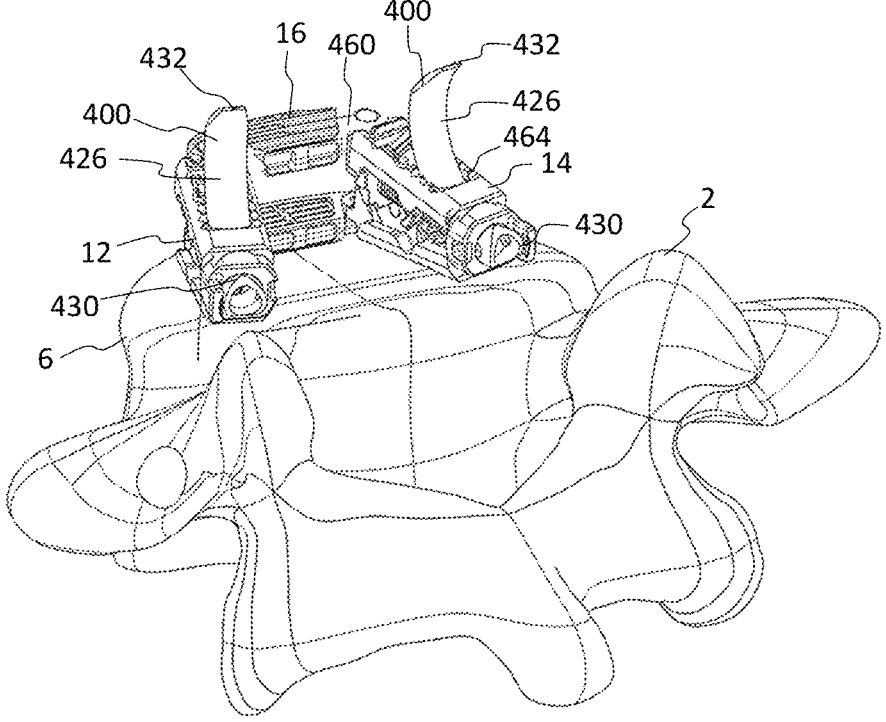
Figure 45C:
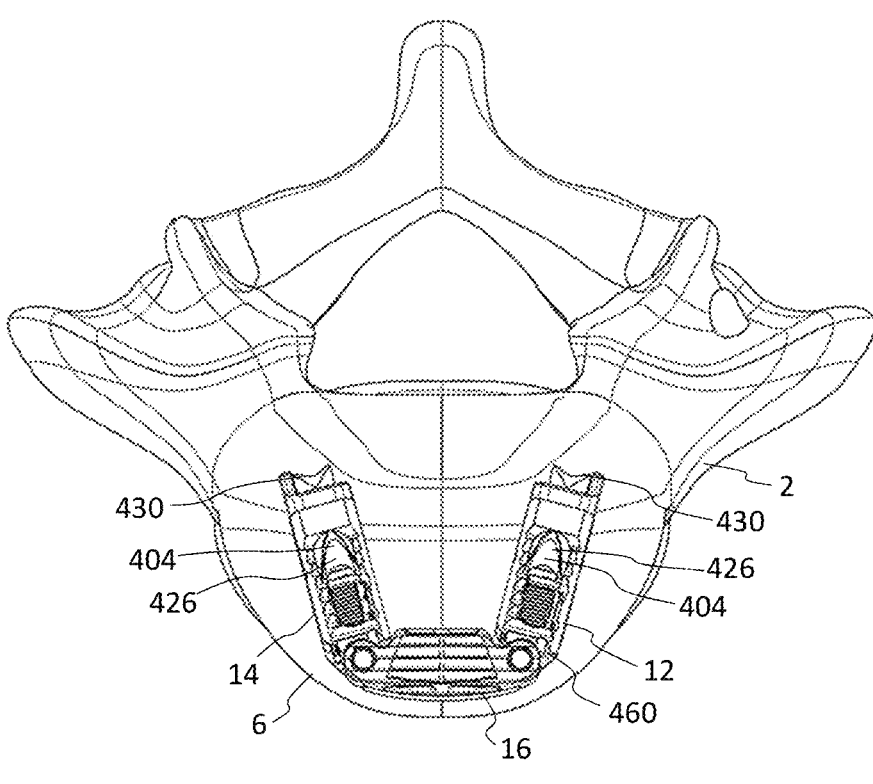
Figure 45D:
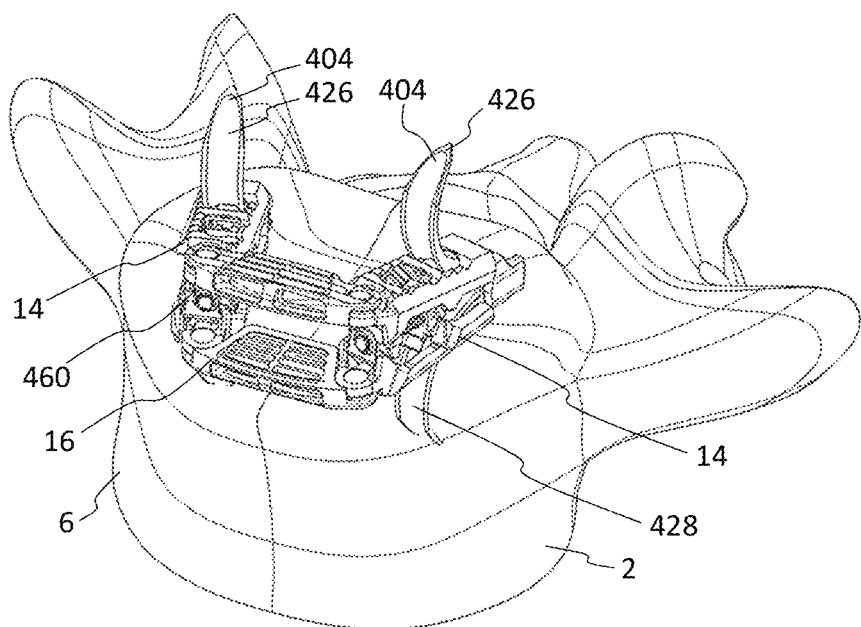

FIG. 43A shows the instrument 450 coupled to the front face 406 of the plate 402. FIG. 43B shows the instrument 450 translating anchor 404 forward, thereby causing prongs 426, 428 to follow branches 422, 424, respectively, and deploy from the upper and lower faces 410, 412 of the plate 402. FIGS. 43C and 43D show the prongs 426, 428 fully deployed from the plate 402 with instrument 450 still attached thereto. After deployment, instrument 450 may be detached and removed from the plate 402.

When fully assembled, the intradiscal fixation system 400 may be inserted bilaterally on the posterior edge of the vertebral body disc space 4. The supplemental fixation implants 400 may be introduced secondarily to the expandable implant spacer 10 to improve stability of the intervertebral level. The placement and proper insertion of the fixation system 400 provides quality bone purchase, avoidance of violating the expanded interbody spacer 10, and provides a positive contribution to the overall construct stability. When pre-operatively planning the split anchor fixation 400, the surgeon may verify that the split anchor 400 is fully placed intradiscally to remove the risk of the distal tips 432, 434 breaching the posterior wall and increasing concerns of injuring neural elements.

Turning now to FIGS. 44-45, embodiments of integrated fixation systems 460 are shown. In these embodiments, the integrated systems 460 allow for the split anchors 404 to be deployed through the spacer endplates, reducing risk and steps involved with introducing additional implants while improving control of deployment through the spacer assembly.

With further reference to FIGS. 44A-44D, the integrated fixation implant 460 may directly receive and secure split anchor 404. The components of integrated implant 460 are the same as that for expandable implant 10 except the endplates 22, 24 of the lateral legs 12, 14 are configured to receive and guide the prongs 426, 428 of anchor 404. The endplates 22, 24 includes one or more openings 464 configured for receiving the anchor 404. For example, a first cutout or opening 464 may be provided from the back through to the top surface of the upper endplate 22 and a second opening 464 may be provided from the back through the bottom surface of the lower endplate 24. The openings 464 may be bifurcated to allow for guidance of the prongs 432, 434 through the endplates 22, 24 of the lateral legs 12, 14. In this manner, a pair of split anchors 404 may be used to secure the implant 460 to the superior and inferior vertebral bodies 6. The first and second openings 464 may be aligned with one another such that the upper and lower prongs 426, 428 are aligned along the same plane. The integrated implant 460 may function similarly to system 400 whereby after the implant 460 is expanded, the anchor 404 may be introduced. The prongs 432, 434 of the anchor 404 may be bent during insertion through openings 464 and remain bent outwardly in the splayed condition. In this embodiment, the proximal ends 430 of the anchors 404 may be inset, flush, or extend outside of the endplates 22, 24 when fully installed.

Adjacent segment disease and other negative surgical outcomes may be attributed to pedicle screw fixation. The intradiscal fixation methods described herein remove the need for pedicle screw fixation while potentially avoiding their iatrogenic effects. The intradiscal devices may lead to improved patient outcomes, efficiency and repeatability, and/or additional stability. With respect to improved patient outcomes, the intradiscal fixation system removes any violation of the superior facet joint, reduces the multitude of incisions and soft tissue disruption, and makes potential disruption of vasculature or lumbar plexus found in anterior and lateral approaches obsolete. With respect to efficiency and repeatability, the same access window previously provided for interbody insertion and placement may be used as an insertion and/or deployment window for the intradiscal fixation systems. The intradiscal fixation systems may also provide improved stability in flexion-extension, lateral bending or axial rotation as a result of being supplemental to maximize placement configuration with patient specific anatomy or integrated to maximize surface area between the interbody and endplates.

The interbody and intradiscal implants described herein may be installed with intelligent instrumentation capable of repeatably providing precision placement of the implants. The procedure may be performed with or without navigation and/or robotic assistance. A robotically-enabled procedure may utilize imaging, navigation, and/or robotics to enhance the quality and efficiency of the posterior procedure through planning and navigable instrumentation.

Figure 46A:
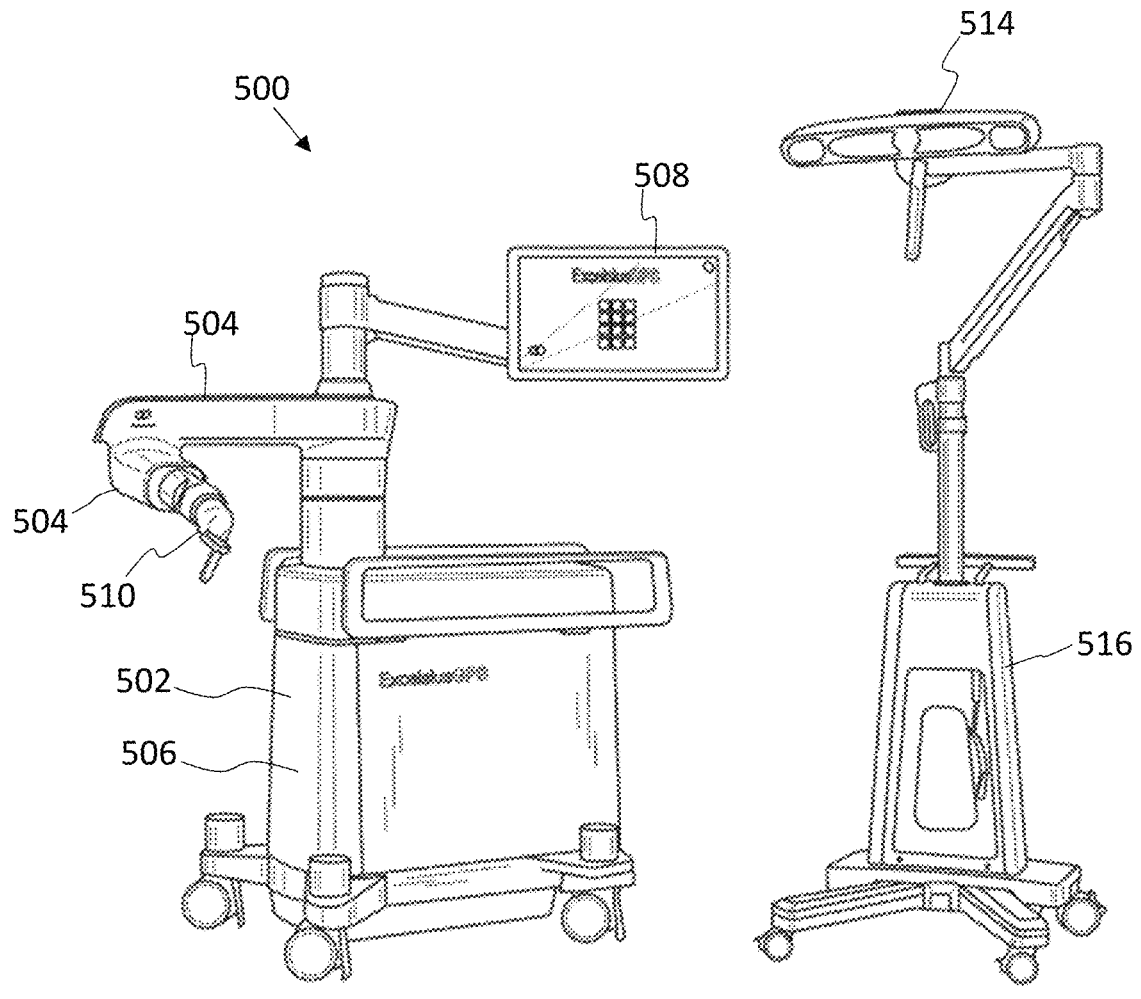
FIGS. 46A-46B depict an example of a robotic surgical system including an end-effector with a guide tube.
Figure 46B:
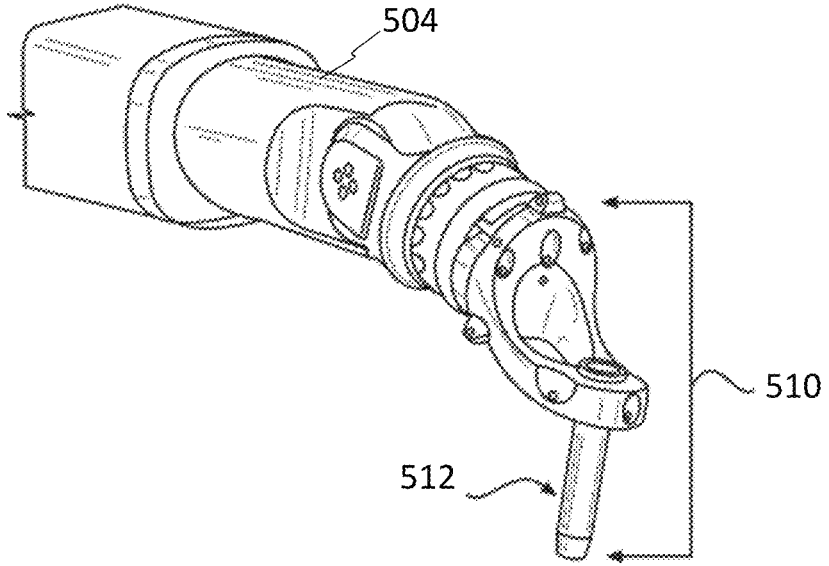

FIGS. 46A-46B illustrate an example of a surgical robotic and navigation system 500. The surgical robot system 500 may include, for example, a surgical robot 502, a base 506 including a computer, a display or monitor 508 (and optional wireless tablet) electronically coupled to the computer, one or more robot arms 504 controlled by the computer, and an end-effector 510 including a guide tube 512 electronically coupled to the robot arm 504. The surgical robot system 500 may also utilize a camera 514, for example, positioned on a separate camera stand 516. The camera stand 516 can have any suitable configuration to move, orient, and support the camera 514 in a desired position. The camera 514 may include any suitable camera or cameras, such as one or more infrared cameras (e.g., bifocal or stereophotogrammetric cameras), able to identify, for example, active and/or passive tracking markers in a given measurement volume viewable from the perspective of the camera 514. The camera 514 may scan the given measurement volume and detect the light that comes from the markers in order to identify and determine the position of the markers in three-dimensions. For example, active markers may include infrared-emitting markers that are activated by an electrical signal (e.g., infrared light emitting diodes (LEDs)), and passive markers may include retro-reflective markers that reflect infrared light (e.g., they reflect incoming IR radiation into the direction of the incoming light), for example, emitted by illuminators on the camera 514 or another suitable device.

The surgical robot 502 is able to control the translation and orientation of the end-effector 510. The robot 502 may be able to move end-effector 510 along x-, y-, and z-axes, for example. The end-effector 510 can be configured for selective rotation about one or more of the x-, y-, and z-axis, and a Z Frame axis (such that one or more of the Euler Angles (e.g., roll, pitch, and/or yaw) associated with end-effector 510 can be selectively controlled). In some exemplary embodiments, selective control of the translation and orientation of end-effector 510 can permit performance of medical procedures with significantly improved accuracy.

The robotic positioning system 502 includes one or more computer controlled robotic arms 504 to assist the surgeon in planning the position of one or more navigated instruments relative to intraoperative patient images. The system 500 includes 2D & 3D imaging software that allows for preoperative planning, navigation, and guidance through a dynamic reference base, navigated instruments, and positioning camera 514 for the placement of spine, orthopedic, or other devices. Further examples of surgical robotic and/or navigation systems can be found, for example, in U.S. Pat.

No. 10,675,094 and U.S. Pat. No. 9,782,229, which are incorporated by reference herein in their entireties for all purposes.

The robot system 500 may utilize a bi-portal posterior access system to place the interbody implant and/or the intradiscal implants. For example, a bi-portal cannula assembly may be configured to attach to the guide tube of the end-effector of the robot. In this manner, the robot is configured to control the location and orientation of the bi-portal cannula assembly relative to the surgical area.

Figure 47:
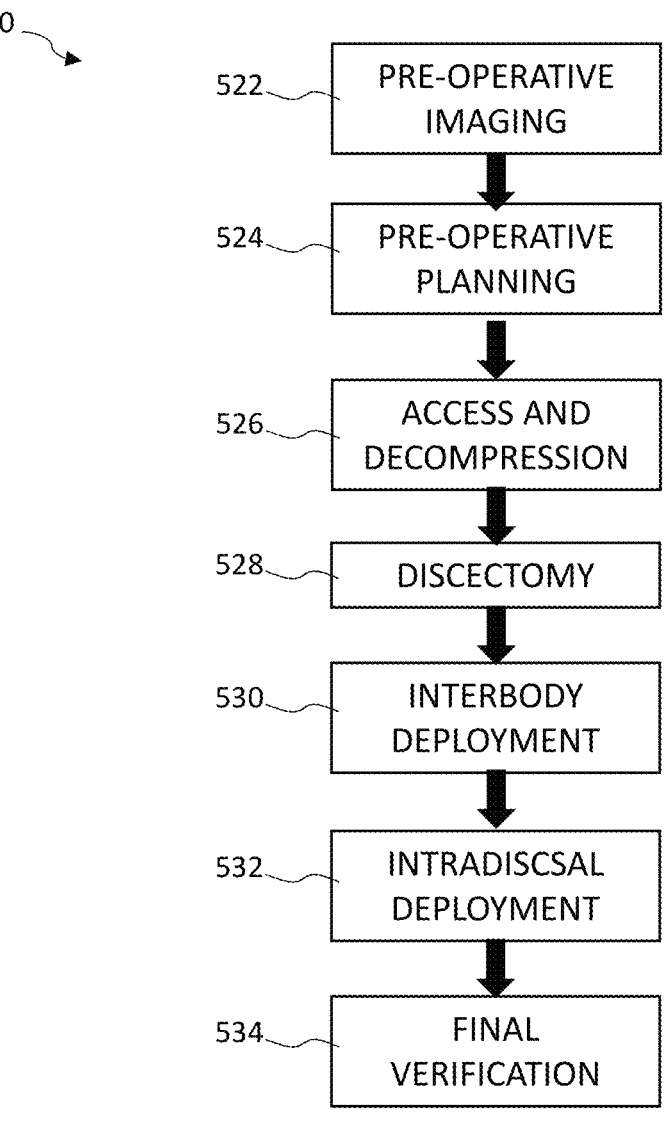
FIG. 47 is a flowchart of a workflow for an interbody fusion with intradiscal fixation according to one embodiment.

Turning now to FIG. 47, the intradiscal procedure may have a structured workflow 520 for preparing and installing the expandable interbody implant and intradiscal implants. The workflow 520 may include one or more of the following steps, in any suitable order: (1) Pre-operative imaging 522 may be performed of the patient anatomy, such as CT (computed tomography), MRI (magnetic resonance imaging), or other relevant imaging. (2) Pre-operative planning 524 may provide for planned placement of the expandable interbody, planned access paths, planned placement of the intradiscal devices, and a review of the plan strategy. (3) Access and decompression 526 of the disc space 4 may be set according to the plan. The disc space 4 may be accessed through a MIS (minimally invasive surgery) or open surgery. The access may utilize navigated instrumentation and/or robotic assistance. (5) A single portal or bi-portal discectomy 528 may be performed to increase the efficiency and overall quality of soft tissue removal. (6) Interbody deployment 530 may include deploying, positioning, articulating, and expanding the implant. (7) Intradiscal deployment 532 may include deploying the intradiscal fixation implants into the vertebral bodies 6 of the superior and inferior vertebrae 2. In the case of supplemental intradiscal fixation implant(s), the plate(s) may be introduced onto the posterior edge of the disc space 4 and the flexible anchors deployed into the vertebral bodies 6. In the case of a standalone implant, the anchor(s) may be directly deployed through the implant and into the vertebral bodies 6. Any suitable anchor system may be selected (e.g., flexible screws or splayed anchor). (8) Final verification 534 may include checking the location of the interbody and/or intradiscal implants and ensuring the final construct is accomplishing the pre-operative plan and achieving the desired correction. Any step of the workflow 520 may be assisted and enhanced using imaging, navigation and/or robotics.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. An intradiscal fixation system comprising:
an expandable implant comprising first and second lateral legs and at least one link plate joined to each of the first and second lateral legs by a hinge, each of the first and second lateral legs including upper and lower endplates configured to engage adjacent vertebrae; and
a pair of intradiscal implants configured to be aligned with the first and second lateral legs of the expandable implant, wherein each intradiscal implant includes a flexible anchor, and the flexible anchor is moveable between a straight configuration and a curved configuration.

2. The intradiscal fixation system of claim 1 wherein the anchor is formed of a shape-memory material.

3. The intradiscal fixation system of claim 1, wherein the anchor is formed of nitinol.

4. The intradiscal fixation system of claim 1, wherein the plate defines first and second openings having one or more threads, and the system includes first and second anchors each having a head and a shaft extending from the head to a distal end, and the shaft includes one or more threads configured to mate with the corresponding threads in the openings, thereby guiding insertion of the anchors.

5. The intradiscal fixation system of claim 1, wherein the plate defines a central channel that bifurcates into upper and lower branches, and the anchor is a split anchor with an upper prong and a lower prong, wherein when the split anchor is inserted through the central channel, the prongs splay apart and are guided by the upper and lower branches to deploy the anchor.

6. The intradiscal fixation system of claim 1, wherein the first and second lateral legs of the expandable implant each include an actuator assembly including a rotatable actuator having a shaft and a rotatable nut, and a plurality of driving ramps including a front ramp, a mid-ramp, and a rear ramp positioned along the shaft of the actuator, wherein the upper and lower endplates are engaged with the plurality of driving ramps, and wherein rotation of the actuator and/or the nut causes movement of one or more of the driving ramps, thereby causing an expansion in height of the upper and lower endplates.

7. The intradiscal fixation system of claim 1, wherein each of the intradiscal implants includes a plate and the respective flexible anchor extending through the plate.

8. The intradiscal fixation system of claim 7, wherein the plate of each of the intradiscal implants includes first and second openings between front and rear faces, and the first and second openings are configured to receive a respective flexible anchor.

9. The intradiscal implant of claim 8, wherein the first opening is angled such that the first opening is oriented downwardly and the second opening is angled such that the second opening is oriented upwardly, thereby allowing for the respective flexible anchors to engage the adjacent vertebral bodies.

* * * * *